US005985599A

United States Patent [19]
McKenzie et al.

[11] Patent Number: 5,985,599
[45] Date of Patent: Nov. 16, 1999

[54] FC RECEPTOR FOR IMMUNOGLOBULIN

[75] Inventors: Ian F. C. McKenzie; Mark P. Hogarth; Margaret L. Hibbs; Bernadette M. Scott; Lisa Bonadonna; Mark D. Hulett, all of Victoria, Australia

[73] Assignee: The Austin Research Institute, Heidelberg, Australia

[21] Appl. No.: 08/332,562

[22] Filed: Oct. 31, 1994

Related U.S. Application Data

[62] Continuation-in-part of application No. 07/896,457, May 27, 1992, Pat. No. 5,451,669, which is a continuation of application No. 07/174,991, filed as application No. PCT/AU87/00159, May 29, 1987, abandoned.

[30] Foreign Application Priority Data

May 29, 1986 [AU] Australia ............................... PH6166
Sep. 16, 1994 [AU] Australia ............................ PM8232/94

[51] Int. Cl.$^6$ ........................ C07K 14/705; C12N 15/12
[52] U.S. Cl. ................. 435/69.1; 435/252.3; 435/320.1; 530/350; 536/23.5
[58] Field of Search ................................. 435/69.1, 69.7, 435/172.3, 320.1, 252.3; 536/23.4, 23.5

[56] References Cited

U.S. PATENT DOCUMENTS

| | | | |
|---|---|---|---|
| 4,948,874 | 8/1990 | Kronvall et al. ......................... | 530/350 |
| 4,962,035 | 10/1990 | Leder et al. ............................. | 435/320 |
| 5,143,844 | 9/1992 | Abrahmsén et al. ................. | 435/257.3 |
| 5,189,014 | 2/1993 | Cowan, Jr. .................................. | 514/2 |

OTHER PUBLICATIONS

Cowan, F.M., *Toxicology Methods*, 7:9–15 (1997).
Ravtech, J.V. et al., *Science*, 234:718–725 (1986).
Bouchard, C. et al., *J. Exp. Med.*, 182:1717–1726 (1995).
Sautes et al., *J. Chromotography B–Biomedical Applications*, 662:197–207 (1994) (Abstract Only).
Barclay, A.N. et al., *The Leucocyte Antigen FactsBook*, Acad. Press, pp. 136–137, 170–172 (1993).
Eliasson, M. et al., *J. Biol. Chem.*, 263:4323–4327 (1988).
Parren, P.W.H.I. et al., *J. Clin. Invest.*, 90:1537–1546 (1992).
Mallimaci, M.A. et al., *J. Biol. Chem.*, 268:22076–22083 (1993).
Hibbs, M.L. et al., *J. Immol.*, 152:4466–4474 (1994).
Hulett, M.D. et al., *J. Biol. Chem.*, 269:15287–15293 (1994).
Sautes, C. et al., *Immol. Res.*, 11:181–190 (1992).
Young et al., "Mouse Macrophage Fc Receptor . . . ", Proc. Natl. Acad. Sci. USA, vol. 80, Mar. 1983, pp. 1636–1640.
Green et al., "Biosynthesis and Intracellular Transport . . . ", J. Biol. Chem., vol. 260, 1985, pp. 9867–9874.
Holmes et al., "Alleles of the Ly–17 Alloantigen Define . . . ", Proc. Natl. Acad. Sci. USA, vol. 82, Nov. 1985, pp. 7706–7710.
Anderson et al., "Characterization of the Fc Receptor for . . . ", J. Immunology, vol. 125, No. 6, Dec. 1980, pp. 2735–2741.
Hibbs et al., "The Mouse Ly–17 Locus Identifies . . . ", Immunogentics, vol. 22, 1985, pp. 335–348.
Suggs et al., "Use of Synthetic Oligonucleotides . . . ", Proc. Natl. Acad. Sci. USA, vol. 78, No. 11, Nov. 1981, pp. 6613–6617.
Brooks et al., "Structure and Expression of Human IgG FcRII(CD32)", J. Exp. Med., vol. 170, Oct. 1989, pp. 1369–1385.
Zeger et al., "Characterization and Expression of an Fc . . . ", Proc. Natl. Acad. Sci. USA, vol. 87, May 1990, pp. 3425–3429.
Litman et al., "Complete Nucleotide Sequence of an Immunoglobulin . . . ", Nature, vol. 303, May 1983, pp. 349–352.
Litman et al., "Immunoglobulin $V_H$ Gene Structure and . . . ", Proc. Natl. Acad. Sci. USA, vol. 82, Apr. 1985, pp. 2082–2086.
Hulett et al., "Chimeric Fc Receptors Identify . . . ", Eur. J. Immunol., vol. 23, 1993, pp. 640–645.
Toh et al., "Retroviral gag and DNA Endonuclease . . . ", Nature, vol. 318, Nov. 1985, pp. 388–389.
Löwy et al., "Isotype Regulation of Antibody Production . . . ", Proc. Natl. Acad. Sci. USA, vol. 80, 1983, pp. 2323–2327.
Martens et al., "cDNA Clones Encoding IgE–binding Factors . . . ", Proc. Natl. Acad. Sci. USA, vol. 82, 1985, pp. 2460–2464.
Liu et al., "Identification of an IgE–binding Protein . . . ", Proc. Natl. Acad. Sci. USA, vol. 82, 1985, pp. 4100–4104.
Tate et al., "Expression of the High Responder/Non–responder . . . ", Immunology and Cell Biology, vol. 70, 1972, pp. 79–87.
Fomusek et al., "Fc Receptor –More Answers . . . ", Folia Microbiol., vol. 29, 1984, pp. 476–516.
Vaughn et al., "Characterization of Human IgG Fc Receptors", J. Immunology, vol. 135, No. 6, Dec. 1985, pp. 4059–4065.
Ravetch et al., "Structural Heterogeneity and Functional Domains . . . ", Science, vol. 234, 1986, pp. 718–725.
Lewis et al., "A Complementary DNA Clone for a Macrophage–Lymphocyte . . . ", Nature, vol. 324, Nov. 1986, pp. 372–375.
Hibbs et al., "The Murine Fc Receptor for Immunoglobulin . . . ", Proc. Natl. Acad. Sci. USA, vol. 83, Sep. 1986, pp. 6980–6984.

(List continued on next page.)

*Primary Examiner*—John Ulm
*Attorney, Agent, or Firm*—Foley & Lardner

[57] ABSTRACT

Nucleotide sequences encoding a protein with Fc receptor activity or a fragment thereof that is capable of binding the Fc region of immunoglobulin and polypeptides with Fc receptor activity are provided. Proteins which exhibit enhanced or reduced immunoglobulin binding ability relative to native Fc receptors and nucleotides encoding these proteins also are provided. The invention also provides methods of determining the presence of immunoglobulin, detecting an immune complex, removing immunoglobulin from a body fluid and treating disease using the proteins.

61 Claims, 22 Drawing Sheets

OTHER PUBLICATIONS

Hempstead et al., "Characterization of the IgE Receptor Isolated . . . ", J. Immunology, vol. 123, No. 5, Nov. 1979, pp. 2283–2291.

Kulczycki et al., "Purification of Fc Receptor from Rabbit Alveolar . . . ", J. Immunology, vol. 124, No. 6, Jun. 1980, pp. 2772–2779.

Loube et al., "Isolation of an Fc–Binding Protein from the Cell . . . ", J. Immunology, vol. 120, No. 3, Mar. 1978, pp. 709–715.

Fernandez–Botran et al., "Biochemical Properties of Phosphatidylcholine–Binding . . . ", Biochemistry, vol. 24, 1985, pp. 1896–1903.

Creighton, *Proteins Structures and Molecular Principles*, Freeman and Co., New York, pp. 39–42.

Kikutani et al, *Cell* 47:657–665, Dec. 5, 1986.

Bass et al. A systematic mutational analysis of hormone–binding determinants in the human growth hormone receptor. P.N.A.S. 88:4498–4502, May 1991.

FIG. 1A

CTGCAGACTCGCTCCAGAGCTGATGGGAATCCTGCCGTTCCTACTGAT

His Met Leu Trp Thr Ala Val Leu Asn Leu Ala Ala
CAT ATG CTA CTG TGG ACA GCC GTG CTA AAT CTT GCT GCT
    -10                  20

Ile Gln Val Leu Lys Glu Asp Thr Val Thr Leu Thr Cys
ATC CAG GTG CTC AAG GAA GAC ACG GTG ACA CTG ACA TGC
                                          50

Gly Arg Ser Ile Arg Ser Gln Val Gln Ala Ser Tyr Thr
GGG AGG TCC ATC CGG AGC CAG GTC CAA GCC AGC TAC ACG

Gln Thr Arg Leu Ser Asp Val Asp Leu Gly Val Ile
CAG ACC CGC CTC AGC GAC CCT GTA GAT CTG GGA GTG ATT
                         80        110

Glu Thr Ile Thr Leu Arg Cys His Ser Trp Arg Asn Lys
GAA ACC ATC ACG CTA AGG TGC CAT AGC TGG AGG AAC AAA
                                          140     *

His Tyr Ser Ser Asn Phe Ser Ile Pro Lys Ala Asn
CAT TAC AGT AGT AAT TTC TCT ATC CCC AAA GCC AAC
                         170

Leu His Gln Ser Lys Pro Val Ala Ala Thr Ile Val Gln Gly
CTG CAC CAG TCC AAG CCT GTC GCA ACT ATC GTC CAA GGG
190                                  200

Thr Gly Ile Val Ala Val Ile Ile Leu Val
ACT GGG ATT GCT GTC GCA GCC ATT GTT ATC CTA GTA
                                          230

Pro Asp His Arg Glu Met Gly Glu thr Leu Pro Glu Glu
CCT GAT CAC AGG GAA ATG GGA GAA ACC CTT CCA GAG GAA
220  TM                                       260
250

Gly Pro Pro Ser Gly Leu Glu Pro Thr Ser Ser Ser Pro
GGG CCT CCA TCT GGA CTG GAG CCA ACA AGC AGC CCA
280

Thr Ile Thr Tyr Ser Leu Leu Lys His Pro Glu Ala Leu
ACG ATC ACC TAC TCA CTC CTC AAG CAT CCC GAA GCC TTG
ATTGGGAAAAGCAAGCCAGAAAGGCCAGGATCTAGTGTCTCCTGGTCCAAG
CTACGAGAGATTGGTTCCCAATGGTTGACTGTACTAATGACTCCCATAACTTA
TGCCGTTAAGAGACTGCAG

FIG. 1B

```
        -29
        Met Glu Ser Asn Trp Thr Val His Val Phe Ser Arg Thr Leu Cys
CCCC    ATG GAG AGC AAC TGG ACT GTC CAT GTG TTC TCA CGG ACT TTG TGC
        -1                                  -20
        Gly Thr His Asp Leu Pro Lys Ala Val Val Leu Glu Pro Pro Trp
GGG    ACT CAT GAT CTT CCA AAG GCT GTG CTC GAG CCC CCG TGG
        +1                                   10
                                             NH2
        Glu Gly Thr His Asn Pro Gly Asn Ser Ser Thr Gly Trp Phe His Asn
GAA    GGG ACC CAC AAC CCT GGG AAC TCT TCT ACC CAG TGG TTC CAC AAT
        30                                          40
        Phe Lys Ala Thr Val Asn Asp Ser Gly Glu Tyr Arg Cys Gln Met Glu
TTT    AAG GCC ACA GTC AAT GAC AGT GGA GAA TAT CGG TGT CAA ATG GAG
        60                                          70
        Ser Asp Trp Leu Leu Leu Gln Leu Thr Pro Gln Leu Val Phe Leu Glu Gly
TCT    GAC TGG CTG CTC CTC CAG CTG ACC CAG CTG GTG TTT CTG GAA GGG
        90                                      100
        Leu Leu Asn Arg Ile Ser Phe His Asn Glu Lys Ser Val Arg Tyr
CTA    CTG AAC AGG ATC TCG TTC CAT AAT GAA AAA TCC GTG AGG TAT
        120                                 130
        His Ser His Gly Asp Tyr Cys Lys Gly Leu Gly Arg Thr
CAC    AGT CAC GGG GAC TAC TGC AAA GGA CTA AGG ACA
        150                             160
        Pro Lys Ser Arg Arg Ser Leu Pro Val Leu Thr Ile Val Ala Val
CCC    AAG TCC AGC AGG TCT TTA CCA GTA TTG ACA ATT GTG GCT GTC
        180                             
        Ser Leu Val Tyr Leu Lys Lys Gln Pro Ala Leu Pro Gly Asn
TCC    TTG GTC TAT CTC AAG AAA CAG CCA GCT CTC CCA GGA AAC
        210
        Val Gly Glu Tyr Arg Gln Pro Ser Gly Ser Val Pro Val Ser Pro
GTA    GGT GAG TAC AGA CAG CCC TCT GGC TCA GTC CCT GTC AGC CCA
        240
        Tyr Asn Pro Pro Asp Leu Glu His Asp Pro Lys Thr Glu Ala Asn
TAC    AAT CCT CCT GAT CTG GAA CAT GAT CCC AAA ACT GAG AAC
        270
        Asp Glu Glu Thr Glu His Thr Tyr Gln Asn His Ile ***
GAT    GAA GAA ACA GAG CAT ACA TAC CAA AAC CAC ATT TAG TCTCCCTTGGC
        290
GGATGCTGTAGATATTAAAGAAAACATCCAGAGTCACTTCTGTGAGTCCTGAAACCAACAGACA
CAGCTTCCCAACTCAAGACTCTTCTGCTATCGATCCACACTGCCACTAAAATTAATCAACTTAC
```

FIG. 2

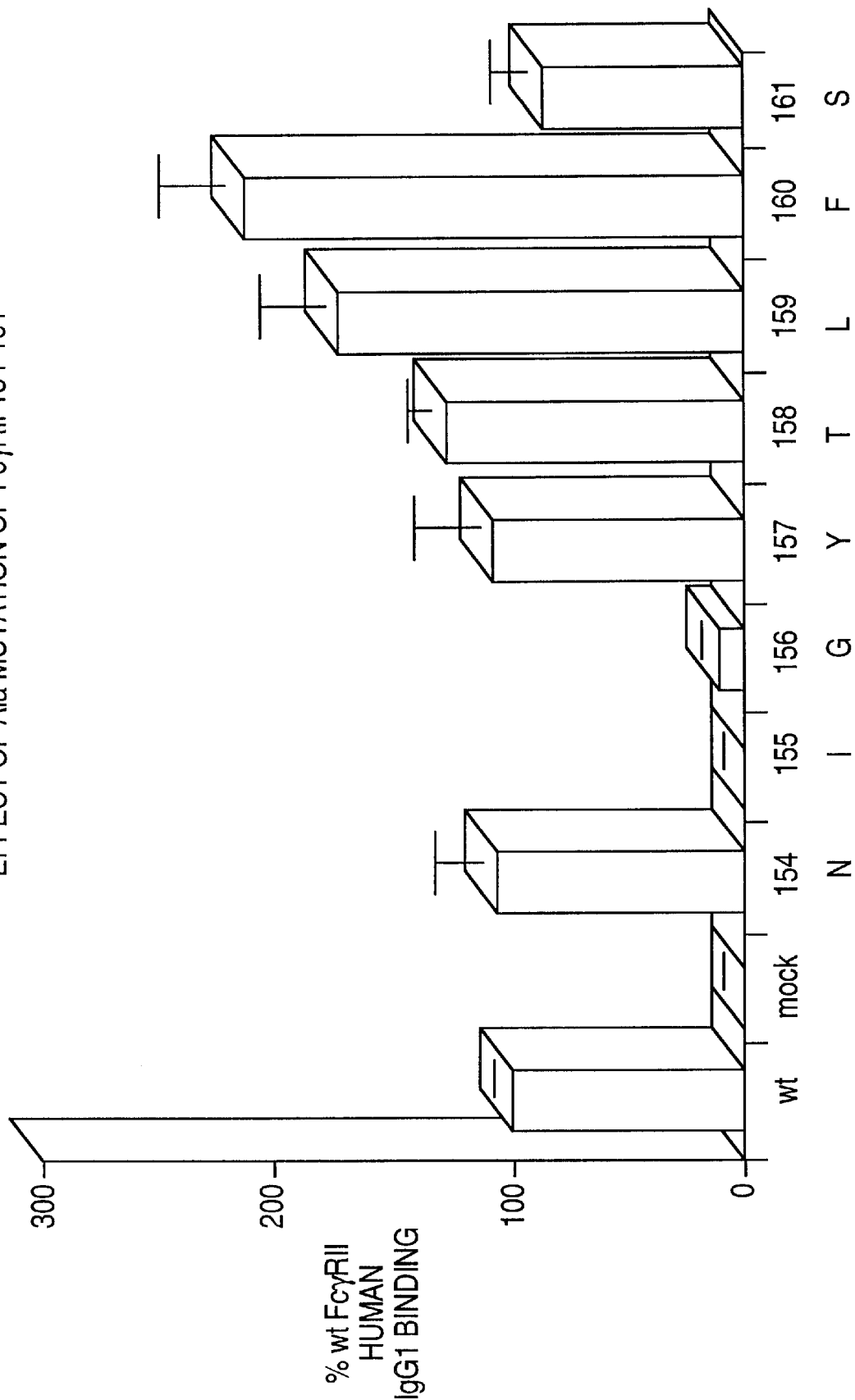

FIG. 6A    IMMUNOGLOBULIN TRUNCATED C2 DOMAINS

1. HUMAN CD4-2:
2. MOUSE CD4 (L3T4)-2:
3. RAT CD4 (W3/25)-2:
4. HUMAN CD4-4:
5. HUMAN Fcε RI D1:
6. HUMAN Fcε RI D2:
7. HUMAN FcγRII D1:
8. HUMAN FcγRII D2:
9. HUMAN FcγRI D1:
10. MOUSE FcγRI D2:
11. MOUSE FcγRI D3:

```
          A                       B                   C                       C'            E                                   F                           G
 1. ----FGLTANSDTHLLQGSLTLTLES-PPG--SSPSVQCRSPRG---KNIQG-GKTLSVSQLELQDSGTWTCTVLQ--NQKKVQFKIDIVVL
 2. ----FKVTFSPGTSLLQGSLTLTLDSNSKV--SNPLTECKHKKG----KVVSG-SKVLSMSNLRVQDSDFWNCTVTL--DQKKNWFGMTLSVL
 3. ----FRVTFNPGTRLLQGSLTLILDSNPKV--SDPPIECKHK-----SSNIVKDSKAFSTHSLRIQDSGIWNCTVTL--NQKKHSFDMKLSVL
 4. TGKLHQEVNLVVMRATQLQ-KNLTCEVWGPT--S-PKLMLSLKLENKEAKVSKREKAVWLNP---EAGMWQCLLSD---SGQVLLESNIKVL
 5. PQKPKVSLNPPWNRIFKGENVTLTCNGNNFF--EVVSTKWFHN-GSLSEETNS----SLNIVNAKFEDSGEYKCQHQQVNESEPVYLEVFSDWL
 6. ----WLLLQASAEVVMEGQPLFLRCHGWRNW--DVYKVIYYKD-GEALKYWYEN-HNISITNATVEDSGTYYCTGKVW-QLDYESEPLNITVI
 7. PPKAVLKLEPPWINVLQEDSVTLTCQGARSP--ESDSIQWFHN-GNLIPTHTQ-PSYRFK-ANNNDSGEYTCQTGQTSLSDPVHLTVLSEWL
 8. ----WLVLQTPHLEFQEGETIMLRCHSWKDK--PLVKVTFFQN-G-KSQKFSHLDPTFSIPQA-HSHSGDYHCTGNIG-YTLFSSKPVTITVQ
 9. ATKAVITLQPPWVSIFQKENVTIWCEGPHLP--GDSSTQWFIN-G-TAVQIST--PSYSIPEASPQDSGEYRCQIGSSMPSDPVQLQIHNDWL
10. ----LLQASRRVLTEEPLALRCHGWKNK---LVYNVEYRN-G-KSPQFSS-DSEVAILKTNLSHSGIYHCSGTGRHRYTSAGVSITVKEL
11. -FTTPVLRASVSSPFPEGSLVTLNCETNLLLQRPGLQHFSFYVGSKILEYRNTSSEYHIARAEREDAGFYWCEVAT-EDSSVLKRSPELELQ
```

FIG. 6B  IMMUNOGLOBULIN TRUNCATED C2 DOMAINS

1. HUMAN CD4-2:
2. MOUSE CD4 (L3T4)-2:
3. RAT CD4 (W3/25)-2:
4. HUMAN CD4-4:
5. HUMAN Fcε RI D1:
6. HUMAN Fcε RI D2:
7. HUMAN Fcγ RII D1:
8. HUMAN Fcγ RII D2:
9. MOUSE Fcγ RI D1:
10. MOUSE Fcγ RI D2:
11. MOUSE Fcγ RI D3:

```
         A                    B                      C                    C'                 E                         F                          G
1.  ----FGLTANSDTHLLQGQSLTLTLES-PPG--SSPSVQCRSPRG---KNIQG-GKTLSVSQLELQDSGTWTCTVLQ---NQKKVQFKIDIVL
2.  ----FKVTFSPGTSLLQGQSLTLTLDSNSKV--SNPLTECKHKKG---KVVSG-SKVLSMSNLRVQDSDFWNCTVTL--DQKKNWFGMTLSVL
3.  ----FRVTFNPGTRLLQGQSLTLILDSNPKV--SDPPIECKHK-----SSNIVKDSKAFSTHSLRIQDSGIWNCTVTL--NQKKHSFDMKLSVL
4.  TGKLHQEVNLVVMRATQLQ-KNLTCEVWGPT--S-PKLMLSLKLENKEAKVSKREKAVWVLNP---EAGMWQCLLSD---SGQVLLESNIKVL
5.  PQKPKVSLNPPWNRIFKGENVTLTCNGNNFF--EVVSTKWFHN-GSLSEETNS---SLNIVNAKFEDSGEYKCQHQQVNESEPVYLEVFSDWL
6.  ----WLLQASAEVVMEGQPLFLRCHGWRNW---DVYKVIYYKD-GEALKYWYEN-HNISITNATVEDSGTYYCTGKVW-QLDYESEPLNITVI
7.  PPKAVLKLEPPWINVLQEDSVTLTCQGARSP--ESDSIQWFHN-GNLIPTHTQ-PSYRFK-ANNNDSGEYTCQTGQTSLSDPVHLTVLSEWL
8.  ----WLVLQTPHLEFQEGETIMLRCHSWKDK--PLVKVTFFQN-G-KSQKFSHLDPTFSIPQA-HSHSGDYHCTGNIG-YTLFSSKPVTITVQ
9.  ATKAVITLQPPWVSIFKENVTLWCEGPHLP---GDSSTQWFIN-G-TAVQIST--PSYSIPEASPQDSGEYRCQIGSSMPSDPVQLQIHNDWL
10. ----LLQASRVLTEEPLALRCHGWKNK------LVYNVFYRN-G-KSPQFSS-DSEVAILKTNLSHSGIYHCSGTGRHRYTSAGVSITVKEL
11. -FTTPVLRASVSSPFPEGSLVTLNCETNLLLQRPGLQHFSFYVGSKILEYRNTSSEYHIARAEREDAGFYWCEVAT-EDSSVLKRSPELELQ
```

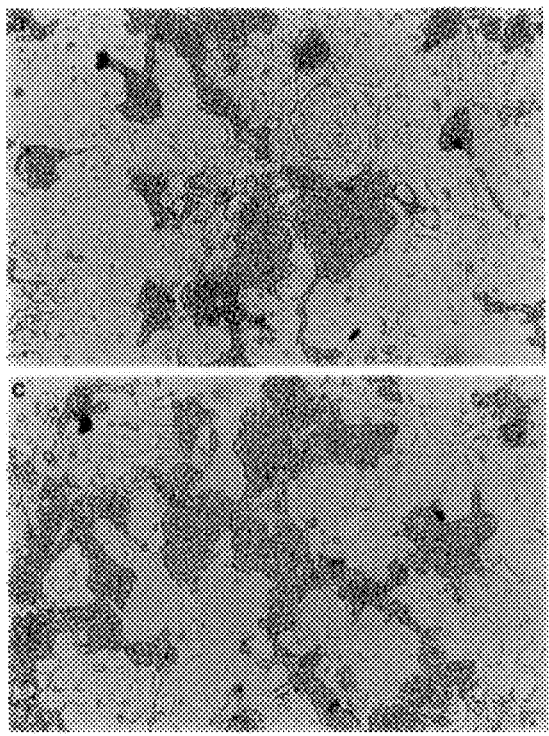
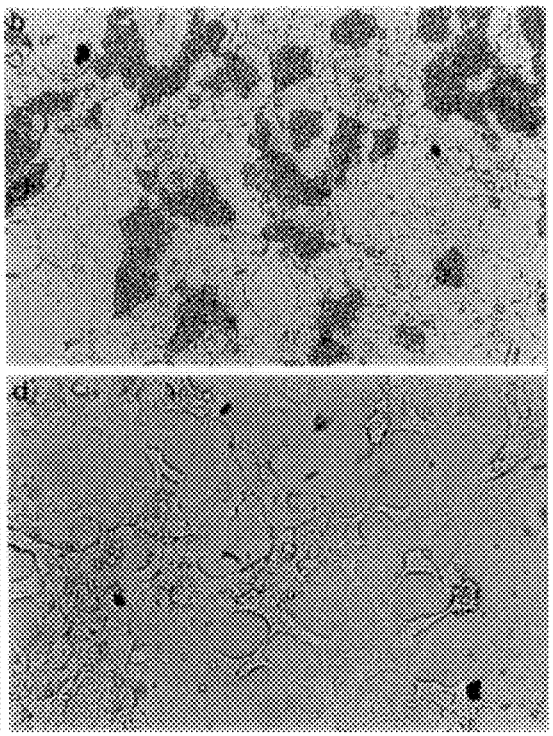
FIG. 7A  FIG. 7B
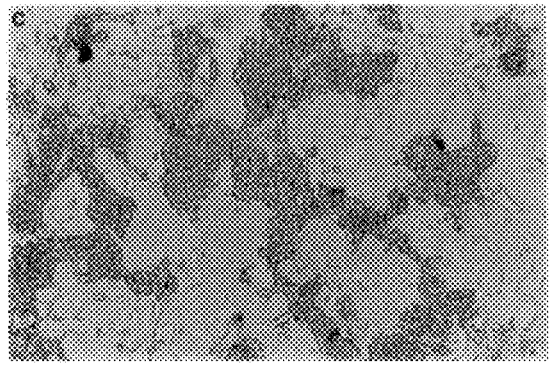
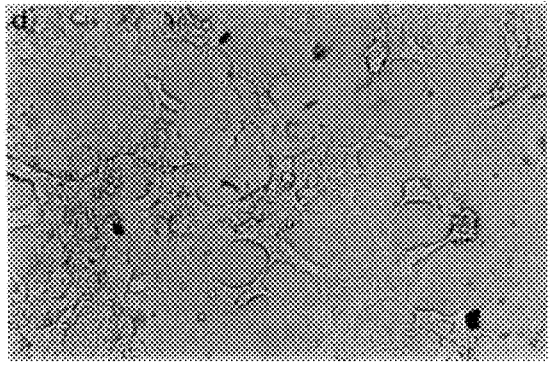
FIG. 7C  FIG. 7D

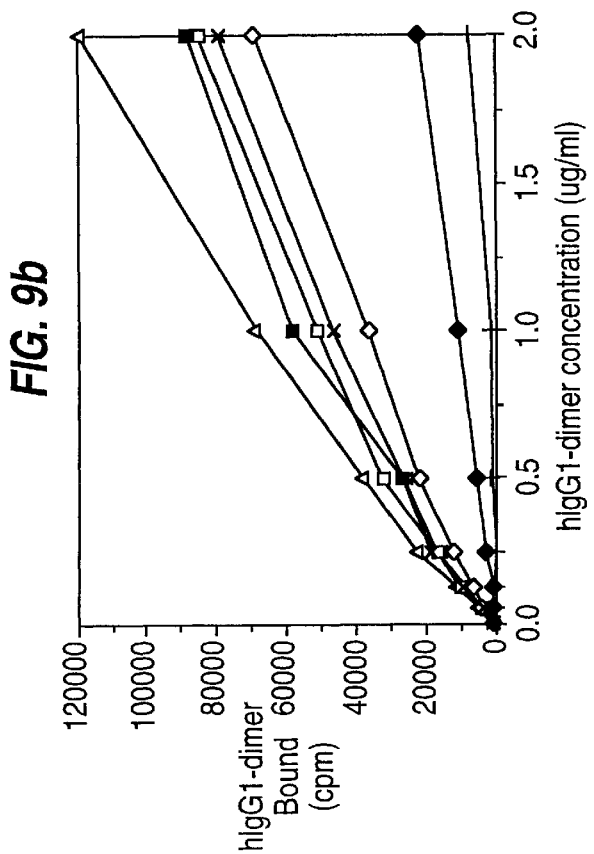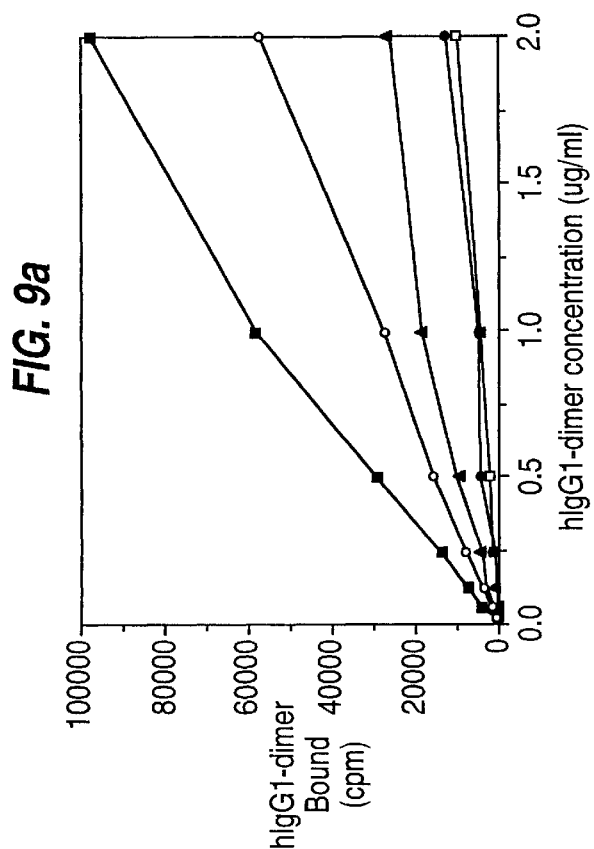

FIG. 11A huFc$_\varepsilon$RIa chain C'-E, F-G loop Ala mutant oligo nucleotides F-G loop e154 (Lys) ® Ala     EFG-01+EFG-02
EFG-01:     5' CTGTACGGGCGCAGTGTGGCAGC 3'
EFG-02:     5' GCTGCCACACTGCGCCCGTACAG 3' e155 (Val) ® Ala     EFG-03+EFG-04
EFG-03:     5' GTACCGGCAAAGCATGGCAGCTGG 3'
EFG-04:     5' CCAGCTGCCATGCTTTGCCCGTAC 3' e156 (Trp) ® Ala     EFG-05+EFG-06
EFG-05:     5' GGGCAAAGTGGCACAGCTGGAC 3'
EFG-06:     5' GTCCAGCTGTGCCACTTTGCCC 3' e157 (Gln) ® Ala     EFG-07+EFG-08
EFG-07:     5' GCAAAGTGTGGGCACTGGACTATG 3'
EFG-08:     5' CATAGTCCAGTGCCCACACTTTGC 3' e158 (Leu) ® Ala     EFG-09+EFG-10
EFG-09:     5' GTGTGGCAGGCAGACTATGAGTC 3'
EFG-10:     5' GACTCATAGTCTGCCTGCCACAC 3' e159 (Asp) ® Ala     EFG-11+EFG-12
EFG-11:     5' GTGGCAGCTGGCATATGAGTCTG 3'
EFG-12:     5' CAGACTCATATGCCAGCTGCCAC 3' e160 (Tyr) ® Ala     EFG-13+EFG-14
EFG-13:     5' GCAGCTGGACGCAGAGTCTGAGC 3'
EFG-14:     5' GCTCAGACTCTGCGTCCAGCTGC 3'

FIG. 11B e161 (Glu) ® Ala    EFG-07+EFG-08
EFG-15:    5' GCTGGACTATGCATCTGAGCCCC 3'
EFG-16:    5' GGGGCTCAGATGCATAGTCCAGC 3'

C'E loop e129 (Tyr) ® Ala    EBS-01+EBS-02
EBS-01:    5' GCTCTCAAGGCATGGTATGAGAAC 3'
EBS-02:    5' GTTCTCATACCATGCCTTGAGAGC 3' e130 (Trp) ® Ala    EBS-03+EBS-04
EBS-03:    5' CTCAAGTACGCATATGAGAACCAC 3'
EBS-04:    5' GTGGTTCTCATATGCGTACTTGAG 3' e131 (Tyr) ® Ala    EBS-01+EBS-02
EBS-05:    5' CAAGTACTGGGCAGAGAACCAC 3'
EBS-06:    5' GTGGTTCTCTGCCCAGTACTTG 3' e132 (Glu) ® Ala    EBS-07+EBS-08
EBS-07:    5' GTACTGGTATGCAAACCACAACATC 3'
EBS-08:    5' GATGTTGTGGTTTGCATACCAGTAC 3' e133 (Asn) ®Ala    EBS-09+EBS-10
EBS-09:    5' CTGGTATGAGGCACACAACATCTCC 3'
EBS-10:    5' GGAGATGTTGTGTGCCTCATACCAG 3' e134 (His) ® Ala    EBS-11+EBS-12
EBS-11:    5' GGTATGAGAACGCAAACATCTCCATTAC 3'
EBS-12:    5' GTAATGGAGATGTTTGCGTTCTCATACC 3'

FIG. 12A  C'-E LOOP
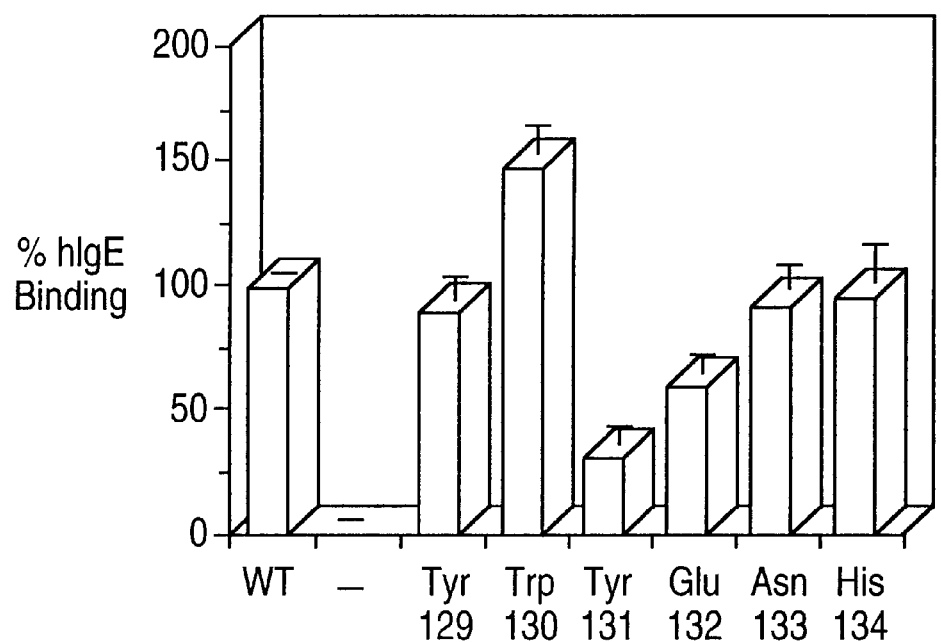
FIG. 12B  F-G LOOP
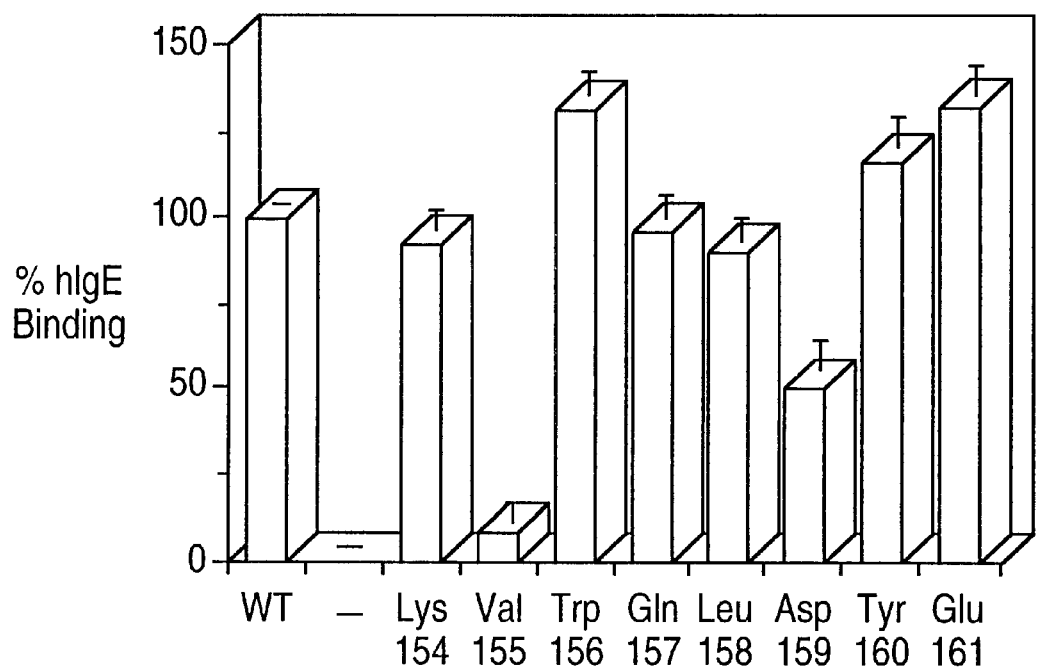

FIG. 14A

```
  *     *     *     *     *     *     *     *     *     *     *     *     *     *
  S  K  P  V  T  I  T  V  Q  V  P  S  M  G  S  S  S  P  X  G  I  I  V  A  V  V  I  A  T  A  V  A  A  I  V    HFc3.47
TCCAAGCCTGTGACCATCACTGTCCAAGTGCCAGCATGGGCAGCTCTTCACCAXTGGGATCATTGTGGCTGTGTCATTGCCGACTGCTGTAGCAGCCATTGTT
::::::::::::::::::::::::::::: :: ::::::::::::::::::: ::::: ::::::::::::::::: ::: :: ::: :::::::::::::
TCCAAGCCTGTCACCATCACTGTCCAAGTCCCAAGTCCAGCAGTCTTTACCAGTATTGACAATTGTGGCTGTCACTGGGATTGCTGTCGCAGCCATTGTT
  S  K  P  V  T  I  T  V  Q  V  P  S  M  G  S  S  S  P  X  G  I  I  V  A  V  V  I  A  V  T  G  I  A  V  A  A  I  V    Beta
```

FIG. 14B

```
  *     *     *     *     *     *     *     *     *
  A  E  N  T  I  T  Y  S  L  L  K  H  P  E  A  L  D  E  E     HFc3.47
GCTGAGAACACGATCACCTACTCACTCCTCAAGCATCCCGAAGCCTTGGATGAAGAA
:::::::::::: ::::: ::::::::::::::::::: :: : :::: :::::::
GCTGAGAACAAAATCACTTATTCACXGCTTATGCXXTCGGAAGCXTCCXAXGAAGAA
  A  E  N  K  I  T  Y  S  X  L  M  X  S  E  X  S  X  E  E    Beta
```

FIG. 15

```
          N  S  G  P  R  N  L  W  L  L  Q  P  L  T  V  L  L  L  A  S
        GAATTCCGGTCCCAGAAACCTGTGGCTGCTTCAACCATTGACAGTTTTGCTGCTGCTGGCTT
          10       20        30        40        50        60        70
                      -1 +1
    A  D  S  Q  A  A  A  P  P  K  A  V  L  K  L  E  P  P  W  I  N  V  L
CTGCAGACAGTCAAGCTGCAGCTCCCCCAAAGGCTGTGCTGAAACTTGAGCCCCCGTGGATCAACGTGCT
          80       90        100       110       120       130       140
    Q  E  D  S  V  T  L  T  Ⓒ  Q  G  A  R  S  P  E  S  D  S  I  Q  W  F
CCAGGAGGACTCTGTGACTCTGACATGCCAGGGGGCTCGCAGCCCTGAGAGCGACTCCATTCAGTGGTTC
         150       160       170       180       190       200  *    210
    H  N  G  N  L  I  P  T  H  T  Q  P  S  Y  R  F  K  A  N  N  N  D  S  G
CACAATGGGAATCTCATTCCCACCCACACGCAGCCCAGCTACAGGTTCAAGGCCAACAACAATGACAGCG
         220       230       240       250       260       270      ↓280
       E  Y  T  Ⓒ  Q  T  G  Q  T  S  L  S  D  P  V  H  L  T  V  L  S  G  Q
GGGAGTACACGTGCCAGACTGGCCAGACCAGCCTCAGCGACCCTGTGCATCTGACTGTGCTTTCCGGTCA
         290       300       310       320       330       340       350
    W  R  K  A  P  G  W  T  W  E  G  P  G  R  M  K  S  V  Y  R  Q  R  F
GTGGAGGAAGGCCCCAGGGTGGACCTGGGAGGGGCCAGGACGGATGAAATCTGTTTACAGACAGAGGTTT
         360       370       380       390    ↓  400       410       420
    A  G  K  S  G  R  G  L  L  T  G  K  M  C ↓*  W  L  V  L  Q  T  P  H  L
GCAGGAAAGAGTGGGCGTGGACTGCTTACTGGGAAGCACTGTTAATGGCTGGTGCTCCAGACCCCTCACC
         430       440       450       460       470       480       490
          E  F  Q  E  G  E  T  I  M  L  R  Ⓒ  H  S  W  K  D  K  P  L  V  K  V
TGGAGTTCCAGGAGGGAGAAACCATCATGCTGAGGTGCCACAGCTGGAAGGACAAGCCTCTGGTCAAGGT
         500       510       520       530       540       550       560
    T  F  F  Q  N  G  K  S  Q  K  F  S  R  L  D  P  T  F  S  I  P  Q  A
CACATTCTTCCAGAATGGAAAATCCCAGAAATTCTCCCGTTTGGATCCCACCTTCTCCATCCCACAAGCA
    *    570       580       590       600       610       620       630
    N  H  S  H  S  G  D  Y  H  Ⓒ  T  G  N  I  G  Y  T  L  F  S  S  K  P  V
AACCACAGTCACAGTGGTGATTACCACTGCACAGGAAACATAGGCTACACGCTGTTCTCATCCAAGCCTG
         640       650       660       670       680       690       700
    T  I  T  V  Q  V  F  S  M  G  S  S  S  P  M  G  I  I  V  A  V  V  I
TGACCATCACTGTCCAAGTGCCCAGCATGGGCAGCTCTTCACCAATGGGGATCATTGTGGCTGTGGTCAT
         710       720       730       740       750       760       770
    A  T  A  V  A  A  I  V  A  A  V  V  A  L  I  Y  C  R  K  K  R  I  S
TGCGACTGCTGTAGCAGCCATTGTTGCTGCTGTAGTGGCCTTGATCTACTGCAGGAAAAAGCGGATTTCA
         780       790       800       810       820       830       840
    A  N  S  T  D  P  V  K  A  A  Q  F  E  P  P  G  R  Q  M  I  A  I  R  K
GCCAATTCCACTGATCCTGTGAAGGCTGCCCAATTTGACCCACCTGGACGTCAAATGATTGCCATCAGAA
         850       860       870       880       890       900       910
    R  Q  L  E  E  T  N  N  D  Y  E  T  A  D  G  G  Y  M  T  L  N  P  R
AGAGACAACTTGAAGAAACCAACAATGACTATGAAACAGCTGACGGCGGCTACATGACTCTGAACCCCAG
         920       930       940       950       960       970       980
    A  P  T  D  D  K  N  I  Y  L  T  L  P  P  N  D  H  V  N  S  N  N  *
GGCACCTACTGACGATAAAAACATCTACCTGACTCTTCCTCCCAACGACCATGTCAACAGTAATAACTAA
         990      1000      1010      1020      1030      1040      1050
```

FIG. 16A

```
        |──→ Leader        |──→ Extracellular
                          -1 +1
HFc3.0      NSGPRNLWLLQPLTVLLLLASADSQAAAPPKAVLKLEPPWINVLQEDSVTLTCQGARSPESDSIQWF
            ***   ****  *  **   ****                  *****        *  ****
Mouse α  MFQNAHSGSQWLLPPLTILLLFAFADRQSAALPKAVVKLDPPWIQVLKEDMVTLMCEQTHNPGNSSTQWF HFc3.0   HNGNLIPTHTQPSYRFKANNNDSGEYTCQTGQTSLSDPVHLTVLSEWLVLQTPHLEFQEGETIMLRCHSW
              *  *     *       ***          * *  *  *                 ****
Mouse α  HNGRSIRSQVQASYTFKATVNDSGEYRCQMEQTRLSDPVDLGVISDWLLLQTPQRVFLEGETITLRCHSW
                                                                    |──→ Transmembrane
HFc3.0   KDKPLVKVTFFQNGKSQKFSRLDPTFSIPQANHSHSGDYHCTGNIGYTLFSSKPVTITVQVPSMGSSSPM
          *                    *        *****  *     *  *      ****   *
Mouse α  RNKLLNRISFFHNEKSVRYHHYKSNFSIPKANHSHSGDYYCKGSLGSTQHQSKEVTITVQDPATTSSISL
                                        |──→ Cytoplasmic
HFc3.0   GIIVAVVIATAVAAIVAAVVALIYCRKKRISANSTDPVKAAQFEPPGRQMIAIRKRQLEETNNDYETADG
                                        *
Mouse α  VWYHTAFSLVMCLLFAVDTGLYFVRRNLQTPREYWRKSLSIRKHQAPQDK HFc3.0   GYMTLNPRAPTDDKNIYLTLPPNDHVNSNN
```

FC RECEPTOR FOR IMMUNOGLOBULIN

CROSS-REFERENCE TO RELATED APPLICATIONS

The present application is a continuation-in-part application of U.S. Ser. No. 07/896,457 filed May, 27, 1992, now U.S. Pat. No. 5,451,669 which is a continuation application of U.S. Ser. No. 07/174,991 filed Mar., 1, 1988, now abandoned which is the National Stage of PCT/AU87/00159, filed 29 May, 1987, the specifications of which are incorporated by reference herein in their entirety. The present application also claims convention priority from Australian provisional application PM88232/94 filed Sep., 16, 1994, which also is incorporated by reference herein in its entirety.

FIELD OF THE INVENTION

The present invention relates, generally, to nucleic acid molecules encoding proteins with Fc receptor activity or Fc receptor-like activity, to complementary nucleic acid sequences encoding the same, proteins with Fc receptor activity, antagonist compounds, pharmaceutical compositions comprising the proteins and antagonist compounds, methods for producing the proteins, methods of treatment of disease using the proteins or antagonist compounds and other aspects.

BACKGROUND OF THE INVENTION

Prior to work carried out by the present inventors the structure and characteristics of cell surface receptors for the Fc portion of immunoglobulin (FcR) were not known to any significant degree. The present inventors were the first to clone and characterize a FcR. It is now known that FcR are expressed on most hematopoietic cells, and through the binding of IgG play a key role in homeostasis of the immune system and host protection against infection. By way of example $Fc_\gamma RII$ is a low affinity receptor for IgG that essentially binds only IgG immune complexes and is expressed on a diverse range of cells such as monocytes, macrophages, neutrophils, eosinophils, platelets and B cells (1-3). $Fc_\gamma RII$ is involved in a number of immune related responses including antibody-dependent cell-mediated cytotoxicity, clearance of immune complexes, release of inflammatory mediators and regulation of antibody production (1-6).

Similarly, Fc receptors for other classes of immunoglobulin also occur. For example the Fc receptor for IgE is present on mast cells, basophils and Langerhans cells.

Both the IgG and the IgE Fc receptors contain an extracellular Ig-interactive region which comprises two Ig-like disulfide bonded extracellular domains of the C2 set (7-11). These domains are structurally conserved in all the Ig-superfamily leukocyte FcR (including $Fc_\gamma RI$, $Fc_\gamma RIII$, $Fc_\epsilon RI$ and $Fc\alpha RI$) and presumably represents an Ig-interactive motif (12-16). In previous studies the inventors identified the IgG binding region of human $Fc_\gamma RII$ (17, 18). Chimeric $Fc_\gamma RII/Fc_\epsilon RI$ α chain receptors were used to demonstrate that the second extracellular domain of $Fc_\gamma RII$ was responsible for the binding of IgG, with a direct binding region located between residues $Asn^{154}$ to $Ser^{61}$. Molecular modelling of $Fc_\gamma RII$ domain 2 predicted a structure comprising 7β, strands (A, B, C, C', E, F, G) forming two antiparallel β sheets (containing the ACFG and BC'E strands respectively), stabilized by a disulfide bond between strands B and F and a core of hydrophobic residues (20). The $Asn_{154}$ to $Ser^{161}$ binding region was shown to encompass an exposed loop region (the F-G loop) at the interface of domains 1 and 2.

In work leading up to the present invention, the inventors cloned and characterized the genes encoding mouse and human Fc receptors. They also surprisingly discovered that alteration of amino acid residues in the Fc receptors lead to altered affinities for immunoglobulin.

SUMMARY OF THE INVENTION

It is an object of the present invention to provide an understanding of the function and structure of Fc receptors to enable the development of reagents and pharmaceutical products useful in diagnosis and methods of treatment of diseases involving Fc receptors.

In one aspect the present invention relates to a nucleotide sequence encoding, or a complementary sequence encoding, a protein with Fc receptor activity.

In another aspect the present invention relates to a nucleotide sequence encoding an Fc receptor-like protein comprising an altered ability to bind immunoglobulin wherein said ability is brought about by alteration of one or more amino acid residues which affect immunoglobulin binding ability.

The present invention also relates to host organisms transformed with the vectors mentioned above.

In another aspect, the present invention relates to an isolated preparation of a protein with Fc receptor activity and to mutants, variants and derivatives thereof.

In another aspect the present invention relates to an Fc receptor-like protein with an altered ability to bind immunoglobulin wherein said altered ability is brought about by alteration of one or more amino acid residues which affect immunoglobulin binding.

In another aspect the present invention relates to antagonist compounds which interfere with amino acid residues in Fc receptors which are involved in binding immunoglobulin.

In another aspect the present invention contemplates pharmaceutical compositions containing as an active ingredient the Fc receptor-like protein or the antagonist compounds described above, depending on the condition to be treated, together with a pharmaceutically appropriate carrier or diluent.

The invention further extends to a method of producing the nucleic acid molecules of the invention comprising mutating a nucleic acid encoding an Fc receptor such that one or more of the amino acids which affect immunoglobulin binding are altered resulting in an encoded protein which has an altered ability to bind immunoglobulin.

The invention also relates to a method of producing the Fc receptor-like protein of the invention by recombinant means.

In another aspect the invention relates to a method of determining the presence of immunoglobulin in a sample said method comprising contacting said sample with a protein with Fc receptor activity of the present invention, for a time and under conditions sufficient to allow the protein and any immunoglobulin present in said sample to bind and detecting said bound protein-immunoglobulin.

Another aspect of the invention relates to a kit for detecting immunoglobulin including immune complexes in a sample, said kit comprising in compartmentalized form a first compartment adapted to receive a Fc receptor-like protein and at least one other compartment adapted to contain a detector means.

In another aspect the present invention provides a method of detecting immune complex in a sample comprising contacting said sample with a protein with Fc receptor activity which is specific for IgG having enhanced immunoglobulin binding activity, for a time and under conditions sufficient for any complex present in the sample and the protein to form a further complex and detecting said further complex.

In yet another aspect the present invention relates to a method of removing immunoglobulin from a body fluid comprising taking body fluid from a patient, contacting the body fluid with a protein with Fc receptor activity or a Fc receptor-like protein with an enhanced ability to bind immunoglobulin, for a time and under conditions sufficient to allow the protein or Fc receptor to bind said immunoglobulin, removing said bound immunoglobulin from the body fluid and replacing said body fluid in the patient.

In another aspect the present invention relates to a method of treatment of disease where the disease involves immune complexes or antigen-antibody interactions, said method comprising administering an effective amount of the protein with Fc receptor activity or an antagonist compound of the invention to a subject.

BRIEF DESCRIPTION OF THE FIGURES

FIG. 1. Nucleotide and deduced amino acid sequence (SEQ. ID. NOS:80–81) of the mouse FcR encoded by pFc113. Amino acids are numbered above the line in decades commencing at the amino terminal Thr deduced by protein sequencing (Hibbs et al, 1986). Nucleotides are numbered at the end of the line and the 5' and 3' untranslated regions are shown in closed up type. The signal sequence is numbered from residue −29 to −1 and the transmembrane region (Tm) is underlined by a broken line. The sequences underlined with a solid line correspond to sequences identical to the amino terminal sequence (NH2) and to amino acid sequence of peptides (L9, V17, 2V16, 2V8, CNBR, L5, L3, L4, V10, V11) isolated from the immunopurified FcR (Hibbs et al., 1986). Other notation is as follows: o, first Cys in each domain; ●, second Cys in each domain *; N-linked glycosylation sites. The nucleotide sequence of pFc24 is embodied within the cDNA insert of pFc113 from nucleotides 61 to 1023.

FIG. 2. Nucleotide and predicted amino acid sequence (SEQ. ID. NOS:82–83) of the human FcR encoded by HFc3.0. Nucleotides are numbered every decade and the translated sequence is found above the nucleotide sequence. Amino acids are numbered above the line and number 1 indicates the N-terminal residue. The incomplete signal sequence is underlined by a broken line to residue −1. The two glycosylation sites are marked by stars and the single hydrophobic transmembrane region is underlined by a solid line. Cysteine residues involved in disulfide bonding are circled.

FIG. 3A: blood clearance of $^{125}$I-rsFcγRII; % initial injected dose is shown on the y-axis and time (hours) on the x-axis; FIG. 3B: urine $^{125}$I-rsFcγRII levels, expressed as % initial injected dose/ml of urine, at 15 minutes (n=4) and one hour (n=2); and FIG. 3C: biodistribution in various organs showing the % initial injected dose/g of tissue on the y-axis. Error bars=SE.

FIG. 5A–5B. IgG1 binding by FcγRII 154–161 Alanine substitution mutants. Percentage wild-type binding of dimeric human IgG1(FIG. 5A), or dimeric mouse IgG1 (FIG. 5B). COS cells were transiently transfected with expression constructs for wild-type FcγRII, vector alone, or FcγRII point mutants—where each residue in the 154–161 binding region of FcγRII was replaced with alanine. Forty eight hours post transfection, cells were tested for their capacity to bind $I^{125}$ labelled dimeric human IgG1 in a direct binding radio-immunoassay, performed with saturating amounts of $I^{125}$ dimeric human or mouse IgG1 (2 ug/ml). Results are expressed as % wild-type FcγRII binding following correction for equivalent levels of cell surface expression. The mean and standard errors calculated from three individual experiments for human mouse IgG1 binding are shown, weight, wild-type FcγRII; mock, vector alone; mutant, Alanine point mutants.

FIGS. 6A–6B (SEQ. ID. NOS:84–94). Sequence alignment of CD4-2 versus FcγRII domain 2 and FcεRI domain 2 and other FcR domains.

FIGS. 7A–7D. IgG complex binding of chimeric Fc receptors. COS-7 cell monolayers were transfected with chimeric cDNA constructs: D1εD2γ (FIG. 7A), γ109–116ε (FIG. 7B), γ130–135ε (FIG. 7C), or FC$_ε$RI (FIG. 7D). The binding of IgG immune complexes was assessed directly on the monolayers by EA rosetting using mouse IgG1 sensitized erythrocytes.

FIGS. 9A–9D. Human IgG1 -dimer binding by Fc$_γ$RIIa alanine point mutants. Radiolabelled dimeric human IgG1 was titrated on COS-7 cells transfected with wild-type Fc$_γ$RIIa or Fc$_γ$RIIa containing alanine point mutations, FIG. 9A: B–C loop mutants, Lys$^{113}$-Ala (□), Pro$^{114}$-Ala (▲), Leu$^{115}$ -Ala (●), Val$^{116}$-Ala (○); FIG. 9B: C'-E loop mutants, Phe$^{129}$-Ala (−), Ser$^{130}$-Ala (◇), Arg/His$^{131}$-Ala (♦), Leu$^{132}$-Ala (X), Asp$^{133}$-Ala (■), Pro$^{134}$-Ala (△). Comparison of the levels of human IgG1 dimer binding to Fc$_γ$RII mutants relative to wild-type Fc$_γ$RIIa, FIG. 9C: B–C loop mutants, FIG. 9D: C'-E loop mutants. The binding of wild-type Fc$_γ$RIIa taken as 100% and mock transfected cells as 0% binding. Results are expressed as ±S.E. To control for variable receptor expression between the mutant Fc$_γ$RII COS-7 cell transfectants, levels of expression were determined using a radiolabelled monoclonal anti-Fc$_γ$RII antibody 8.2, and dimer binding normalized to that seen for wild-type Fc$_γ$RII. Typical levels of 8.2 binding in cpm ±S.E: WT Fc$_γ$RII 95279; Lys$^{113}$-Ala 71660; Pro$^{114}$-Ala 61636; Leu$^{115}$-Ala 44696; Val$^{116}$-Ala; Phe$^{129}$-Ala 74707; Ser$^{130}$-Ala 139802; Arg/His$^{131}$-Ala 140475; Leu$^{132}$-Ala 121096; Asp$^{133}$-Ala 100149; Pro134-Ala 172047.

FIGS. 11A–11B. Oligonucleotides (SEQ. ID. NOS:95–122) used in SOE-PCR of Example 6.

FIGS. 12A–12B. Histogram showing the effect of mutations on IgE receptor binding immunoglobulin.

FIGS. 14A–14B (SEQ. ID. NOS:123–130). Partial nucleotide sequence and predicted amino acid sequence for HFc3.47 cDNA derived from two non-overlapping HFc3.47 fragments and identification of homologous regions in the beta (1 or 2) FcR of the mouse. The HFc3.47 nucleotide and amino acid sequences are shown as the upper sequences in FIG. 14A and the lower sequences in FIG. 14B. Diamonds indicate nucleotide identities where as asterisks indicate amino acid identities. An "X" in the sequence indicates an unknown residue.

FIG. 15 Nucleotide and predicted amino acid sequence of the human FcR encoded by HFc3.1 (SEQ ID NOs: 131 and 32, respectively). Nucleotides are numbered every decade and the translated sequence is found above the nucleotide sequence. Amino acids are numbered above the line and number 1 indicates the N-terminal residue. The incomplete signal sequence is underlined by a broken line to residue –1. The two glycosylation sites are marked by stars and the single hydrophobic transmembrane region is underlined by a solid line. Cysteine residues involved in disulfide bonding are circled. The "intron-like" sequence is located between the vertical arrows.

FIG. 16A–16C Homology of the human FcR encoded by Hfc3.0 cDNA with the mouse alpha and beta1 FcR (SEQ ID NOs:133 and 134, respectively). Alignment of the nucleotides of the human FcR with both mouse alpha (A) and beta1 (B) FcR. Amino acid residues common to the human FcR encoded by HFc3.0 and the alpha FcR (A) or beta1 (B) are shown by asterisks. The human (HFc3.0) mouse alpha or beta FcR leader sequence, extracellular domain, transmembrane and cytoplasmic domains are indicated by the sequences between the vertical arrows. The cysteine (C) residues within the extracellular domains (involved in S—S bonds) are identified by the solid circles.

DETAILED DESCRIPTION OF PREFERRED EMBODIMENTS

Figure 3A:
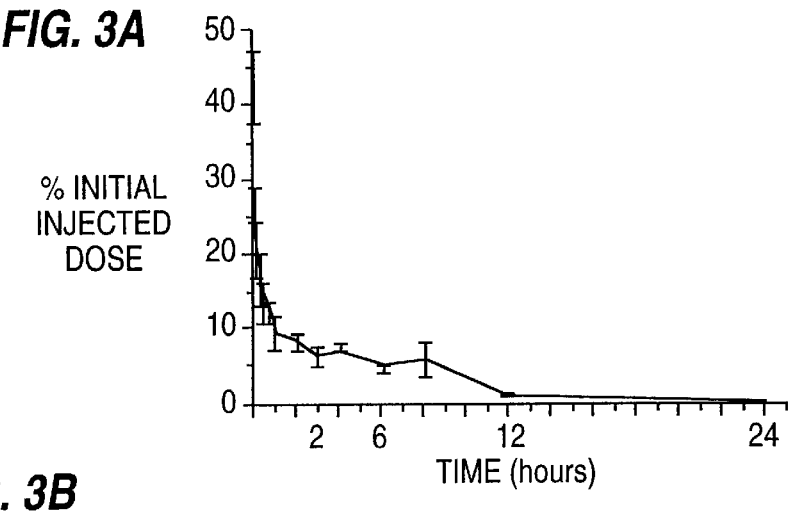
FIGS. 3A–3C. Blood clearance and biodistribution of $^{125}$I-rsFcγRII.

In one aspect the present invention relates to a nucleic acid molecule encoding, or a complementary sequence according, a protein with Fc receptor activity.

The phrase "nucleic acid molecule" means a molecule comprised of purines or pyrimidines, natural or synthetic including DNA and/or RNA. The molecule may be single or double stranded, linear or circular in form. The nucleotide sequence of the molecule may be derived from natural sources such as by direct cloning methods or may be synthetically constructed. The natural source may be that of any species, preferably mammalian such as human, murine, rat, porcine, equine, bovine, ovine caprine, etc. The phrase "derived from" means that the sequences originates from the particular species mentioned but is not limited to being directly derived therefrom. In addition the molecule may encode proteins which represent hybrids between species such as mouse/human, rat/human or humanized proteins with Fc receptor activity with appropriately mutated amino acids to minimize antagonistic-immune responses.

The phrase "a protein" means a peptide, polypeptide or protein comprised of amino acids linked by peptide bonds.

The phrase "with Fc receptor activity" means a protein as defined above which is able to bind immunoglobulin. This includes a protein which has Fc receptor-like activity, which means a protein which is able to bind the immunoglobulin to at least some degree. The immunoglobulin may be IgG, IgE, IgA, IgM or IgD. The Fc receptor activity of the protein may be similar to that of a native Fc receptor, or may be enhanced or reduced compared to that of a native Fc receptor.

The above statement includes the nucleotide, gene, c DNA clone or vector for same adapted to encode or to produce a material adapted to encode for the receptor or a fragment thereof mentioned in U.S. Ser. No. 896,457.

The nucleic acid molecule of the present invention (or its complementary form) also extends to functional mutants, and derivatives of the nucleic acid molecule encoding a protein with Fc receptor activity.

The term "mutant" means a naturally occurring or artificially induced mutant encoding a protein with Fc receptor activity or sequences complementary to that encoding protein. The mutant nucleotide sequence may be a silent mutation or result in an encoded protein which has amino acid insertions, deletions or substitutions in its amino acid sequence composed to the native forms of the protein.

The term "variant" includes nucleic acid molecules encoding isoforms of the protein having Fc receptor activity, which variants may be artificially created or naturally occurring.

The amino acid variants referred to above may readily be made using peptide synthetic techniques well known in the art, such as solid phase peptide synthesis and the like, or by recombinant DNA manipulations. Techniques for making substitution mutations at predetermined sites in DNA having known or partially known sequence are well known and include, for example, M13 mutagenesis. The manipulation of DNA sequence to produce variant proteins which manifest as substitutional, insertional or deletional variants are conveniently described, for example, in Sambrook et al (1989).

The term "derivatives" refers to a nucleic acid molecule which encodes protein having Fc receptor activity which molecule is related to, but different from, native forms of the protein. This includes nucleic acids encoding fragments of the native protein. The term also includes parts of the nucleic acid molecule of the invention including parts of its complementary form. The part may encode a fragment of the protein having Fc receptor activity or may be non-coding. Such part nucleic acid molecule may be useful as an oligonucleotide probe, a primer to use in polymerase chain reaction, including various mutagenesis techniques or for the generation of various antisense molecules.

Amino acid insertional derivatives of the encoded protein with Fc receptor activity include amino and/or carboxyl terminal fusions as well as intra-sequence insertions of single or multiple amino acids. Insertional amino acid sequence variants are those in which one or more amino acid residues are introduced into a predetermined site in the protein although random insertion is also possible with suitable screening of the resulting product. Deletional variants are characterized by the removal of one or more amino acids from the sequence. Substitutional amino acid variants are those in which at least one residue in the sequence has been removed and a different residue inserted in its place. Typical substitutions are those made in accordance with Table 1.

Where the encoded protein is derivatized by amino acid substitution, the amino acids are generally replaced by other amino acids having like properties, such as hydrophobicity, hydropholicity, electronegativity, bulky side chains and the like. Amino acid substitutions are typically of single residues. Amino acid insertions will usually be in the order of about 1–10 amino acid residues and deletions will range from about 1–20 residues.

Other examples of recombinant or synthetic mutants and derivatives encoded by the nucleic acid molecules of the present invention include single or multiple substitutions, deletions and/or additions of any molecule associated with the enzyme such as carbohydrates, lipids and/or proteins or polypeptides.

Typical substitutions are those made in accordance with Table 1.

TABLE 1

Suitable residues for amino acid substitutions

| Original Residue | Exemplary Substitutions |
|

GAA AAA TCC GTG AGG TAT CAT CAC TAC AGT AGT
AAT TTC TCT ATC CCC AAA GCC AAC CAC AGT CAC
AGT GGG GAC TAC TAC TGC, or (h) (SEQ. ID. NO:8) TTA CCA GTA TTG ACA ATT GTG
GCT GCT GTC ACT GGG ATT GCT GTC GCA GCC ATT
GTF ATT ATC CTA GTA TCC TTG GTC TAT CTC, or (i) (SEQ. ID. NO:9) AAG AAA AAG CAG GTT CCA
GCT CTC CCA GGA AAC CCT GAT CAC AGG GAA
ATG GGA GAA ACC CTT CCA GAG GAA GTA GGT
GAG TAC AGA CAG CCC TCT GGG GGC TCA GTG
CCT GTC AGC CCA GGG CCT CCA TCT GGA CTG
GAG CCA ACA AGC AGC AGC CCA TAC AAT CCT CCT
GAT CTG GAA GAA GCT CCC AAA ACT GAG GCT
GAG AAC ACG ATC ACC TAC TCA CTC CTC AAG CAT
CCC GAA GCC TTG GAT GAA GAA ACA GAG CAT
GAT TAC CAA AAC CAC ATT TAG, or (j) (SEQ. ID. NO:10) AAT TCC GGT CCC AGA AAC
CTG TGG CTG CTT CAA CCA TTG ACA GTT TTG CTG
CTG CTG GCT TCT GCA GAC AGT CAA GCT GCA, or (k) (SEQ. ID. NO:11) TGC CAG GGG GCT CGC AGC
CCT GAG AGC GAC TCC ATT CAG TGG TTC CAC AAT
GGG AAT CTC ATT CCC ACC CAC ACG CAG CCC
AGC TAC AGG TTC AAG GCC AAC AAC AAT GAC
AGC GGG GAG TAC ACG TGC, or (l) (SEQ. ID. NO:12) TGC CAC AGC TGG AAG GAC
AAG CCT CTG GTC AAG GTC ACA TTC TTC CAG AAT
GGA AAA TCC CAG AAA TTC TCC CGT TTG GAT CCC
ACC TTC TCC ATC CCA CAA GCA AAC CAC AGT CAC
AGT GGT GAT TAC CAC TGC, or (m) (SEQ. ID. NO:13) TCA CCA ATG GGG ATC ATT
GTG GCT GTG GTC ATT GCT ACT GCT GTA GCA GCC
ATT GTT GCT GCT GTA GTG GCC TTG ATC TAC TGC,
or (n) (SEQ. ID. NO:14) AGG AAA AAG CGG ATT TCA
GCC AAT TCC ACT GAT CCT GTG AAG GCT GCC CAA
TTT GAG CCA CCT GGA CGT CAA ATG ATT GCC ATC
AGA AAG AGA CAA CTT GAA GAA ACC AAC AAT
GAC TAT GAA ACA GCT GAC GGC GGC TAC ATG ACT
CTG AAC CCC AGG GCA CCT ACT GAC GAT AAA
AAC ATC TAC CTG ACT CTT CCT CCC AAC GAC CAT
GTC AAC, or (o) (SEQ. ID. NO:15) ACA GGA AAC ATA GGC TAC
ACG CTG TTC TCA TCC AAG CCT GTG ACC ATC ACT
GTC CAA GTG CCC AGC ATG GGC AGC TCT or a variant thereof encoding a polypeptide capable of binding the Fc region of immunoglobulin.

More preferably the polynucleotide encodes the extracellular domain of the human Fc receptor and the human Fc receptor binding sites.

Figure 2:
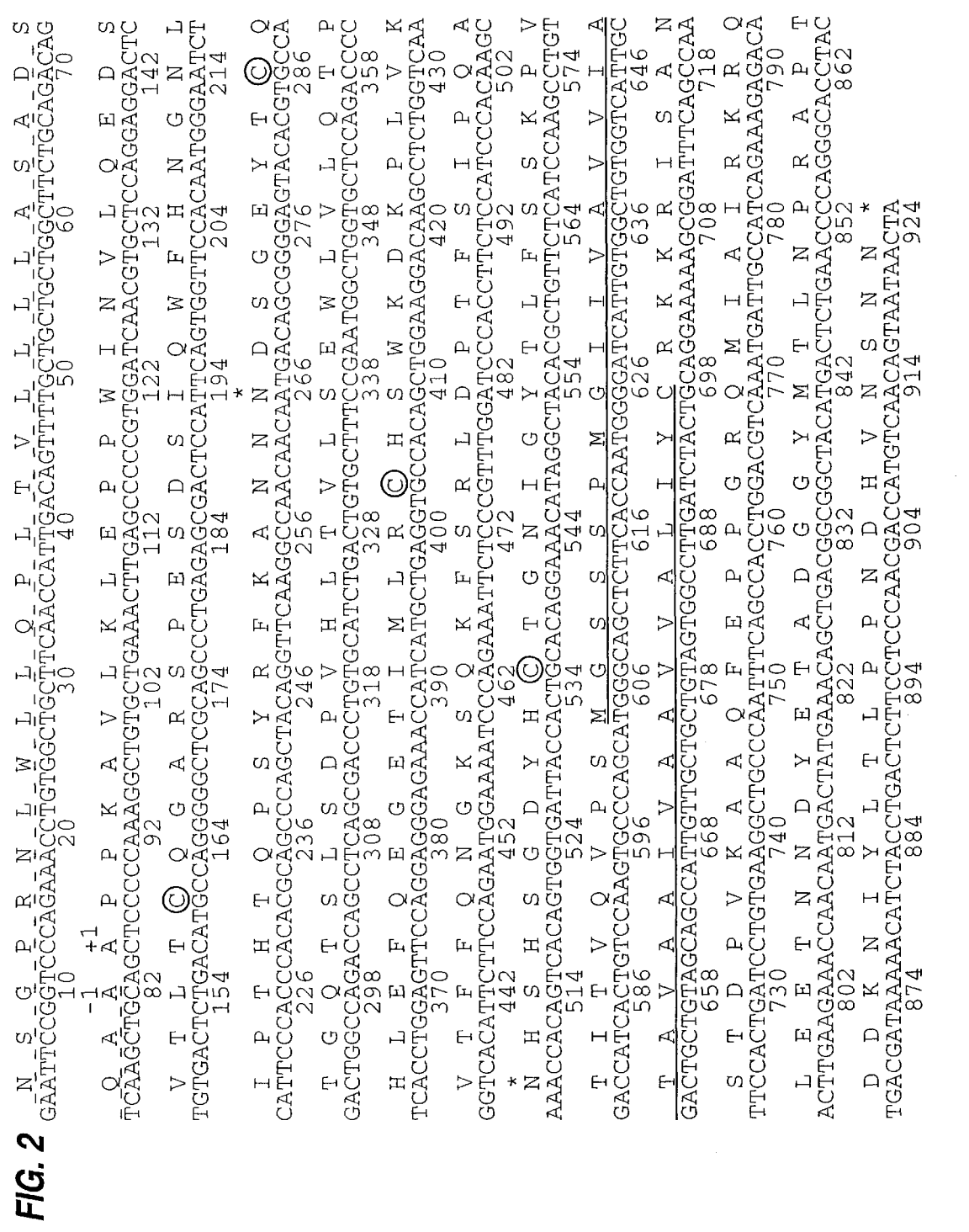

Still more preferably the polynucleotide comprises nucleotides 84 through 924, or 84 through 601 of FIG. 2 (SEQ. ID. NO:82) or a mutant, variant or derivative thereof which is capable of binding the Fc region of human immunoglobulin.

In another aspect the present invention relates to a nucleic acid molecule encoding an Fc receptor-like protein comprising an altered ability to bind immunoglobulin wherein said ability is brought about by alteration of one or more amino acid residues which affect immunoglobulin binding ability.

The phrases "nucleic acid molecule" and "Fc receptor-like protein" have the meanings given earlier.

The phrase "an altered ability to bind immunoglobulin" means that the molecule has an immunoglobulin binding activity different to that of one or more native Fc receptors. This includes the ability of the protein to bind one form of immunoglobulin compared to another form of immunoglobulin i.e. where the protein has an altered ability to bind immune complexes, aggregates, dimeric or monomeric immunoglobulin compared to a native Fc receptor. The activity of the protein may be increased or decreased compared to a native Fc receptor for a given immunoglobulin class.

The phrase "alteration of one or more amino acid residues which affect immunoglobulin binding ability" means that the comparable amino acid residue or region of amino acid residues, implicated in immunoglobulin binding in a native Fc receptor are changed in the Fc receptor-like protein. The amino acids implicated in immunoglobulin binding may function directly in immunoglobulin binding or may be involved indirectly such as by maintaining the structural integrity of the receptor so that binding can occur. The change(s) may be the result of insertion, deletion or substitution.

Those skilled in the art will know which techniques may be used to alter the amino acids encoded by a nucleic acid in order to produce a nucleic acid molecule in accordance with the invention. The nucleic acid molecule may be made by site mutagenesis of DNA encoding native Fc receptor, splice extension overlap PCR, de novo synthesis, etc.

Preferably the nucleic acid molecule encodes a mutant, derivative or variant of a native Fc receptor as described earlier.

Preferably the nucleic acid molecule encodes an Fc receptor like protein which has enhanced ability to bind IgG or IgE. The phrase "enhanced ability to bind immunoglobulin" means that the molecule has an immunoglobulin binding activity higher than, or increased compared to, a native Fc receptor in a given class.

More preferably the nucleic acid molecule encodes an Fc receptor-like protein with an enhanced ability to bind IgG. The molecule comprises codons resulting in one or more altered amino acids in the A/B, C/C' or E/F loops of the first domain or F/G, B/C or C'/E loops of the second domain or the G/A strand that connects the two domains. The loops referred to hereafter are the loops identified in the putative 3-D structures or their equivalents for the receptors discussed earlier and identified in the Examples. It also includes equivalent loop structures in other native Fc receptors. In addition all of the amino acid residue positions discussed herein are relative to the amino acid sequences of $Fc_\gamma RII$ or $Fc_\epsilon RI$.

The loops of FcγRII are as follows:

| Domain 1 | A/B | $Glu^{10}$—$Ser^{21}$ |
|---|---|---|
| | C/C' | $Asn^{42}$—$Ile^{46}$ |
| | E/F | $Asn^{59}$—$Asp^{62}$ |
| Domain 2 | B/C | $Ser^{109}$—$Val^{116}$ |
| | C'/E | $Phe^{129}$—$Pro^{134}$ |
| | F/G | $Asn^{154}$—$Ser^{161}$ |
| G/A strand | | $Val^{79}$—$Pro^{93}$ |
| Loops for FcεRI are: | | |
| Domain 1 | A/B | $Asn^{10}$—$Asn^{21}$ |
| | C/C' | $Asn^{42}$—$Leu^{45}$ |
| | E/F | $Lys^{59}$—$Glu^{61}$ |
| Domain 2 | B/C | $Trp^{110}$—$Lys^{117}$ |
| | C'/E | $Tyr^{129}$—$His^{134}$ |
| | F/G | $Lys^{154}$—$Glu^{161}$ |
| G/A strand | | $Val^{79}$—$Ser^{93}$ |

Still more preferably the codons result in altered amino acids at positions 133, 134, 158, 159, 160, and/or 161 of the protein. Most preferably the altered amino acids comprise alanine, glycine, serine, asparagine or small synthetic neutrally charged amino acids. Most preferably the codon specifies the amino acid alanine.

Still more preferably the nucleic acid molecule comprises a cDNA encoding Fc$_\gamma$RII with the codon for Asp$^{133}$ and/or Pro$^{134}$ and/or Leu$^{159}$ and/or Phe$^{160}$ and/or Ser$^{161}$ specifying alanine. Even more preferably the nucleic acid molecule is Asp$^{133}$-Ala or Pro$^{134}$-Ala or Leu$^{159}$-Ala, or Phe$^{160}$-Ala and/or Ser$^{161}$-Ala as described in the Examples.

Alternatively more preferably the nucleic acid molecule encodes an Fc receptor-like protein with an enhanced ability to bind IgE. The molecule comprises codons resulting in one or more altered amino acids in the A/B, C/C' and/or E/F loops of the first domain or the F/G, C'/E and/or B/C loops of the second domain or the G/A strand.

Still more preferably the codons result in altered amino acids at positions 130, 156, 160 and/or 161.

Still more preferably the nucleic acid molecule comprises a cDNA encoding Fc$_\epsilon$RI with the codon for Trp$^{130}$, Trp$^{156}$, Tyr$^{160}$ and/or Glu$^{161}$ specifying alanine. Even more preferably the nucleic acid molecule is Trp$^{130}$-Ala, Asp$^{159}$-Ala, Tyr$^{160}$-Ala or Glu$^{161}$-Ala as described in the Examples.

Alternatively preferably the nucleic acid molecule encodes an Fc receptor like protein which has reduced ability to bind IgG or IgE. The phrase “reduced ability” has the same meaning as given earlier.

The amino acid alterations specified by the codons will generally be amino acids with different chemical characteristics such as that described earlier.

More preferably where the nucleic acid molecule encodes an Fc receptor-like protein with a reduced ability to bind IgG the molecule comprises codons which result in one or more altered amino acids in the A/B, C/C' and/or E/F loops in the first domain or the F/G, B/C and/or C'/E loops in the second domain or the G/A strand.

Still more preferably the codons result in altered amino acids at positions 10–21, 42–48, 59–62, 113, 114, 115, 116, 129, 131 155 and/or 156.

Even more preferably the codons for the first domain of $Fc_{\gamma}RII$ are removed or replaced by those for a receptor for another immunoglobulin.

Alternatively even more preferably the codons for $Lys^{113}$, $Pro^{114}$, $Leu^{115}$, $Val^{116}$, $Phe^{129}$, $Arg/His^{131}$ and $Ile^{155}$ and/or $Gly^{156}$ are replaced by the codon for alanine in the $Fc_{\gamma}RII$. Still more preferably the nucleic acid molecule comprises the constructs D1 D1 z,900 D2␣$Lys^{113}$-Ala, $Pro^{114}$-Ala, $Leu^{115}$-Ala, $Val^{116}$-Ala, $Phe^{129}$-Ala, $Arg/His^{131}$-Ala, $Ile^{155}$-Ala and/or $Gly^{156}$-Ala described in the Examples.

Alternatively more preferably where the nucleic acid molecule encodes an Fc receptor-like protein with a reduced ability to bind IgE the molecule comprises codons which result in one or more altered amino acids in the A/B, C/C' and/or E/F loops in the first domain or the F/G, C'/E and/or B/C loops in the second domain or the G/A strand.

Still more preferably the codons result in altered amino acids at positions 10–21, 42–48, 59–62, 125 to 135, 129, 129 to 131, 131, 132, 135, 155, 158, 159.

Even more preferably the codons for the first domains of $Fc_{\epsilon}RI$ are removed or replaced by those for a receptor for another immunoglobulin.

Alternatively even more preferably the codons for $Tyr^{129}$, $Tyr^{131}$, $Glu^{132}$, $Val^{155}$, $Leu^{158}$ and/or $Asp^{159}$ is/are replaced by the codon for alanine in $Fc_{\epsilon}RI$. Still more preferably the nucleic acid molecule of the invention comprises the constructs γ109–116ϵ, γ130–135ϵ, $Tyr^{131}$-Ala, $Glu^{132}$-Ala, $Val^{155}$-Ala, $Leu^{158}$-Ala and $Asp^{159}$-Ala as described in the Examples.

The invention also extends to the nucleic acid molecules used as primers to produce the nucleic acid molecule of the invention. The primers described in the Examples are particularly preferred.

The nucleic acid molecule of the invention may be present in an expression vector where it is desired to obtain expression of the nucleic acid molecule. The expression vector chosen depends on the host cell in which it is intended to produce the protein encoded by the nucleic acid molecule.

Thus the present invention also relates to host organisms transformed with the vectors mentioned above.

Expression in prokaryotes may be carried out using organisms known from the prior art, especially *E. coli*. The nucleic acid molecule of the invention may be expressed as fusion polypeptides or as intact, native polypeptides.

Fusion proteins may advantageously be produced in large quantities. They are generally more stable than the native polypeptide and are easy to purify. The expression of these fusion proteins can be controlled by normal *E. coli* DNA sequences.

For example, the DNA molecule according to the invention can be cloned and expressed as lacZ fusion genes. The person skilled in the art has a variety of vector systems available for this purpose, e.g. the pUR-vector series (R üther, U. and Müller-Hill, B. (1983), EMBO J. 2, 1791). The bacteriophage promoter $\lambda P_R$ may also be used, in the form of the vectors pEX-1 to -3, for expressing large amounts of Cro-β-galactosidase fusion protein (Stanley, K. K. and Luzio, J. P. (1984) EMBO J. 3, 1429). Analogously, the tac promoter which can be induced with IPTG can also be used, for example in the form of the pROK-vector series (CLONTECH Laboratories).

The prerequisite for producing intact polypeptides using *E. coli* is the use of a strong, regulatable promoter and an effective ribosome binding site. Promoters which may be used for this purpose include the temperature sensitive bacteriophage $\lambda p_L$-promoter, the tac-promoter inducible with IPTG or the T7-promoter.

Numerous plasmids with suitable promoter structures and efficient ribosome binding sites have been described, such as for example pKC30 ($\lambda P_L$; Shimatake and Rosenberg (1981) Nature 292, 128, pKK173-3 (tac, Amann and Brosius (1985) Gene 40, 183) or pET-3 (T7-promoter (Studier and Moffat (1986) J. Mol. Biol. 189, 113).

A number of other vector systems for expressing the nucleic acid molecule according to the invention in *E. coli* are known from the prior art and are described for example in Sambrook et al (1989).

Suitable *E. coli* strains which are specifically tailored to the expression vector in question are known to those skilled in the art (Sambrook et al. (1989)).

The experimental performance of the cloning experiments, the expression of the polypeptides in *E. coli* and the working up and purification of the polypeptides are known and are described for example in Sambrook et al. (1989).

Suitable eukaryotic hosts include but are not limited to yeast, such as Saccharomyces and animal cells in culture such as COS, VERO, HeLa, mouse C127, Chinese hamster ovary (CHO), WI-38, BHK, MDCK, and insect cell lines. Such recombinant techniques have now become well known and are described in *Methods in Enzymology,* (Academic Press) Volumes 65 and 69 (1979), 100 and 101 (1983), and the references cited therein. An extensive technical discussion embodying most commonly used recombinant DNA methodologies can be found in Sambrook et al. (1989).

After the recombinant product is produced it is desirable to recover the product. If the product is exported by the cell producing it, the product can be recovered directly from the cell culture medium. If the product is retained intracellularly, the cells must be physically disrupted by mechanical, chemical or biological means in order to obtain the intracellular product.

The purification protocol of the protein should not only provide a protein product that is essentially free of other proteins, but also eliminate or reduce to acceptable levels other host cell contaminants, DNA, RNA, potential pyrogens and the like.

As mentioned above, a variety of host cells may be used for the production of the protein with Fc receptor activity of the invention. The choice of a particular host cell is well within the ability of the ordinary skilled worker taking into account, inter alia, the nature of the protein, its rate of synthesis, its rate of decay and the characteristics of the recombinant vector directing the expression of the receptor. The choice of the host cell expression system dictates to a large extent the nature of the cell culture procedures to be employed. The selection of a particular mode of production be it batch or continuous, spinner or air lift, liquid or immobilized can be made once the expression system has been selected. Accordingly, fluidized bed bioreactors, hollow fibre bioreactors, roller bottle cultures, or stirred tank bioreactors, with or without cell microcarrier may variously be employed. The criteria for such selection are appreciated in the cell culture art.

In another aspect, the present invention relates to an isolated preparation of a protein with Fc receptor activity and to functional mutants, variants and derivatives thereof.

The term "isolated preparation" has the same meaning as the terms "biologically pure" and "isolated form" as described above. The terms "mutants, variants and derivatives" have the same meaning as given above when applied to proteins.

Preferably the purity of the protein is at least 40% pure, preferably at least 50% pure, preferably at least 60% pure, more preferably at least 75% pure, even more preferably at least 85% pure and still more preferably at least 95% pure as determined by activity, weight, amino acid similarity, antibody reactivity or other convenient means.

The protein preparation of the present invention may be made isolated from natural sources, be made synthetically or produced by recombinant means. Preferably the protein is produced by recombinant means.

Preferably the protein has the amino acid sequence corresponding to that of FIGS. 1, 2 or HFc 3.0, HFc 3.1, HFc 3.47, pFc24 or pFc113 or a mutant, variant or derivative thereof.

In a particularly preferred aspect the invention comprises a soluble protein with Fc receptor activity. This protein lacks the transmembrane and cytoplasmic regions of the native Fc receptor for any form of immunoglobulin.

Preferably the soluble proteins are those encoded by the nucleic acid molecules described above.

In another aspect the invention relates to an isolated polypeptide comprising a receptor for the Fc portion of immunoglobulin, the receptor exhibiting an ability to bind the Fc portion of mouse and human immunoglobulin.

Preferably the polypeptide has a size of about 40–70 kilodaltons and comprising about 280 to 301 amino acids including two substantially regularly spaced pairs of Cys residues and two or four potential N-linked glycosylation sites.

Still more preferably the polypeptide comprises the amino acid sequences (a) (SEQ. ID. NO.:16) Met Leu Leu Trp Thr Ala Val Leu Asn Leu Ala Ala Gly Thr His Asp Leu Pro Lys Ala Val Val Lys Leu Glu Pro Pro Trp Ile, (b) (SEQ. ID. NO.:17) Glu Gln Thr Arg Leu Ser Asp Pro Val Asp Leu Gly Val Ile, and (c) (SEQ. ID. NO.:18) Lys Gly Ser Leu Gly Arg Thr Leu His Gln Ser Lys Pro Val Thr Ile Thr Val Gln Gly Pro Lys, and (d) (SEQ. ID. NO.:19) Glu Ala Glu Asn Thr Ile Thr Tyr Ser Leu Leu Lys His Pro Glu Ala Leu Asp Glu Glu Thr Glu His, or (e) (SEQ. ID. NO.:20)Met Glu Ser Asn Trp Thr Val His Val Phe Ser Arg Thr Leu Cys His Met Leu Leu Trp Thr Ala Val Leu Asn Leu Ala Ala Gly, or (f) (SEQ. ID. NO.:21) Cys Glu Gly Thr His Asn Pro Gly Asn Ser Ser Thr Gln Trp Phe His Asn Gly Arg Ser Ile Arg Ser Gln Val Gln Ala Ser Tyr Thr Phe Lys Ala Thr Val Asn Asp Ser Gly Glu Tyr Arg Cys, or (g) (SEQ. ID. NO.:22) Cys His Ser Trp Arg Asn Lys Leu Leu Asn Arg Ile Ser Phe Phe His Asn Glu Lys Ser Val Arg Tyr His His Tyr Ser Ser Asn Phe Ser Ile Pro Lys Ala Asn His Ser His Ser Gly Asp Tyr Tyr Cys, or (h) (SEQ. ID. NO.:23) Leu Pro Val Leu Thr Ile Val Ala Ala Val Thr Gly Ile Ala Val Ala Ala Ile Val Ile Ile Leu Val Ser Leu Val Tyr Leu, or (i) (SEQ. ID. NO.:24) Lys Lys Lys Gln Val Pro Ala Leu Pro Gly Asn Pro Asp His Arg Glu Met Gly Glu Thr Leu Pro Glu Glu Val Gly Glu Tyr Arg Gln Pro Ser Gly Gly Ser Val Pro Val Ser Pro Gly Pro Pro Ser Gly Leu Glu Pro Thr Ser Ser Ser Pro Tyr Asn Pro Pro Asp Leu Glu Glu Ala Pro Lys Thr Glu Ala Glu Asn Thr Ile Thr Tyr Ser Leu Leu Lys His Pro Glu Ala Leu Asp Glu Glu Thr Glu His Asp Tyr Gln Asn His Ile, or (j) (SEQ. ID. NO.:25) Asn Ser Gly Pro Arg Asn Leu Trp Leu Leu Gln Pro Leu Thr Val Leu Leu Leu Ala Ser Ala Asp Ser Gln Ala Ala, or (k) (SEQ. ID. NO.:26) Cys Gln Gly Ala Arg Ser Pro Glu Ser Asp Ser Ile Gln Trp Phe His Asn Gly Asn Leu Ile Pro Thr His Thr Gln Pro Ser Tyr Arg Phe Lys Ala Asn Asn Asn Asp Ser Gly Glu Tyr Thr Cys, or (l) (SEQ. ID. NO.:27) Cys His Ser Trp Lys Asp Lys Pro Leu Val Lys Val Thr Phe Phe Gln Asn Gly Lys Ser Gln Lys Phe Ser Arg Leu Asp Pro Thr Phe Ser Ile Pro Gln Ala Asn His Ser His Ser Gly Asp Tyr His Cys, or (m) (SEQ. ID. NO.:28) Ser Pro Met Gly Ile Ile Val Ala Val Val Ile Ala Thr Ala Val Ala Ala Ile Val Ala Ala Val Val Ala Leu Ile Tyr Cys, or (n) (SEQ. ID. NO.:29) Arg Lys Lys Arg Ile Ser Ala Asn Ser Thr Asp Pro Val Lys Ala Ala Gln Phe Glu Pro Pro Gly Arg Gln Met Ile Ala Ile Arg Lys Arg Gln Leu Glu Glu Thr Asn Asn Asp Tyr Glu Thr Ala Asp Gly Gly Tyr Met Thr Leu Asn Pro Arg Ala Pro Thr Asp Asp Lys Asn Ile Tyr Leu Thr Leu Pro Pro Asn Asp His Val Asn Ser Asn Asn (o) (SEQ. ID. NO.:30) Thr Gly Asn Ile Gly Tyr Thr Leu Phe Ser Ser Lys Pro Val Thr Ile Thr Val Gln Val Pro Ser Met Gly Ser Ser or a functional mutant, variant or derivative thereof which is capable of binding the Fc region of immunoglobulin.

Even more preferably the polypeptide is derived from ATCC 67414, ATCC67415, ATCC67416, pFc24, pFc113, pFc3.0, pFc3.1 or pFc3.47 as herein described or a polypeptide having at least 40%, preferably at least 50%, still more preferably 60% amino acid homology with said peptide.

Still more preferably the polypeptide comprises amino acids 1 through 280 or 1 through 173 of FIG. 2 (SEQ. ID. NO.:83) or a variant thereof which is capable of binding the Fc region of human immunoglobulin.

In a related aspect the present invention relates to an Fc receptor-like protein with an altered ability to bind immunoglobulin wherein said altered ability is brought about by alteration of one or more amino acid residues which affect immunoglobulin binding.

The phrases "Fc receptor-like protein", "an altered ability to bind immunoglobulin" and "alteration of one or more amino acid residues" have the meanings given earlier.

The above statement includes the receptor for the Fc portion of immunoglobulin, the receptor exhibiting the ability to bind to the Fc portion of mouse and human immunoglobulin.

The present inventors have determined that amino acid residues or regions of residues in the first and second domains of the FcγRII receptor and FcεRI receptor function in binding of immunoglobulin. As the extracellular regions of Fc receptors for immunoglobulins are conserved it is expected that similar regions of Fc receptors for other immunoglobulins such as IgA, IgM and IgD will be implicated in immunoglobulin binding and hence be within the ambit of the present invention.

Preferably the Fc receptor-like protein is in the form of an isolated preparation meaning it has undergone some purification away from other proteins and/or non-proteinaceous molecules. The purity of the preparation may be represented at least 40% Fc receptor-like protein, preferably at least 60% Fc receptor-like protein, more preferably at least 75% Fc receptor-like protein, even more preferably at least 85% Fc receptor-like protein and still more preferably at least 95% Fc receptor-like protein relative to non-Fc receptor-like molecule material as determined by weight, activity, amino acid similarity, antibody reactivity or any other convenient means.

The Fc receptor-like molecule may be bound to a cell membrane or a support means, or be soluble in form. Where a pharmaceutical use is indicated preferably the molecule is soluble for example as a genetically engineered soluble molecule.

Soluble Fc receptor like molecules can be made by methods such as those of Ierino et al J. Exp. Med. (Nov) 1993.

The Fc receptor-like protein may also be labelled with a reporter molecule providing, under suitable conditions, a detectable signal. Such reporter molecules include radionucleotides, chemiluminescent molecules, bioluminescent molecules, fluorescent molecules or enzymes. Commonly used enzymes include horseradish peroxidase, glucose oxidase, β-galactosidase and alkaline phosphatase amongst others.

Preferably the Fc receptor-like protein is an amino acid mutant, variant or derivative of a native Fc receptor. This means that the Fc receptor-like protein comprises a peptide which has undergone deletion, insertion, substitution or other changes to its amino acid residues compared to a native Fc receptor. The native Fc receptor providing the basis for the mutant, variant or derivative may be derived from human or animal species. Such animal species are preferably mammalian species such as mice, rats, rabbits, bovine, ovine, porcine, equine or caprine species.

Deletion, insertion or substitution of amino acids to produce the Fc receptor-like protein of the present invention may be performed by known means as described above.

Alternatively substitutions may be with an amino acid of different chemical characteristics imparting a different character to the molecule when compared to a native Fc receptor.

In a preferred embodiment the invention relates to an Fc receptor-like protein having enhanced ability to bind immunoglobulin wherein the enhanced ability is brought about by alteration of one or more amino acid residues which affect immunoglobulin binding ability.

The phrase "enhanced ability to bind immunoglobulin" means that the molecule has an immunoglobulin binding activity higher than, or increased compared to, a native Fc receptor in a given class.

The alteration of one or more amino acid residues may be in the first or second domain.

Where the Fc receptor-like protein has an enhanced ability to bind IgG, preferably alterations in the first domain to included changes to the A/B, C/C' and/or E/F loops or G/A strand. The term "equivalents" means amino acid residues that occur in the same position on the native Fc receptor which comprise the putative loops.

Alterations to the second domain of a Fc receptor-like protein specific for IgG include changes in the F/G, B/C and/or C'/E loops, and/or G/A strand which connects domains 1 and 2.

Preferably the changes comprise substitution of one or more amino acids especially a conservative substitution. Such changes include but are not limited to replacement by alanine, glycine, serine, asparagine or small synthetic neutrally charged amino acids. Most preferably the replacement is alanine.

More preferably the alterations are at the following positions 133, 134, 158, 159, 160 and/or 161.

Still more preferably the $Asp^{133}$, $Pro^{134}$, $Leu^{159}$, $Phe^{160}$ and/or $Ser^{161}$ residues of FcγRII are replaced by alanine.

Where the Fc receptor-like protein has an enhanced ability to bind IgE preferably the alterations in the first domain include changes in A/B, C/C' or E/F loops or the G/A strand that connects domain 1 and domain 2

Alterations to the second domain of a Fc receptor-like protein specific for IgE include changes in the F/G, C'/E or B/C loops.

More preferably the changes are at the following positions 130, 156, 160 and/or 161.

Still more preferably the $Trp^{130}$, $Trp^{156}$, $Tyr^{160}$ and/or $Glu^{161}$ is/are replaced by alanine.

In another preferred aspect the invention relates to an Fc receptor-like protein having reduced ability to bind immunoglobulin wherein the reduced ability is brought about by the alteration of one or more amino acid residues which affect immunoglobulin binding ability.

The phrase "reduced ability to bind immunoglobulin" means that the protein has an immunoglobulin binding activity lower than, or decreased compared to, a native Fc receptor in a given class. This includes a reduced activity for binding of one form of immunoglobulin such as, for example, dimeric immunoglobulin.

The reduced binding ability may be brought about by deletions, insertions or substitutions of amino acid residues in the first or the second domain. Preferably the reduced binding ability will be the result of substitution or deletion of one or more amino acid residues although insertions are also clearly contemplated.

Preferably substitutions will be with an amino acid residue (natural or synthetic) which has different chemical characteristics to the corresponding amino acid in the relevant native Fc receptor in question. Such as for example the substituted amino acid may have different charge, acidity or basicity.

The additions, substitutions and/or deletions may be made in accordance with standard methods as described above.

Where Fc receptor-like protein has a reduced ability to bind IgG preferably alterations in the first domain include replacement of that domain or changes to the A/B, C/C' or E/F loops or G/A strand.

More preferably the changes are at the following positions 10 to 21, 42 to 48 and/or 59 to 62.

Alterations to the second domain of a Fc receptor-like protein specific for IgG preferably include changes to the F/G, B/C, or C'/C loops.

More preferably the changes are at the following positions 113, 114, 115, 116, 129, 130, 131, 132, 133, 155 and/or 156.

Still more preferably the first domain is deleted or replaced by a domain from an Fc receptor for another immunoglobulin of $Fc_\gamma RII$.

Alternatively still more preferably the $Lys^{113}$, $Pro^{114}$, $Leu^{115}$, $Val^{116}$, $Phe^{129}$ $Ser^{130}$ Arg/$His^{131}$ $Leu^{132}$, $Asp^{133}$, and/or $Pro^{134}$ of $Fc_\gamma RII$ is/are replaced by alanine.

Where the Fc receptor-like protein has a reduced ability to bind IgE preferably alterations in the first domain include the A/B, C/C' or E/F loops.

More preferably the changes are at the following positions in the first domain 10 to 21, 42 to 48 and/or 59 to 62.

Alterations in the second domain of a Fc receptor-like protein specific for IgE preferably include changes to the F/G, C'/E or B/C loops.

More preferably changes are at one or more of the following positions: 125 to 135, 129 to 131, 131, 132, 155, 158 and/or 159.

Still more preferably the B/C loop ($Trpl^{110}$ to $Lys^{117}$) of FceRI is deleted or replaced by a B-C loop from a receptor for another immunoglobulin.

Alternatively still more preferably the C'/E loop ($Tyr^{129}$ to His134) of $Fc_\epsilon RI$ is deleted or replaced by a C'/E loop from a receptor from another immunoglobulin.

Still more preferably $Tyr^{131}$, $Glu^{132}$, $Val^{155}$, $Leu^{158}$ and/or $Asp^{159}$ of $Fc_\epsilon RI$ is/are replaced by alanine.

In another aspect the present invention relates to antagonist compounds which interfere with the amino acid residues in Fc receptors which are involved in immunoglobulin binding. Such compounds embrace any compound which interact with these amino acid residues or regions of residues so as to interfere with or reduce immunoglobulin binding and include compounds which bind to these residues or regions of residues by hydrophobic, electrostatic or other chemical interaction. This also includes compounds which interfere with the structural integrity of the molecule thereby reducing its affinity for immunoglobulin as well as compounds which directly interfere with the amino acids involved in immunoglobulin binding. These Fc receptor antagonists may be used in the treatment of asthma, rheumatoid arthritis, lupus, glomerulonephritis, etc and a host of immune complex and other diseases including but not limited to autoimmune diseases.

Where the antagonist is intended to block or reduce IgG binding then the compound will preferably interact with the A/B, C/C' or E/F loops in the first domain or with the F/G, B/C or C'/E loops in the second domain or the G/A strand. Preferably the compounds will be capable of binding to or blocking the function of one or more of the following residues in the native Fc receptors 10-21, 42-48, 59-62, 113, 114, 115, 116, 129, 130, 131, 132, 133, 156, 158, 159, 160 and/or 161 or their functional equivalents.

Where the antagonist is intended to block or reduce IgE binding in disease such as asthma or allergy then the compound will preferably interact with the A/B, C/C' or E/F loops in the first domain and/or the F/G, C'/E or B/C loops of the second domain or the G/A strand.

Preferably the compounds will be capable of binding to or blocking the function of the following residues: 10-21, 42-48, 59-62, 125-135, 129-131, 131, 132, 135, 155, 158 and/or 159.

In another aspect the present invention contemplates pharmaceutical compositions containing as an active ingredient the protein with Fc receptor activity or the antagonist compounds described above, depending on the condition to be treated together with a pharmaceutically appropriate carrier or diluent. For example, Fc receptor-like protein with enhanced immunoglobulin binding ability may be used to treat diseases including by not limited to glomerulonephritis, lupus, arthritis, heparin induced thrombocytopenia thrombosis syndrome (HITTS) or idiopathic thrombocytopenia pupuera (ITP), asthma, allergy, eczema and rheumatoid arthritis. Fc receptor-like protein with reduced binding ability may be used to treat disease where it is desirable to remove only some or one particular kind of immunoglobulin. Antagonist compounds may be used in the treatment of inappropriate or excessive immunoglobulin levels or aggregates or immune complexes are part of the symptoms of the disease such as asthma, allergy, rheumatoid arthritis, etc. For the purpose of describing the pharmaceutical compositions, all of the above molecules and compounds will be referred to herein as "active molecules". The use of the term "active molecules" therefore should be read as one or more of the above molecules depending on the condition to be treated.

The active molecules of the pharmaceutical compositions are contemplated to exhibit therapeutic activity when administered in an amount which depends on the particular case. The variation depends, for example, on the animal and the active molecule. For example, from about 0.05 µg to about 20 mg of the protein with Fc receptor activity or antagonist compound may be administered per kilogram of body weight per day to alter Fc receptor-immunoglobulin interaction. Dosages may be adjusted to provide the optimum therapeutic response. For example, several divided doses may be administered daily, weekly, monthly, or in other suitable time intervals or the dose may be proportionally reduced as indicated by the exigencies of the situation. The active molecules may be administered in a convenient manner such as by the oral, intravenous (where water soluble), intraperitoneal, intramuscular, subcutaneous, intranasal, intradermal or suppository routes or implanting (e.g. using slow release molecules). Depending on the route of administration, the active molecules may be required to be coated in a material to protect said molecules from the action of enzymes, acids and other natural condition which may inactivate said ingredients.

The active molecules may also be administered in dispersions prepared in glycerol, liquid polyethylene glycol, and/or mixtures thereof and in oils. Under ordinary conditions of storage and use, these preparations contain a preservative to prevent the growth of microorganisms.

In another aspect the invention relates to an agent for use in diagnostic assays, treatment of disease or removal of immunoglobulin from body fluids comprising a protein with Fc receptor activity together with appropriate diluents or excipients.

In another aspect the invention relates to use of the protein with Fc receptor activity or the antagonist compounds in the manufacture of medicaments.

The invention further extends to a method of cloning a nucleic acid encoding a protein with Fc receptor activity said method comprising:

a) contacting a sample of nucleic acids derived from an animal present in a DNA library or other suitable form with a nucleotide probe labelled with a reporter molecule said probe being specific for the nucleic acid encoding the protein with Fc receptor activity and identifying the resulting probe-nucleic acid hybrids, b) ligating the nucleic acid identified above to a suitable vector, and c) transforming a suitable host with said vector.

Optionally, an amplification step using appropriate oligonucleotide primers may be carried out prior to step a) above to enrich the proportion of the desired nucleic acid. Suitable primers include those used in the Examples and are able to be constructed by known methods.

The invention also extends to a method of producing the nucleic acid molecules of the invention comprising mutating a nucleic acid encoding an Fc receptor such that one or more of the amino acids which affect immunoglobulin binding are altered resulting in an encoded protein which has an altered ability to bind immunoglobulin.

The phrases "amino acids which affect immunoglobulin binding" and "altered ability to bind immunoglobulin" have the meanings given earlier.

The term "mutating" encompasses direct mutagenesis of a native Fc receptor gene by chemical means, SOE-PCR or de novo synthesis. The different methods of effecting mutations will be well known to those skilled in the art.

The invention also relates to a method of producing the protein with Fc receptor activity of the invention by recombinant means. The method comprises causing the nucleic acid molecule of the invention to be expressed and isolating or purifying the protein to at least some degree. Generally the nucleic acid molecule will be present on a suitable vector or integrated into a host genome. Suitable hosts, vector to those skilled in theods will be known to those skilled in the art and have been described above.

In another aspect the invention relates to a method of determining the presence of immunoglobulin present in a sample said method comprising contacting said sample with a protein with Fc receptor activity of the present invention, for a time and under conditions sufficient to allow the protein and any immunoglobulin present in said sample to bind and detecting said bound protein-immunoglobulin.

The sample may be from any source where it is desired to determine the presence of immunoglobulin. Samples from body fluids and secretions such as blood, saliva, sweat, semen, vaginal secretions may be used. Solid tissue samples such as biopsy specimens from kidneys, etc, are also contemplated.

The term "a protein with Fc receptor activity" has the same meaning as given earlier and includes any native Fc receptor whether derived from natural sources or by recombinant means. Preferably the Fc receptor is at least partly purified.

Detection of the bound protein can be determined by any convenient means. Preferably presence of immunoglobulin is detected by a protein with Fc receptor activity which is labelled by a reporter molecule. Alternatively the bound antibody-receptor may be detected by an anti-Fc receptor labelled with a label, reporter molecule anti-Ig or other detectable signal.

The protein of the present invention may be soluble or bound to a solid support such as nitrocellulose, paper, matrices or resins which will be known to those skilled in the art.

Another aspect of the invention relates to a kit for detecting immunoglobulin including immune complexes in a sample, said kit comprising in compartmentalized form a first compartment adapted to receive a protein with Fc receptor activity as described above and at least one other compartment adapted to contain a detector means.

The phrase "detector means" refers to means for detecting immunoglobulin bound to protein with Fc receptor activity and includes the appropriate substrates buffers, etc required for detection of the bound immunoglobulin-receptor.

In this connection the Fc receptor-like protein with enhanced ability to bind immunoglobulin of the present invention provides a useful laboratory reagent. This is particularly so with a protein with Fc receptor activity specific for IgG because the protein is capable of selectively binding immunoglobulin complex. Thus the protein with enhanced Ig binding ability may be used in immunoprecipitation as a replacement for protein A, for example, which does not exhibit a selective binding ability.

In a related aspect the present invention provides a method of detecting immune complex in a sample comprising contacting said sample with a protein with Fc receptor activity which is specific for IgG for a time and under conditions sufficient for any complex present in the sample and the protein to form a further complex and detecting said further complex.

Preferably the protein is a Fc-receptor-like protein with enhanced immunoglobulin binding ability. The above method utilizes the ability of the protein for IgG to only bind complexes as they do not recognize monomeric IgG. In the preferred aspect, the enhanced activity of the Fc receptor-like protein provides a more sensitive assay as it will detect lower levels of complex in the sample and also be selective for the same.

The above method may be a useful tool in diagnosis of diseases where immune complexes are implicated such as, for example, glomerulonephritis, lupus, arthritis, heparin induced thrombocytopenia thrombosis syndrome (HITTS) or idiopathic thrombocytopenia pupuera (ITP).

In yet another aspect the present invention relates to a method of removing immunoglobulin from a body fluid comprising taking body fluid from a patient, contacting the body fluid with a protein with Fc receptor-like activity or a Fc receptor-like protein with an enhanced ability to bind immunoglobulin, for a time and under conditions sufficient to allow the protein to bind said immunoglobulin, removing said bound immunoglobulin from the body fluid and replacing said body fluid in the patient.

Preferably the method involves removal of immune complex. This may be used in the treatment of diseases where it is desirable to remove immune complexes such as in lupus, rheumatoid arthritis or after infection in a glomerulonephritis patient.

More preferably the method is used in plasmapheresis in the treatment of immune complex diseases. Even more preferably the method utilizes a Fc receptor-like protein with enhanced ability to bind IgG.

Preferably the protein is bound to a solid support such as a membrane when used in plasmapheresis.

In another embodiment the present invention relates to a method of treatment of disease where the disease involves immune complexes, aggregates of immunoglobulin or antigen-antibody interactions, said method comprising administering an effective amount of a protein with Fc receptor activity or an antagonist compound of the invention to a subject.

The subject may be a human or animal, preferably a mammal.

Preferably the protein used is a Fc receptor-like protein with enhanced immunoglobulin binding ability is used in the method. In some diseases however a Fc receptor-like protein with reduced immunoglobulin, or differential immunoglobulin binding ability may be indicated such as where it is desirable bind one form of immunoglobulin and not another. For example, a protein with altered IgG binding ability such that it binds complexes and not monomers may be useful.

Preferably the protein used in the method are soluble. More preferably they are administered in a pharmaceutical composition. Fc receptor-like proteins with enhanced IgG binding ability may be used in the treatment of diseases such as immune complex diseases, glomerulonephritis, lupus, diseases involving inappropriate production of IgG after infection, heparin induced thrombocytopenia thrombosis syndrome (HITTS) and idiopathic thrombocytopenia pupuera (ITP).

In addition, Fc receptor-like proteins with enhanced IgG binding ability may be used in the treatment of any disease involving IgE, where IgE is one of the causative agents of disease. Such diseases include asthma, allergy, eczema and rheumatoid arthritis.

It is envisaged that a soluble IgE specific Fc receptor-like protein with enhanced activity according to the invention will be particularly useful as a competitive inhibitor of IgE binding when administered to a subject. The protein will function in two ways. First, it will absorb unbound IgE and second it will displace already bound IgE by virtue of its strong affinity for IgE. In this way the action of IgE in an asthma attack or allergic reaction such as bee sting may be reduced or alleviated.

Similar comments apply to a soluble IgG specific Fc receptor-like protein. It is envisaged that a soluble IgG specific Fc receptor-like protein with enhanced activity according to the invention will be particularly useful as a competitive inhibitor of IgG binding when administered to patients. First it will absorb to immune complexes aggregates or IgG which will prevent binding to cell surface FcγR, e.g. FcγRI, FcγRII, FcγRIII which will prevent or reduce activation of inflammation.

In this way immune complex induced inflammation, e.g. in rheumatoid arthritis, Good pastures syndrome or lupus will be reduced or alleviated.

The invention will now be described with reference to the following nonlimiting Examples.

EXAMPLE 1
Isolation of Full Length cDNA Clone

The Fc(gamma)R has been purified to homogeneity using the anti-Ly-17.2 antibody. Protein and peptide sequencing studies have enable one third of the molecule to be sequenced (Table 2). Consensus oligodeoxynucleotide probes constructed from the protein sequence (Table 3) were used to isolate a cDNA clone (Pfc24). Southern analysis established that the cDNA insert of Pfc24 reacted with the probes (data not shown). Maxam-Gilbert sequencing of the 5' and 3' ends of Pfc24 (see FIG. 1) indicated that it was not full length since no entire leader sequence or inframe termination codon was apparent at the 5' and 3' ends respectively. A full length cDNA clone, pFc113 was isolated by reprobing the WEHI 3B library with oligodeoxynucleotide probes constructed from the nucleotide sequence of the 5' and 3' ends of pFc24. These probes corresponded to nucleotides 140–187 (Probe 1.5) or 959–1000 (probe 1.6) (FIG. 1, Table 4) and only clones to which both probes hybridised were subsequently isolated. The cDNA insert of pFc113 contains approximately 2.0 kilobase pairs whereas that of pFc24 has only 962bp but is entirely embodied in pFc113 between nucleotides 61 and 1023.

Nucleotide and Amino Acid Sequence

The amino acid sequence predicted from the nucleotide sequence of pFc113 (FIG. 1 SEQ. ID. NO:80–81) indicates that mature FcR is a membrane molecule composed of 301 amino acids and is synthesized with a 29 amino acid leader sequence. The amino acid sequences of 10 of 11 peptides we had previously sequenced from immunopurified FcR were found encoded by pFc113 cDNA (FIG. 1). (Hibbs et al, 1986). Miscalling of several amino acid residues during sequencing of the peptides accounts for the differences between the sequence of peptides L5 and CNBR and the predicted sequence of these regions from the cDNA clone. Also the CNBR peptide is preceded by a Trp not the predicted Met but it is known that CNBR will cleave on the C terminal side of Trp residues in acid solutions (Ozols et al, 1977).

Several other important observations can be made from the predicted amino acid sequence. Firstly, a single transmembrane region of 28 amino acids extends from Leu180 to the sequence Lys209-Lys210-Lys211 and separates the 94 amino acid long cytoplasmic region from the 179 extracellular amino acids. Secondly, the extracellular portion of the FcR molecule contains two regularly spaced pairs of Cys residues, the first pair Cys 28 and Cys 70 separated from each other by 41 amino acids and the second pair Cys 109 and Cys 153 separated by 43 amino acids. This regular arrangement suggests the extracellular portion may be organized into two disulfide bonded domains (see homologies below). Thirdly, four potential N-linked glycosylation sites are present in the extracellular region of the receptor, with two glycosylation sites located within each of the putative domains. These potential glycosylation sites have been verified as being authentic sites of carbohydrate attachment (Green et al, 1985 and see "Additional Structural Features of murine FcR" below).

Homologies of Murine FcR

Comparison of the amino acid sequences within the FcR molecule (assessed using the Dayhoff ALIGN program, Dayhoff et al, 1983) indicated that there was a significant degree of internal homology within the extracellular domains. Using the mutation data matrix, scoring is based on the extent of mutation required for amino acid substitution in established protein families. The score for the optimal alignment is then represented as the number of standard deviations by which the maximum score for the alignment of two sequences exceeds the score for a large number of alignments after randomization of the original sequences (Dayhoff et al, 1983). Arbitrary setting of the boundaries of these domains around the pairs of Cys residues showed that alignment of amino acids 5–86 (FcR, domain 1) with amino acids 88–175 (FcR, domain 2) gave 29% identical residues with an ALIGN score of 7.1 SD i.e. the probability of such an alignment occurring by chance is $>10^8$ and implies the tandem duplication of a single domain. Such repeated domain structures are evident in Ig and related molecules that comprise the Ig superfamily (Williams 1985). To further examine possible homologies to other molecules we undertook computer searches of a number of nucleic acid and protein data bases. These revealed the FcR domain 1 was most homologous to murine Class II antigens in particular to the Ig like beta2 domain of I-Ebeta and gave a highly significant ALIGN score of 8.3SD. In addition to the homology with Class II antigens, other features of the FcR domains indicate their relatedness to Ig superfamily members. The homology to members of the Ig supergene family is seen principally around the Cys residues. The sequences surrounding cysteine residues 70 and 153 were shown to be highly representative of the consensus sequence (SEQ. ID. NO.:31) (Gly-X-Tyr-X-Cys) around the disulfide-bonded Cys residue in IgV-region domains. In addition, the sequences flanking Cys residues 28 and 109 were indicative of the disulfide-bonded Cys near the amino-terminus of the V-region of Ig chains and other Ig related molecules. Furthermore, the Trp residue located 13 residues downstream from Cys 28 and a Phe residue 13 residues downstream from Cys 109 are commonly observed in this position of Ig-like structures. The Ig related molecules Thy-1 and CD4, which also possess these characteristics have been shown experimentally to contain intrachain disulfide bonds (Williams and Gagnon, 1982; Classon et al, 1986a).

It is clear therefore that the receptor for immunoglobulin shows a common evolutionary ancestry with its ligand but comparison of entire Ig and FcR domains shows a low overall homology indicating that they must have diverged relatively early in evolution. The high degree of homology with MHC Class II molecules is interesting in the light of the physical association of some FcR with Class II molecules on the cell surface (Dickler and Sachs, 1974).

In addition to the poly Ig receptor (see above), we also sought homology to other IgG binding molecules. No homology of FcR domains to Staphylococcal protein A (Sjodahl, 1977) was found. The Fc(gamma)R receptor described herein is highly homologous to other beta1 Fc(gamma)R except for a stretch of 9 amino acids in the cytoplasmic tail from Gly241 to Pro249. The discrepancies between the nucleotide/amino acid sequences shown in FIG. 1 may have arisen by the omission of three nucleotides. The nucleotide and predicted amino acid sequence of the beta1 form of the Fc (gamma)R was determined and is shown in FIG. 1 (SEQ. ID. NOS.:80–81). In addition, another form of the Fc(gamma)R is highly homologous to the FcR described here -almost certainly being a splice variant. The splice site occurs in the region encoding the intracellular domain indicating that the beta1 and beta2 forms of the FcR have identical extracellular domains. A third form of the FcR has also been identified by cDNA cloning studies and designated the alpha FcR. The mature alpha protein shows a little variation from the receptor described herein with approximately 7% variation in amino acid content of the ligand binding domains. All major structural features in the domains of the three variants, alpha, beta1, beta2(SEQ. ID. NOS.:133, 134 and 136, respectively), are conserved, i.e. (4 N-linked carbohydrate side chains, 2 pairs of cysteine residues). Thus molecular analysis of Fc(gamma)R clearly indicates that murine FcR are a family of highly homologous proteins. It should also be noted that the Ig binding proteins—protein A and the FcR described herein all have repeated ligand binding domains which may be necessary for stability and specificity of ligand binding.

Additional Structural Features of Murine FcR

We have demonstrated that adjacent pairs of cysteine residues in purified Fc(gamma)R are involved in disulfide bonding. Protein was purified by affinity chromatography then digested with proteolytic enzymes either before or after reduction of disulfide bonds with dithiothreitol.

Digests were then fractionated by reversed-phase chromatography. Peptides present in the digests of unreduced Fc(gamma)R but absent from the digested reduced Fc(Gamma)R were sequenced and shown to correspond to disulfide-bonded peptides. The results obtained indicated that Cys 28 is disulfide-bonded to Cys-70 and that Cys-109 and 153 are involved in disulfide bonding.

Extensive peptide sequencing has also determined that four possible N-linked glycosylation sites in mouse Fc(gamma)R are in fact authentic sites of carbohydrate addition. This was judged by the absence of an asparagine in the expected position in the peptide sequence.

Expression of mRNA

Analysis of FcR expression in cell lines was then performed by Northern blotting. Two mRNA transcripts were evident when probing poly-A$^+$ mRNA from the WEHI 3B cell line, with nick translated cDNA. These transcripts were absent from the FcR$^-$ cell line F4N. Since there is FcR heterogeneity with respect to both specificity and expression in cell lineages (Dickler, 1976; Unkless et al, 1981; Teillaud et al, 1985; mRNA from cell lines of different lineages was examined using an oligodeoxynucleotide probe (Probe 1.10) (corresponding to nucleotides 545–574) that hybridised to both transcripts in WEHI 3B cells. Northern blots showed that while both transcripts were present in the myelomonocytic cell lines WEHI 3B, the lower Mr species was predominant in J774 macrophage cells and was completely absent from the FcR$^+$ lymphoma K36, where only the higher Mr species could be detected. The presence of multiple Fc(gamma)R mRNA transcripts (termed alpha, beta1 and beta2, beta1 being identical to that encoded by pFc113 described herein) in different cell types was also noted.

Relationship of MRNA Transcripts and Surface FcR

To establish the relationship between mRNA transcription and surface Fc(gamma)R expression, we investigated the presence of mRNA transcripts by Northern analysis using oligonucleotide probes specific for the beta1, beta2 and alpha transcripts (Table 4) and compared this with immune complex binding (using rabbit IgG and various IgG isotypes) and whether the cells were Ly-17.2+ or 2.4G2+ at the surface (Table 5).

The results indicate that the beta1 Fc(gamma)R is the receptor for IgG1/2b, heterologous IgG and possibly other Ig since cells which express only the beta1 receptor only can bind IgG1/IgG2b as well as rabbit IgG coated erythrocytes (Table 5). In addition, K36 cells have the Ly-17.2+ and 2.4G2+ molecules which have been shown to be identical and are epitopes on the Fc(gamma)R molecule (Unkless, 1979; Hibbs et al, 1985; Holmes et al, 1985). Furthermore antibodies to these molecules completely inhibit the binding of IgG1/2b and rabbit IgG complexes to the cell surfaces. Thus the beta1 variant must code for molecules which have Fc binding ability and the epitopes detected by the 2.4G2 and Ly-17.2 antibodies. Both the Ly-17.2 and 2.4G2 epitopes are clearly present on the beta1 and beta2 molecules since both antibodies were used to purify these molecules for amino acid sequencing in this study. Finally, the pFc 113 cDNA (in the pKC3 vector) described herein was transfected into FcR negative LTA-5 cells resulting in expression of FcR (Ly-17.2) on the cell surface (Table 5) indicating that this clone encodes an immunoglobulin binding FcR. The interactions of the alpha and beta 2 receptors with antibody and immune complexes remains to be precisely determined. WEHI 3B and J774 cells both express alpha and beta1 mRNA transcripts but only J774 cells express beta2 mRNA although both bind IgG1/2b and rabbit IgG complexes and are Ly-17+ (Table 5). Whilst cDNA expression experiments will be needed to define the specificity of these receptors, it is likely that the alpha, beta1 and beta2 receptors will have the same binding properties of immune complexes.

Southern Blot Analysis

Southern hybridization studies were performed to determine whether the heterogeneity observed at the mRNA and protein levels was also apparent in the genome. Probing of murine spleen DNA digested with Hind III or Pst I generated two fragments to which the CDNA hybridised. Digestion with Eco RI also produced two major and several other weakly hybridised fragments. Thus it appears likely that only a single, or few, copies of a highly conserved gene are present in the genome. The heterogeneity of receptors shown by serological studies, together with the presence of multiple mRNA transcripts indicates the receptors are likely to be a family of homologous proteins.

Isolation of Human Fc(gamma)R cDNA Clones

Since human Fc can bind mouse and human immunoglobulin and have many similarities with mouse FcR, (Dickler, 1976; Anderson and Abraham, 1980; Kulczycki et al, 1981; Perussia et al, 1983; Dorrington and Klein, 1983), it is likely that there is a high degree of structural and functional homology which conserved at the nucleic acid and amino acid levels. Thus we used the mouse cDNA pFc24 and a combination of oligonucleotides, probes 1.5, 1.6, 1.10 (Table 4) to screen a library constructed from mRNA isolated from human acute monocytic leukaemia cells THP-1. Several clones were isolated including HFc3.0, HFc3.1 and HFc3.47. The results demonstrated that, 1. pFc113 cDNA hybridised to the cDNA inserts of HFc3.1 and HFc3.47; 2. probe 1.5 hybridised to HFc3.1 cDNA but not to HFc3.47; 3. probe 1.10 hybridised weakly to HFc3.1 cDNA but not to HFc3.47; 4. probe alpha did not hybridize to either clone and 5. probe 1.6 hybridised to HFc3.47 but not HFc3.1. None of the probes, except probe 1.6, hybridised to the lambda arms—the hybridization of probe 1.6 to the lambda arms was due to incomplete digestion prior to Southern transfer. The likely homology of the HFc3.1 and HFc3.47 cDNA clones to the mouse cDNA clones was then confirmed by nucleotide sequencing.

Characterization of Human FcR cDNA

Figure 8:
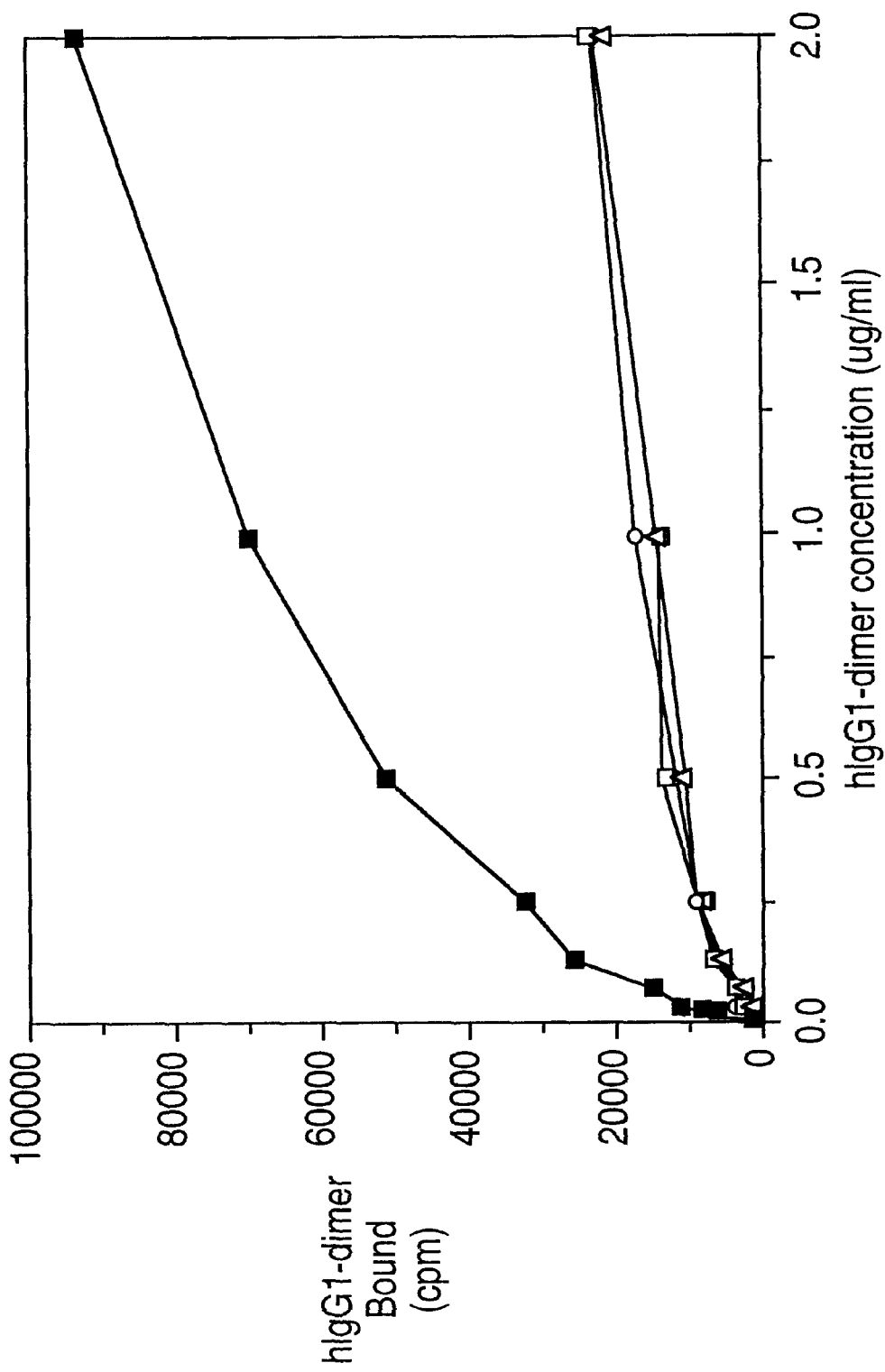
FIG. 8. Human IgG1-dimer binding of chimeric Fc receptors. Radiolabelled dimeric human IgG1 was titrated on COS-7 cells transfected with wild-type Fc$_γ$RIIa (■) or chimeric receptor cDNAs; D1εD2γ ( ), γ109–116ε ( ), γ130–135ε ( ). All of the chimeras were expressed on the cell surface as determined by EA resetting outlined in FIG. 7.

The human cDNA inserts were subcloned into plasmid vectors. The complete nucleotide sequence of a cDNA encoding the human Fc(gamma)R and its predicted amino acid were determined (these are shown in FIG. 8 of U.S. Ser. No. 896,457 filed May, 27, 1992). Clone HFc3.1 contains sequence encoding the mature Fc(gamma)R protein and most of the leader sequence, as well as the entire coding sequence. The high degree of homology, seen both at the nucleotide and amino acid level, between the mouse FcR sequences and the sequence of HFc 3.1, confirms that this clone encodes human FcR. The complete amino acid sequence of the human FcR, aligned with the sequences of mouse alpha and beta1 FcR (not shown). Breaks have been introduced to optimize the alignment. The incomplete leader sequence of the human FcR encoded by HFc 3.1 is highly homologous to the leader sequence of the mouse alpha FcR (56% conservation of amino acids) but bears no homology to the mouse beta1 Fc(gamma)R leader sequence. The N-terminus of the human Fc(gamma)R has been predicted on the basis of homology to the mouse alpha Fc(gamma)R N-terminal sequence. The region between the N-terminus and the first cysteine residue is the most highly conserved region between the two species, showing 71 and 73 percent amino acid homology with the murine beta1 and alpha Fc(gamma)R respectively. There is also a high level of amino acid conservation in the remaining extracellular portion between FcR of mouse and man. Like the mouse, the extracellular region is divided into two disulfide-bonded domains: the first pair of cysteine residues being separated by 41 amino acids and the second pair by 43 amino acids. Both disulfide bonded domains bear striking homology to the mouse beta1 and alpha Fc(gamma)R. Amino acid sequence comparison of the first domain shows approx. 56 percent conservation between the human FcR and both mouse alpha and beta Fc(gamma)Rs. Similarly, there is approx. 56 percent conservation of amino acids in the second domain between the human Fc(gamma)R and mouse alpha and beta FcRs.

Figure 3B:
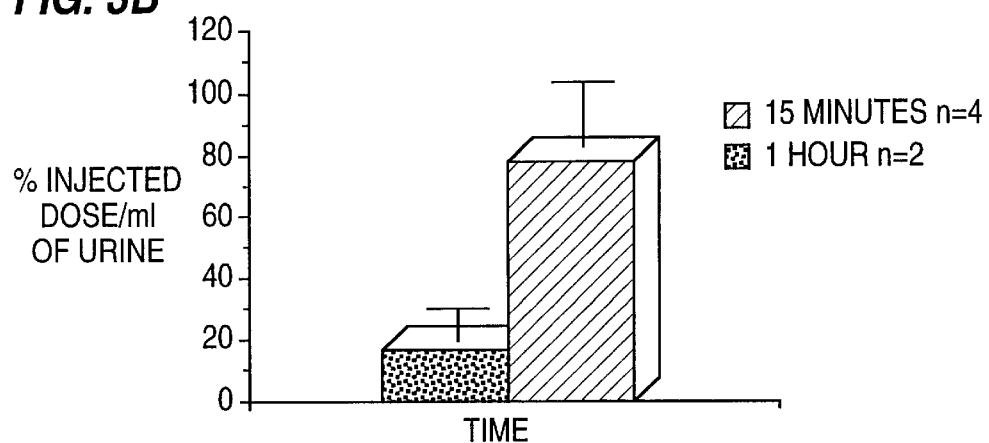

Two potential N-linked glycosylation sites are present in the extracellular region of the human FcR (one in each of the domains) and correspond to two of the four sites present in both mouse alpha and beta1 Fc(gamma)Rs (FIG. 3B of U.S. Ser. No. 07/896,457, now U.S. Pat. No. 5,451,669). The human Fc(gamma)R has a transmembrane region of 28 amino acids extending from residue 219 to the hydrophilic stop transfer sequence Arg (245)–Lys (246)–Lys (247)–Arg (248). This transmembrane sequence is highly homologous to the mouse beta1 Fc(gamma)R (50 percent amino acid homology), but shows no homology to the transmembrane sequence of the mouse alpha Fc (gamma) R receptor.

An in frame termination codon is found at nucleotide 1040 yielding a 75 amino acid intracytoplasmic domain. Comparison of the cytoplasmic domains of both mouse Fc(gamma)Rs with the human Fc(gamma)R shows little identity of either nucleotides or amino acids.

As well as the very low level of homology observed between mouse and human Fc(gamma)R cytoplasmic domains, another clear difference between the mouse and human FcR sequences was apparent. The human FcR sequence contained an additional 117 nucleotides which result in an insertion of 39 amino acids between the two extracellular domains. This sequence is absent from mouse FcRs (FIG. 2 and FIG. 8, 9A of U.S. Pat. No. 5,451,669) and most likely represents an intron sequence. This is inferred from the sequencing of murine genomic clones.

The striking homology of this human Fc(gamma)R to both alpha and beta1 murine Fc(gamma)Rs in the extracellular domain may reflect the fact that human FcR bind mouse IgG and mouse FcR bind human Ig. The cytoplasmic domain of the human HFc3.1 FcR is totally unique and bears no resemblance to either mouse alpha, beta1 or beta2 intracellular domains. This difference could mean the presence of a homologous product in the mouse which has yet to be detected or may reflect the evolutionary divergence of the human and mouse proteins in a region where there may be a high rate of mutation.

Partial nucleotide sequence of HFc 3.47 has also revealed homology with the mouse FcRs. Two non-overlapping fragments were sequenced and the first fragment revealed 80% nucleotide homology with the corresponding sequence in beta1 FcR (nucleotides 629–733). This sequence is present in beta2 and a similar sequence in alpha. The second fragment shared 72% nucleic acid homology with nucleotides 959–1015 of the beta1FcR, this sequence also being present in the beta2FcR but not alphaFcR.

An additional variant sequence was also obtained from the THP-1 library HFc 3.0, the sequence of which is shown in FIG. 2 (SEQ. ID. NOS.:82–83). Like HFc 3.1, HFc 3.0 encodes a protein highly homologous to the mouse alpha and beta FcR receptors. The nucleotide sequence HFc 3.0 is identical to HFc 3.1 with the exception of a large segment (nucleotides 338–455 in HFc 3.1) between the two disulfide bonded domains which has been deleted in HFc 3.0. The protein encoded by HFc 3.0 has an extracellular ligand binding region consisting of two disulfide bonded domains each with a site of attachment for N-linked carbohydrate. In addition, the encoded protein has a 28 amino acid transmembrane region and 75 amino acid cytoplasmic tail. The extracellular region shows an overall homology of 67% identical amino acid residues and the transmembrane region has 14 of 28 amino acid identities with the mouse beta1 and beta2 transmembrane region. The clone HFc3.0 was later found to encode a functional protein.

Expression of Human FcR mRNA

Northern blots were performed to analyze FcR expression in normal human spleen. Two mRNA transcripts were apparent after probing total mRNA from normal human spleen with the cDNA insert from pHFc 3.1. The presence of at least two hybridizing mRNA species in human spleen probably indicates that, like the mouse, there are multiple human FcR proteins arising from either one or more genes.

DNA Analysis

Southern analysis of human genomic DNA from thymus and peripheral blood leukocytes (PBL) demonstrated that identical restriction fragments were present in thymus and PBL DNA when digested with the same restriction enzyme. This indicates that since thymocytes are mostly FcR– and PBLs mostly FcR+, that the FcR gene is not rearranged. In addition since there were only a few major hybridizing restriction fragments it is likely that there is a single or few copies of a highly conserved gene in the human genome.

Since human FcR can bind mouse and human immunoglobulin and have many similarities with mouse FcR, (Dickler, 1976; Anderson and Abraham, 1980, Kulczycki et al, 1981; Perussia et al, 1983; Dorrington and Klein, 1983), it is likely that there is a high degree of structural and functional homology which conserved at the nucleic acid and amino acid levels. Thus we used the mouse cDNA pFc24 and a combination of oligonucleotides, probes 1.5, 1.6, 1.10 (Table 4) to screen a library constructed from mRNA isolated from human acute monocytic leukaemia cells THP-1. Several clones were isolated including HFc3.1, 3.0 and 3.47. Southern analysis of EcoRI digested DNA prepared from each of these clones showed that the mouse beta1 cDNA (from pFC24) hybridised to the cDNA insert of each HFc clone, i.e. HFc3.0, HFc3.47, HFc3.1. The oligonucleotide probe 1.5 hybridized to the cDNA insert of HFc3.1 and 3.0 and the oligonucleotide probe 1.6 to the cDNA insert of HFc3.47. The cDNA inserts were purified and subcloned into M13mp8 and M13mp9 bacteriophages and sequenced by the dideoxynucleotide method according to the strategy outlined in. After sequencing, these clones showed homology with the mouse Fc(gamma)R and indeed identify the Fc(gamma)R. This strategy and similar could be used to isolate the Fc(gamma)R of any species.

IMPORTANCE OF DIFFERENT PARTS OF THE SEQUENCE

The amino acid sequence is divided into several parts (FIGS. 1 and 2):

Leader sequence
Extracellular Region
Transmembrane Region
Intracellular Region (Cytoplasmic Region)
The Leader Sequence The leader sequence of 29 amino acids in the beta1 FcR allows translocation of the nascent protein across the endoplasmic reticulum. The key point of this sequence is its hydrophobic nature (required for membrane insertion) and substitution, addition or deletion of one or more hydrophobic (non-polar) amino acids would not substantially alter this function (see list below).

Extracellular Region.

The extracellular region (ECR) consists of 179 amino acids; their function is to act as the receptor for the Fc piece of Ig molecules. This binding site is elucidated in the later Examples but the following comments on the nature of the sequence are relevant. (a) The FcR is divided into two domains by cysteine residues, Domain 1: Cys 28–Cys 70; Domain 2: Cys 109–Cys 153. Both of these domains may have FcR activity as they are highly homologous. Within each domain all or most of the amino acids are likely to be involved in Ig binding as they are conserved—the two domains are conserved in man and mouse. (i) Thus when the murine sequences are compared for internal homology (i.e. domain 1 and domain 2) they are very similar. (ii) Further, when domain 1 of mouse is compared with that of man, each contain 43 amino acids, of these 24 are identical and in the identical position, of the 19 differences 8 are conservative changes in that only 1 nucleotide has been changed, and of the remaining changes, 6 of the 19 are in the same amino acid group (see below) and 13 are in different groups.

The amino acids substituted belong to the same groups and would therefore not substantially alter the tertiary structure of the molecule and the groupings of amino acids are:

(i) non-polar amino acids: A,V,L,I,P,F,M,W.
(ii) basic side chain: K,R,H
(iii) acidic side chain: E,D
(iv) polar side chain: G,N,Q,C,S,T,Y A, ala=alanine; C, cys=cysteine; D, asp=aspartic acid; E, glu =glutamic acid; F, phe=phenylalanine; G, gly=glycine; H, his=histidine; I, ile=isoleucine; K, lys=lysine; M, met= methionine; N, asn =asparagine; P, pro-proline, Q, gln= glutamine; R, arg=arginine; S, ser=serine; T, thr=threonine; V, val=valine; W, trp=tryptophan; Y, tyr-tyrosine.

Transmembrane Region.

This consists of 28 amino acids and extends from Leu 180–Lys 209 in mouse beta1 FcR. The key feature of this is the hydrophobic nature of the sequence is required as this portion interacts with the hydrophobic cell membrane and anchors the molecule in the cell membrane. Because of the hydrophobic nature, it follows that minor alterations of sequence—substitution of one non-polar amino acid by another, would not alter the essential function of the transmembrane region. It should be noted that such hydrophobic (non-polar) amino acids are alanine (A); valine (V); leucine (L); isoleucine (I); proline (P); phenylalanine (F); methionine (M) and tryptophan (W).

Intracellular Region.

The intracellular region is involved in signal transmission—obtained when the Fc of Ig binds to the FcR. The mode of signal transmission is unknown. A useful sequence of the FcR is described; it is likely that variations of this sequence, obtained by deletion of parts of the whole sequence, could also function in signal transmission. The region of the beta1 receptor that is spliced out in beta2 is important in cells expressing these molecules.

Variants on the materials the subject of this specification are possible:

A. Sequence Variation
The nucleotide sequences encoding the receptor can be variable 1. Because of the degeneracy of the genetic code nucleotide change does not necessarily bring about a change in the amino acid encoded, e.g. the codon GUU specifies a valine residue as do the codons GUC, GUA, GUG each being different by a single nucleotide.

2. Two or three nucleotide changes can give rise to the same amino acid, e.g. codons UUA, UUG, CUU, CUC, CUA, CUG all encode Leucine. Codons AGU, UCC, UCU, UCA, UCG encode serine.

3. Changing one or two nucleotides may result in a conservative amino acid change unlikely to greatly affect the function of the protein, e.g. codon UUG specifies leucine and AUU specifies isoleucine. Also UGG specifies tryptophan and UUU specifies phenylalanine—all conservative changes.

4. Allelic variations. Variations in nucleotide sequence and amino acid sequences of the encoded protein as well as resultant may occur between individual members of the same species. These variations arise from changes in the nucleotide sequences encoding the protein. Thus different forms of the same gene (called alleles) give rise to protein of slightly different amino acid sequence but still have the same function.

5. Variation can occur as the result of differential mRNA splicing where one gene composed of many different segments (exons) of coding sequence—DNA encoding the mature protein—gives rise to a RNA that is spliced such that the portion of the RNA derived from certain exons are removed. Selection of exons is different in different cell types, e.g. the beta1 and beta2 forms of FcR or the alpha and alpha' forms of Ly-2.

6. Proteins having the same function, e.g. immunoglobulin binding, may arise from related genes. Many protein gene families have been described, e.g. immunoglobulins which have nucleotide and amino acid sequence variation but retain their primary function of antigen binding. Such homologous proteins are encoded by homologous genes. These genes arise by duplication of one original gene or by gene conversion.

7. Variation may be intentionally introduced by:

(a) Mutating cloned CDNA or genomic DNA by point mutation, rearrangement or insertion of related or unrelated DNA into the cDNA or genomic clones encoding the functional protein. Such mutated (variant) clones can be used to generate variant proteins or peptides which in the context of this specification may have Ig binding function.

(b) By enzymatic cleavage of the protein (from either in vitro synthesis or normal cell synthesized protein) with or without repair/rearrangement of the cleavage products.

(c) By chemical modification.

(d) By irradiation.

B. Use of Portions of the FcR Protein

The present invention also includes the use of segments of the FcR protein (peptides) and variant peptides synthesized or genetically engineered that have the capacity to bind Ig. The FcR protein and its variants extend from the first methionine in the leader sequence to the most C terminal amino acid of the protein.

C. Isolation of Other FcR

Other FcR within and between species that are homologous at the nucleic acid, protein and functional levels. Because of substantial sequence homologies, the cDNA clones described herein would enable the isolation of related sequences encoding FcR from man, the mouse and other species.

In sum, the present invention includes, but is not limited to:

(i) Description of a molecule, the FcR, which has the capacity to bind the Fc piece of Ig. (ii) The structural arrangement of the 2 extracellular domains which show homology to each other in both man and mouse. (iii) The similarity of these domains in man and mouse. (iv) Differences in the intracellular regions in man and mouse; indicating that signals can be transmitted by different structures. (v) cDNA and other DNA and RNA material encoding for the receptor. (vi) Various vectors including materials.

EXAMPLE 2

Material and Methods

Genetic Engineering and Production of rsFcγRII

Using the PCR, cDNA for a truncated soluble form of human FcγRII was produced by inserting a premature termination codon 5' of the transmembrane domain of a membrane bound FcγRII cDNA (HFc3.0)(as discussed in U.S Pat. No. 5,451,669). The HFc3.0 cDNA encodes the FcγRIIa allelic variant expressing glutamine and histidine at amino acid position 27 and 131 respectively. The oligonucleotide primers used in the PCR were: oligonucleotide, NR1SEQ ID NO:32 (5'TACGAATTCCTATGGAGACCCAAATGTCTC3'); 3' oligonucleotide, FI2, SEQ ID NO:33 (5' CATTCTAGACTATTGGACAGTGASTGGTCAC3'). Both oligonucleotide primers were phosphorylated 100 ng primer, $2\mu$; 1 mM ATP, 50 mM Tric-HCl pH 7.6, 10 mM $MgCl_2$, 5 mM dithiothrietol, 0.1 mM EDTA, 80U of polynucleotide kinase [Pharmacia, Uppsala, Sweden], in 200 $\mu l$, incubated for one hour at 37° C.), and used to amplify the mutated cDNA (100 ng of membrane bound FcγRII cDNA HFc3.0, 50 ng of primers, 50 mM KCl, 10 mM Tris-HCl pH 8.3, 1.5 mM $MgCl_2$ and 2.5 unites of Replinase [Dupont, Boston, USA] with a 30 cycle PCR. The oligonucleotide F12 converted the $Val^{171}$ codon to a TAG stop codon in the HFc3.0 amplified cDNA, resulting in a 635 bp blunt ended nucleotide fragment, which was ligated into the SmaI restriction site of the linearized dephosphorylated pEE6/HCMV/GS eukaryotic expression vector (Celltech, Slough, England). The plasmid construct was transfected into CHO cells using the calcium phosphate precipitation method (Davies et al 1990, J Biol Chem 265: 10410) and grown in glutamine-free Glasgow's Modified Eagles Medium (Flow Laboratories, Australia) with 10% FCS (Commonwealth Serum Laboratories, Australia) dialyzed against PBS. The transfected cells were selected with 15 to 100 $\mu M$ L-methionine sulphoxamine (MSX) (Sigma, St Louis, USA) and the supernatants from surviving clones were screened for the presence of rsFcγRII by their ability to inhibit the binding of an anti-FcγRII mb, 8.26, to FcγRII$^+$ K562 cells, and an ELISA assay using two anti-FcγRII mAbs (8.26 and 8.7) (Ierino et al Mapping epitopes of human FcγRII (CDw32) with monoclonal antibodies and recombinant receptors J. Immunol). The level of rsFcγRII in tissue culture supernatant was increased by: (a) gene amplification; clones originally selected at 15 $\mu M$ MSX were further selected 100 $\mu M$ MSX and (b) growing the transfected CHO cells in the presence of 2 mM sodium butyrate. For large scale production, transfected cells were grown in roller bottles (850 $cm^2$, Becton Dickinson, N.J., USA) seeded at $5 \times 10^7$ cells/ml, and grown for 14 days until the cells were detached.

Immunoaffinity Purification of the RsFcγRII

Cell culture supernatant containing the rsFcγRII was passed through a 0.2$\mu$ filter and the sample was loaded onto an affinity column containing heat aggregated human IgG (HAGG) coupled to sepharose 4B beads (Pharmacia, Uppsala, Sweden). To produce this column, 10 mg of HAGG per 1 g of CNBr-activated freeze dried powder was coupled according to manufacturers guidelines (Pharmacia, Uppsala, Sweden). HAGG was prepared by heating 6 mg/ml of human IgG (Sandoz, Australia) to 63° C. for 30 minutes. After washing the column with PBS, the bound rsFγRII was eluted with a 0.1M acetate buffer pH-4.0 containing 0.5M NaCl. The eluant was immediately neutralized with saturated Tris-HCl and dialyzed against PBS. The $M_r$ and purity of the rsFcγRII were determined by SDS-PAGE analysis. The protein content of the purified samples were determined by absorbance at 280 nm using an extinction coefficient of $\epsilon 1\% = 22$ for a 1 mg/ml protein solution calculated from an amino acid analysis of the rsFcγRII. The purification was carried out at 4° C. and the purified protein stored frozen at −70° C. in PBS. Samples were examined for the presence of endotoxin using the Multi-Test Limulus Amebocyte Lysate Pyrogent (Whittaker Bioproducts, USA).

Biosynthetic Labelling and Deglycosylation of the rsFcγRII

Deglycosylated recombinant protein was produced by adding tunicamycin (Sigma, St Louis, USA) (5 μg/ml) to the secreting transfected CHO cells for two hours at 37° C.; control transfected cells were grown in the absence of tunicamycin. Both control and tunicamycin treated cells were pulsed for two hours with 0.5 mCi of $^{35}$S methionine and $^{35}$S-cysteine (Amersham, Buckinghamshire, England) in glutamine/methionine/cysteine free medium (Select-Amine Gibco, New York, USA) followed by a two hour incubation in the presence of 100-fold excess cold methionine/cysteine. Metabolically labelled supernatants from tunicamycin treated and untreated transfected cells were precleared for 30 minutes at 4° C. with packed sepharose 4B beads coupled to protein A (Pharmacia, Uppsala, Sweden) and immunoprecipitation (using 1 ml of radiolabelled supernatant per mAb) carried out for one hour at 4° C. with 30 μl of packed sepharose 4B beads conjugated to the following mAbs; (a) anti-FcγRII mAbs, 8.26 F(ab'), 8.2 F(ab')$_2$, IV.3 F(ab') and CIKM5 F(ab')$_2$, and a control mAb, 1705 (5084-4.1) F(ab')$_2$ were used with supernatant from transfected cells grown in the absence of tunicamycin; (b) mAb 8.26 was used to immunoprecipitate rsFcγRII from supernatant harvested from transfected CHO cells treated with tunicamycin (Ierino et al, 1992, Mapping epitopes of human FcγRII (CDw32) with monoclonal antibodies and recombinant receptors J. Immunol; Loony et al, 1986, J Immunol 136: 1641; Pilkington et al, 1986 Leukocyte Typing II, Reinherz et al, editors New York: Springer Verlag. 353 pp; Hogarth et al, 1988 Immunogenetics 27: 383). The beads were washed with a buffer containing PBS, 1% BSA, 1 mM PMSF and 0.1% v/v Aprotinin, pH7.4 (Sigma, St Louis, USA), placed in 20 μl of SDS-PAGE sample buffer (0.1M Tris-HCl pH7.5, 0.1% SDS, 0.1M dithiothrietol), boiled for five minutes, analyzed by SDS-PAGE on a 13% gel which was dried and autoradiographed.

Immunoprecipitation and SDS-PAGE Analysis

Purified rsFcγRII (100 μg) was radiolabelled with $^{125}$I (Amersham, Buckinghamshire, England) using Chloramine T (Harlow et al, 1988, Antibodies; A Laboratory Manual, 328 pp). The rsFcγRII was diluted to 0.2 μg/ml in a buffer containing PBS, 1% BSA, 1 mM PMSF and 0.1 % v/v Aprotinin, pH7.4, precleared, immunoprecipitation (0.2 μg of labelled rsFcγRII per antibody) was carried out as described above with 30 μl of packed sepharose 4B beads conjugated to the following antibodies (a) anti-human FcγRII monoclonal antibody, 8.26 F(ab'); (b) control antibody, 1705 F(ab'), mouse IgG2a anti-Ly-12.1; (c) whole mouse IgG1, I-1 anti-CEA; (d) whole mouse IgG2a 1302 (49-11.1), anti-Ly2.1; (e) whole mouse IgG2b 1480 (5041-24.2), anti-Ly-6A.2; (f) whole mouse IgG3, 1308 (49-31.1), anti-Ly-2.1; (g) heat aggregated IgG HAGG (Ierino et al, 1992, Mapping epitopes of human FcγRII (CDw32) with monoclonal antibodies and recombinant receptors; Hogarth et al, 1988, Immunogenetics 27: 383; Hogarth et al, 1982, Immunology 46: 135; Teh et al, 1988, J Immunol Methods, 110: 101; Houlden et al, 1988, Immunogenetics 28: 399).

EA Rosetting Inhibition Assays

The ability of the rsFcγRII to block the binding immune complexes to membrane bound FcγRII was determined by the inhibition of EA rosette formation. Starting at a final concentration of 0.4 mg/ml, doubling dilutions of the purified rsFcγRII or a control protein, OVA, were incubated with 50 μl of freshly prepared 2% EA (rabbit anti-sheep red cell polyclonal antibody diluted 1:50 bound to sheep red cells) for one hour on ice (Parish et al, 1974, Proc. R. Soc. Lond. (Biol), 187: 47). K562 cells (25 μl at $5 \times 10^{10}$ cells/ml) expressing FcγRII were added to the EAs and rsFcγRII, incubated for five minutes at 37° C., spun at 200 g for 3 minutes, and the pelleted cells incubated for 30 minutes on ice. Cells were stained with 0.1% ethyl violet and a typical field of 100 cells was assessed for rosette formation (at least five red cells or 50% of the target cell covered).

Blood Clearance and biodistribution Studies in Mice

BALB/c mice were used to estimate the in-vivo half life of the rsFcγRII and the tissue distribution after an intravenous dose. Purified rsFcγRII (100 μg) was radiolabelled with $^{125}$I using chloramine T (ref 57) and free $^{125}$I removed using PD-10 sephadex column (Pharmacia, Uppsala, Sweden) (<5% free $^{125}$I was present shown by TCA protein precipitation). Groups of four mice were injected intravenously with radiolabelled rsFcγRII and were subsequently sacrificed at various points collecting blood, urine and tissues; each sample was measured for radioactivity expressed as cpm. For the blood clearance study, the blood volume was calculated as 7% of the body weight and the half life (t½) of the rsFcγRII obtained from a logarithmic plot of percentage injected dose versus time, where t½-In 2/gradient (Sterling K J, 1951, J. Clin. Invest. 30: 1228). Radioactivity in the urine was expressed as percentage injected dose/ml of urine, and the organs as percentage injected dose/g of tissue.

Arthus Reaction

A modified reverse passive Arthus reaction (RPAR) model (Pflum et al, 1979, Agents Actions. 9: 184) was established using four to six week old Sprague-Dawley rats (Austin Research Institute, Victoria, Australia) anaesthetized with an ip injection of 1.5 to 2.0 mls of a 1.9% 2,2,2-tribromoethanol (Aldrich Chemical Company, Wisconsin, USA) solution. The rats were shaved, and five minutes after a 5 mg iv injection of OVA into the tail vein, the back of the rat was injected intradermally with either: (a) 50 μl of purified rabbit IgG anti-OVA (500 μg) with 50 μl of PBS, positive control, (b) 50 μl of purified non-immune rabbit IgG (500 μg) with 50 μl of PBS, specificity control, (c) 50 μl of rabbit IgG anti-OVA (500 μg) with 50 μl of rsFcγRII at varying doses (50 to 500 μg) or control protein LKH (500 μg) (Sigma, St Louis, USA), and (d) rsFcγRII alone. Rats were examined at six hours, and macroscopic skin lesions were analyzed (blind by independent observers) using two criteria: (a) size of the lesion; the area in millimeter$^2$ (mm$^2$) was calculated by multiplying the transverse width in two perpendicular directions, (b) "total score" reflecting the severity of each lesion; a minor score of 0 (nil), 1 (mild), 2 (moderate) or 3 (severe) was given for two separate parameters (oedema and erythema), and a "total score" for the lesion was assigned by adding the two minor scores. Skin biopsies at injected sites, taken through the centre of the lesion, were fixed in 10% buffered formalin, stained with hematoxylin-eosin (Department of Pathology, Austin Hospital, Heidelberg, Victoria, Australia) and examined for edema, polymorphonuclear and mononuclear cell infiltrate.
Statistical Analysis A statistical comparison of the size and scores of the rsFcγRII treated skin and the controls (PBS and LKH treatment) was performed by a one-way analysis of variance (Goldman et al, 1985, Statistics: An introduction., 468 pp); p<0.05 was considered significant.

EXAMPLE 3

Production and Purification of rsFcγRII

The rsFcγRII cDNA construct was transfected into CHO cells and resulted in a soluble recombinant protein that was secreted into the cell culture supernatant. Maximally expressing amplified transfected CHO cells (Clone 1.5) were grown in 100 μM MSX and produced 4 to 8 μg of purified rsFcγRII per ml of cell culture supernatant. Immunoaffinity purification using human IgG Fc binding utilized the natural physiological ligand for the receptor and gentle elution conditions enabled maximal yield, with minimal loss of Fc binding capacity of the recombinant protein. The eluted sample analyzed by SDS-PAGE appeared as a band $M_r \sim 31,000$ consistent with the predicted $M_r$ of the rsFcγRII polypeptide chain of 20,000, and the extra size from two N-linked carbohydrate structures. The rsFcγRII was greater than 95% pure analyzed by SDS-PAGE. The stability of the rsFcγRII in tissue culture supernatant was measured by the ELISA assay for FcγRII, and showed it was stable (monoclonal antibody epitopes intact) at 4° C., −20° C. and −70° C. for six months; functional activity of the rsFcγRII, demonstrated by inhibition of EA rosette formation, was completely stable for at least one month at 4° C.

Structure of the Truncated FcγRII

RsFcγRII was deglycosylated to determine the contribution of carbohydrate to the heterogeneity. Cell culture supernatant of Clone 1.5 CHO cells biosynthetically labelled with $^{35}S$ methionine and $^{35}S$ cysteine was used for immunoprecipitation and the $M_r$ of the deglycosylated polypeptide determined after growing the transfected CHO cells in tunicamycin. Immunoprecipitation with F(ab') or F(ab')$_2$ fragments of specific anti-human FcγRII mAbs demonstrated that the total unpurified rsFcγRII in tissue culture supernatant was heterogeneous with $M_r \sim 28,000–36,000$ whereas the IgG purified rsFcγRII was more homogeneous. However, after tunicamycin treatment a homogeneous band $M_r \sim 23,000$ under reducing conditions and $M_r \sim 21,000$ in non-reducing conditions was detected, which agrees with the predicted $M_r$ of 20,000 and demonstrated that the heterogeneity of the total rsFcγRII protein was due heterogeneity within the N-linked carbohydrate, rather than proteolytic degradation or partial translation of the mRNA. The five monoclonal antibodies used designated (IV.3, CIKM5, 8.2, 8.7 and 8.26) have been previously shown to divide into four clusters, each cluster defining a separate epitope on the extracellular domains of FcγRII (Ierino et al, 1992, Mapping epitopes of human FcγRII (CDw32) with monoclonal antibodies and recombinant receptors). Cluster 1 (8.2 and CIKM5) defines an epitope with determinants in both domain 1 and domain 2 of FcγRII and lies distant from the Fc binding region, and Clusters 2 (8.26), 3 (IV.3) and 4 (8.7) detect three additional epitopes contained in the second extracellular domain only. All five monoclonal antibodies recognize the heterogenous glycosylated 31 kD rsFcγRII protein. Detection of the rsFcγRII by the mAbs, particularly mAbs from cluster 1 which define a combinatorial epitope, indicates the tertiary structure of rsFcγRII resembles that of the membrane-bound FcγRII. Since the ligand purified rsFcγRII was homogeneous and functional, in that it was purified by binding to IgG aggregates, only this material was used for further studies.

IgG Fc Binding by rsFcγRII

The Fc binding capacity of the purified rsFcγRII was examined by $^{125}I$ radiolabelling the rsFcγRII and immunopurification with HAGG or murine IgG1, IgG2a, IgG2b and IgG3 monoclonal antibodies; monoclonal antibodies 8.26 F(ab') (positive control) and F(ab')$_2$ fragments of 1705 (Fc binding specificity control) were included. SDS-PAGE analysis revealed the same 31 kD protein with the anti-FcγRII mAb 8.26, murine IgG1, IgG2a and HAGG. Binding to murine IgG2b was variable as no binding was detected using the IgG2b mAb, 1480 although another murine IgG2b mAb exhibited some binding (not shown). There was very little binding to IgG3 and no binding to the F(ab')$_2$ fragments of the non-reactive control mAb 1705 indicating that the binding of the purified rsFcγRII to IgG was specifically through the interaction of the Fc portion of IgG with the soluble receptor. The murine IgG binding specificity of the rsFcγRII differs from the membrane-bound human FcγRII; rsFcγRII binds murine IgG2a>IgG1>>IgG2b and IgG3. It should be noted that the HFc3.0 cDNA encodes a histidine at position 131 and poor immunoprecipitation with the murine IgG1 mAb as evidenced would be expected as this is a "low responder" FcδRII (ref 65–69).

The binding of rsFcγRII to immune complexes was demonstrated by its ability to inhibit the binding of EAs to cell surface FcγRII. Incubation of EAs with rsFcγRII completely inhibited the formation of EA rosettes with K562 cells, with a 50% inhibitory final concentration of 20 μg/ml of purified rsFcγRII.

In summary, the physical and functional characteristics of the rsFcγRII are similar to membrane bound FcγRII: (a) rsFcγRII is structurally related to membrane bound FcγRII indicated by intact epitopes for the binding of mAbs to membrane bound FcγRII; (b) rsFcγRII binds IgG through its Fc region, although the murine isotype binding specificity has been altered compared to membrane bound human FcγRII. It is noteworthy that the general characteristics of human FcγγRII in relation to binding specificities of IgG have been derived from studies using few cell types and may not apply in all cases (Van De Winkel et al, 1991, J. Jeuk. Biol. 49: 511).

Blood Clearance and Biodistribution of RsFcγRII

Figure 3C:
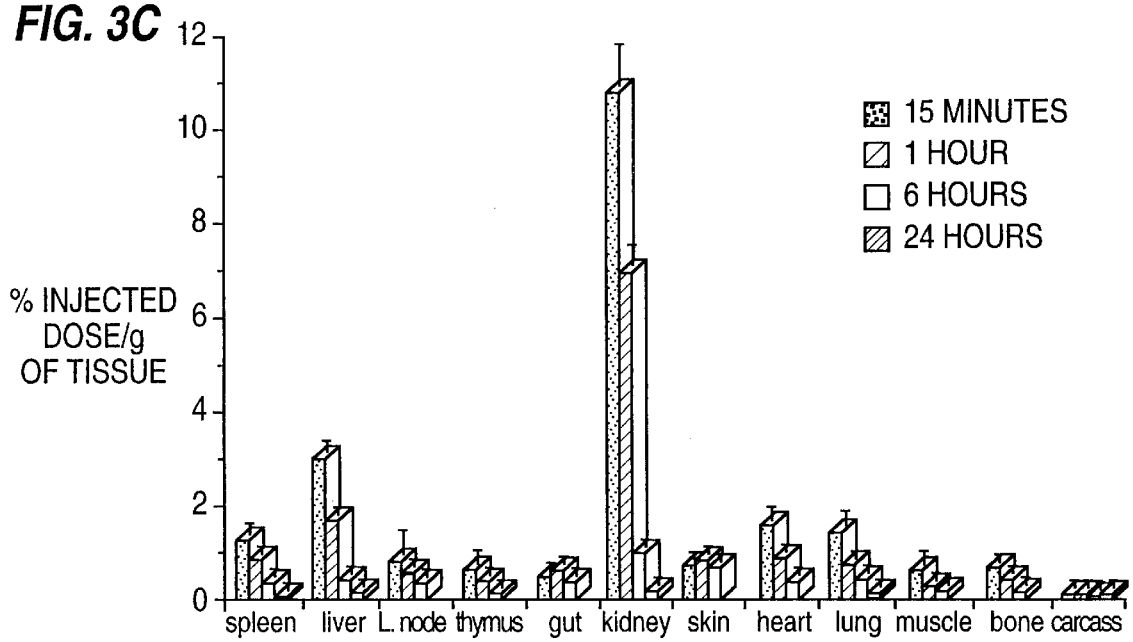

The in-vivo characteristics of rsFcγRII were studied in mice by analyzing the blood clearance and biodistribution of iv administered $^{125}I$-rsFcγRII. The blood clearance studies demonstrate that $^{125}I$-rsFcγRII is rapidly eliminated from the circulation in a biphasic manner with an α-phase t½ of 25 minutes and a β-phase t½ of 4.6 hours; after 24 hours the $^{125}I$-rsFcγRII was totally eliminated (FIG. 3A). Groups of four mice were also injected intravenously and various organs were counted for radioactivity. There was a rapid early concentration of $^{125}I$-rsFcγRII in the kidney at 15 minutes and one hour, with a subsequent fall at six to 24 hours. No other organ exhibited tissue specific accumulation (FIG. 3C). The rapid clearance from the circulation, associated with high concentrations in the kidney, suggested the recombinant protein was excreted predominantly through the kidney, studies of urine demonstrate high levels of $^{125}I$-rsFcγRII at one hour indicating this to be the major route of excretion (FIG. 3B). The effect of route of administration was studied by giving either an ip or iv dose of $^{125}I$-rsFcγRII; and identical pattern of rapid blood clearance was seen with both ip and iv injections (not shown).

Inhibition of the Athus Reaction

Figure 4A:
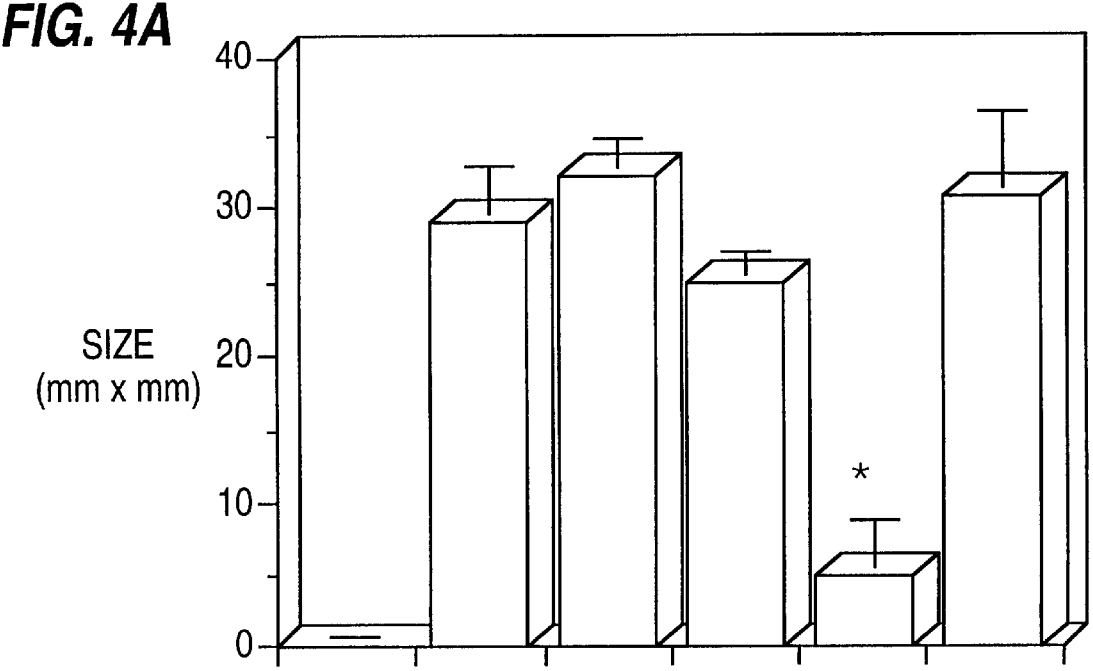
FIGS. 4A–4B. Size (FIG. 4A) and score (FIG. 4B) of the Arthus lesions are shown on the y-axis, using (x-axis); 500 μg of normal rabbit serum (NRS) (n=7), 500 μg of anti-OVA with PBS (n=27), 150 μg of sFc (n=8), 500 μg of rsFcγRII (sFc) (n=6), 500 μg of anti-OVA with 150 μg of KLH (n=4). n=number of injections sites using multiple rats. Error bars represent SE and * indicated p<0.05 compared to the PBS and KLH treated skin.

Rats given iv OVA (5 mg) followed by intradermal rabbit anti-OVA IgG (500 μg) mixed in PBS developed a visible Arthus reaction within two hours of the intradermal injection and at six hours were characterized macroscopically by an erythematous and edematous inflamed area of skin measuring 30 mm$^2$ determined from the width of the lesion in two perpendicular transverse directions (FIG. 4A). Histologically, the tissue section from the site of the lesion showed an inflammatory infiltrate of polymorphonuclear cells, and to a lesser extent mononuclear cells, particularly around venules in the dermis. Specificity of the RPAR was demonstrated by giving rats iv OVA, intradermal rabbit IgG or rsFcγRII all given separately to individual rates, or non-immune rabbit IgG intradermally together with iv OVA; in all cases the RPAR did not develop (not shown).

Figure 4B:
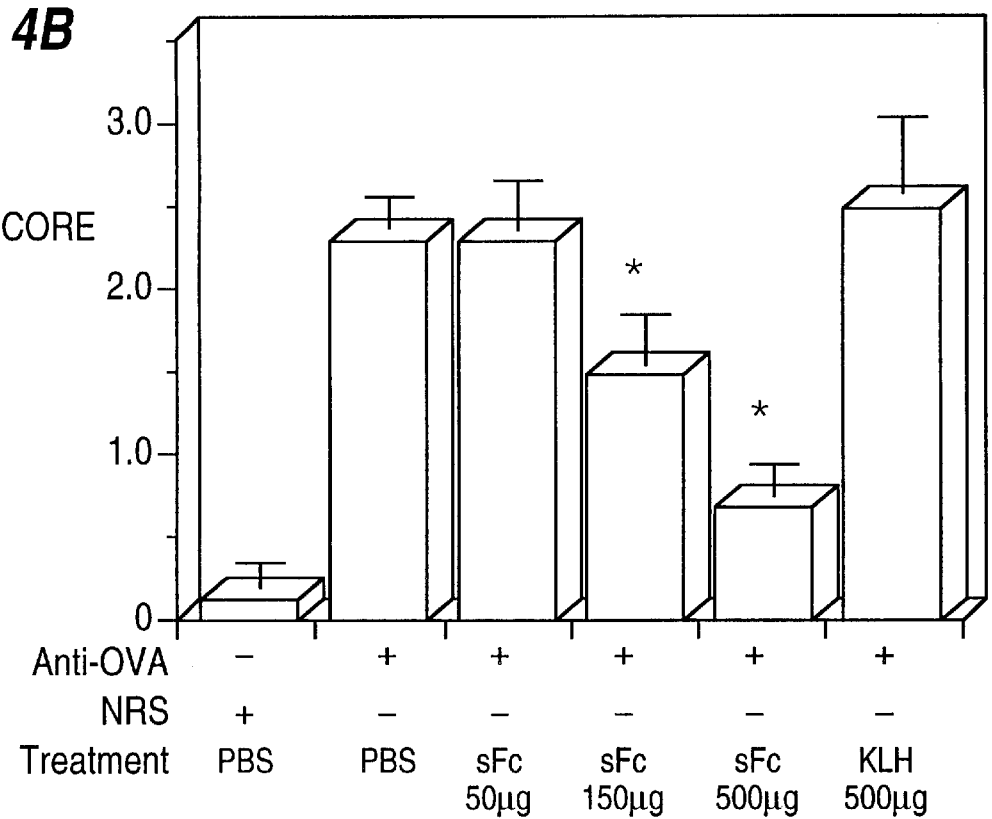

To test the effect of rsFcγRII, OVA injected rats were then given a constant amount of rabbit anti-OVA IgG (500 µg) mixed with rsFcγRII at varying doses (50 to 500 µg) in a final volume of 100 µl intradermally. When rsFcγRII was given with the rabbit anti-OVA IgG, a specific and significant dose-dependent inhibition of the size (using 500 µg of rsFcγRII, p<0.05) and the score (using 500 µg and 150 µg of rsFcγRII, both p<0.05) of the Arthus lesion was observed, compared to PBS treated and KLH (irrelevant protein control) treated lesions (FIG. 4B). The results represent multiple injections using a number of different rats. Histological sections taken from the sites treated the rsFcγRII mixed with the rabbit anti-OVA showed a marked reduction in neutrophil accumulation, margination, infiltration around venules and erythrocyte extravasation compared to PBS treated skin. The mild persistent neutrophil infiltrate in the rsFcγRII treated skin is likely to be a consequence of the short t½ of rsFcγRII and C activation.

The classical Arthus reaction simulates pathogenic mechanisms involved in diverse antibody or immune-complex mediated human diseases as autoimmune disease (including glomerulonephritis, rheumatoid arthritis and systemic lupus erythematosus) and acute rejection. The above data indicates rsFcγRII is a potential therapeutic reagent which may be useful in modifying the inflammatory response in a number of these diseases.

EXAMPLE 4

FcγRII and the FcεRIα chain are structurally related, both have an extracellular region of two Ig like domains, which share 38% amino acid identity, yet are functionally different as FcγRII is a low affinity receptor for IgG, whereas FcεRI is a high affinity receptor for IgE. These characteristics were exploited to localize the FcγRII IgG binding site through the construction of chimeric FcγRII/FcεRI receptors, whereby FcεRI was used as a scaffold to accept homologous regions of FcγRII. Splice overlap extension (SOE) PCR was used to place segments of the FcγRII binding region (Val$^{145}$ to Ser$^{165}$) into the corresponding region of FcεRIm, a chimeric FcεRIα chain comprising the extracellular region of the α chain linked to the transmembrane and cytoplasmic tail of FcγRII which can be expressed on the cell surface independently of associated subunits (Van De Winkel et al, 1990, Scand. J. Immunol. 31: 315). Chimeric receptors were expressed in COS-7 cells and the binding of mouse IgG1 or IgE determined by EA rosetting.

Firstly, the binding site subsequence of FcγRII (Asn$^{154}$ to Ser$^{161}$) was introduced into the corresponding region of FcεRIm. This chimeric receptor (ε154–161γ) bound IgG1 immune complexes, whereas wild type FcεRIm did not; indicating that these eight amino acids contain an IgG1 binding site. This chimeric receptor also had the capacity to bind IgE immune complexes, which was expected based on the identification of IgE binding regions of FcεRI described previously. Replacement of the Asn$^{154}$ to Ser$^{161}$ region of FcγRII with corresponding region of FcεRI(Lys$^{154}$ to Glu$^{161}$) produced a receptor (γ154–161ε) that could not bind IgG1 immune complexes, however could bind IgE (FIG. 1D, E), supporting the finding that the eight residue segment Asn$^{154}$ to Ser$^{161}$ of FcγRII contains an IgG1 binding site, and also identifying the 154 to 161 region of FcεRI as an IgE binding site. To further localize the IgG binding site in the eight residue Asn$^{154}$ to Ser$^{161}$ of FcγRII, three chimeric receptors were constructed, whereby overlapping four residue stretches spanning the 154 to 161 region of FcγII, were replaced in FcγRII by the equivalent regions of FcεRI; (γ154–157ε) FcγRII Asn$^{154}$-Tyr$^{157}$ replaced with FcεRI Lys$^{154}$ to Glu$^{157}$, (γ156–159ε) Gly156 to Leu159 with Trp$^{156}$ to Asp$^{159}$, and (γ158–161ε) Thr$^{158}$ to Ser$^{161}$ with Leu$^{158}$ to Glu$^{161}$. Each of the three chimeric receptors could not bind IgG1 EA, suggesting that the binding region could not be reduced further than the eight residue Asn$^{154}$ to Ser$^{161}$. These receptors were expressed on the cell surface as shown by their ability to bind anti FcγRII mAb.

Figure 5B:
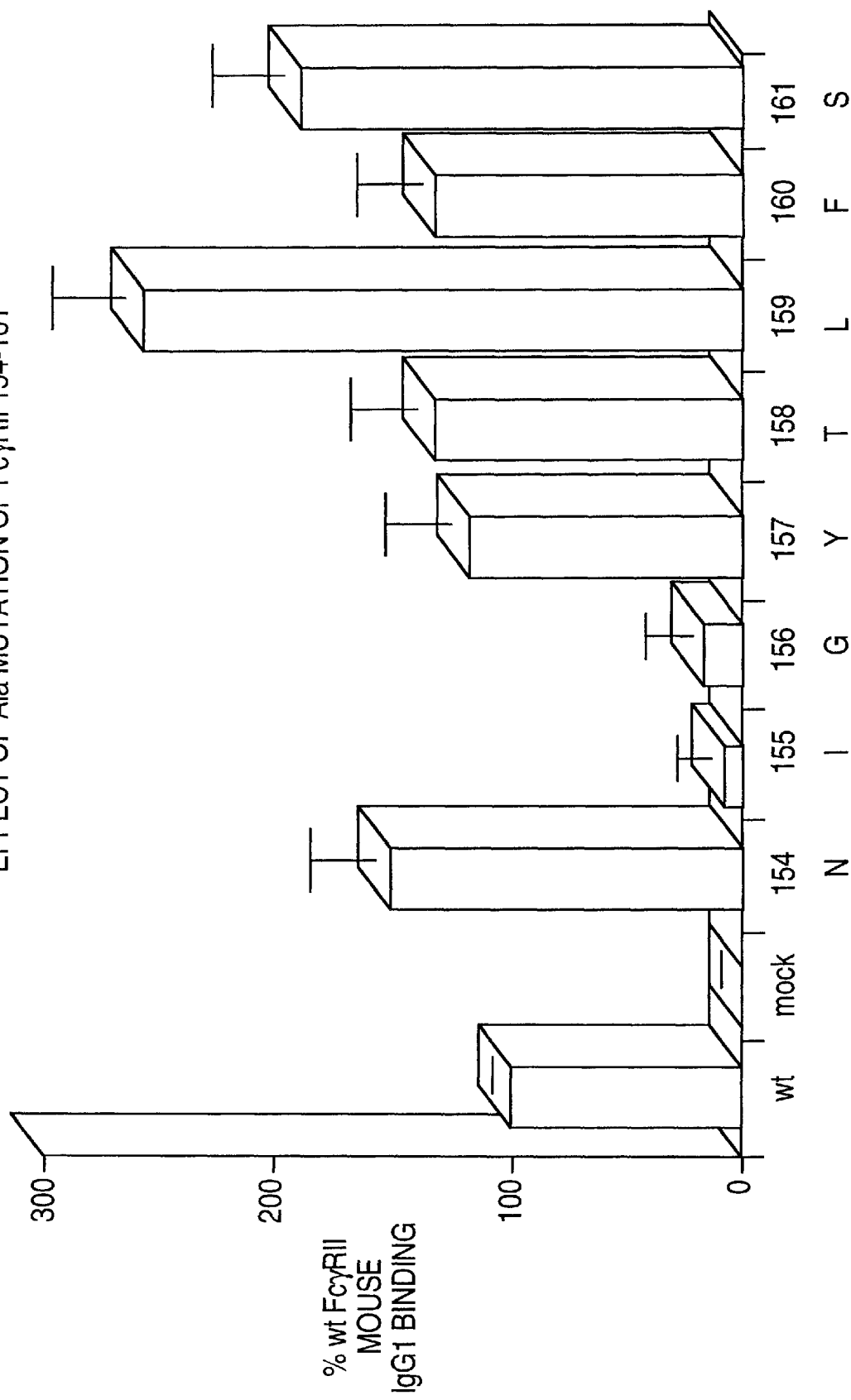

Secondly, to determine the key residues involved in the binding of IgG by FcγRII, site-directed mutagenesis by SOE PCR was used to replace each residue of the Asn$^{154}$ to Ser$^{161}$ region with alanine. These mutant FcγRII were expressed in COS-7 cells and the binding of both mouse and human IgG1 dimers determined (dimers were used to overcome the problem of monomeric IgG not binding to FcγRII with a detectable affinity) (FIGS. 5A and 5B). Levels of cell surface FcγRII expression were determined using an FcγRII mAb 8.2, shown to bind distantly to the binding site (Ieriono et al 1993 J. Immunol), and used to compensate for variable receptor expression between the mutant FcγRII COS cell transfectants. Substitution of Ile$^{155}$ and Gly$^{156}$ destroyed the binding of both human and mouse dimeric IgG1, suggesting that these two residues are crucial for the binding of human and mouse IgG1. Substitution of Asn$^{154}$, Tyr$^{157}$ and Thr$^{158}$ had no significant effect on the binding of human or mouse IgG1 dimers. However, it was interesting to note that replacement of Leu$^{159}$ and Phe$^{160}$ with Ala, increased the binding of human IgG1(ten fold, Affinity 10$^6$M$^{-1}$ to 10$^7$M$^-$1), whereas substitution of Leu$^{159}$ and Ser$^{161}$ with Ala similarly increased the binding of mouse IgG1. Thus, while the primary binding site for human and mouse IgG1 is similar, the fine structure binding the two Ig is different. It should be noted that residue 131 of human FcγRII has been shown to be important for the binding of mouse IgG1 and human IgG2. The presence of Arg or His at position 131 had no effect on the binding of human IgG1, as COS cells expressing either FcγRII Arg$^{131}$ or His$^{131}$ bound human IgG1 with equal efficiency. This indicates that the Asn$^{154}$ to Ser$^{161}$ region of FcγRII is the binding site for human IgG1, and the major binding site for mouse IgG1.

Thirdly, to determine the role of key amino acids of FcεRI with IgE, a similar approach to that described for the analogous of FcγRII was undertaken. Chimeric receptors were generated wherein residues 125 to 131 of FcεRI were used to replace the corresponding amino acids in FcγRII. This chimaera was able to bind IgE whereas wild-type FcγRII was not. In addition, mutagenesis of residues 129 and 131 in FcεRI to alanine profoundly inhibited the binding of IgE to these mutant receptors (see Table 6 and FIG. 12A).

Since residues 154 to 161 of FcεRI (Lys154 to Glu$^{161}$) were shown to be involved in IgE binding—as assessed by the binding of IgE to a chimeric FcR containing these residues, see above (FIG. 12B)—mutagenesis of the residues in this region confirmed that this is indeed a region vital for the binding of IgE.

Alignments of the amino acid sequence of the FcγRII domain with sequences of proteins that are members of the Immunoglobulin Superfamily (IgSF) have demonstrated that it is a member of the IgSF. Domains that are members of this family have a folding pattern of seven β-strands, A–G, in a characteristic β-sheet sandwich structure of two antiparallel ABED and GFC β-sheets. This is true for members of the IgSF C-SET. There are two additional C" and C" strands in the IgSF V-SET domains. A disulfide bond linking the B- and F-strands is characteristics of the IgSF but by no means is it found in all members. A hydrophobic core is the other main contributor to domain stability. Furthermore, it has been postulated that FcγRII belongs to an IgSF subset called the "Truncated C2-SET" which also includes the second domain of CD4 (CD4-2). The folding pattern of CD4-2 was predicted to more resemble that of the V-SET but with a markedly smaller linker region between the C- and E-strands. This was proved to be substantially correct with the determination of the three-dimensional structure of CD4-2 by X-ray analysis. The small peptide linking the C- and E-strands has been designated the C"-strand and it contributes one sidechain, from $Ile^{133}$, to the hydrophobic core. CD4-2 is unusual in that its disulfide bond actually connects the B- and C-strands within the same β-sheet. $Leu^{118}$ replaces the usual IgSF β-strands cysteine, while $Cys^{130}$ replaces the invariant C-strand tryptophan residue.

The alignment of FcγRII and FcεRI sequences with that of CD4-2 (FIGS. 6A and 6B) shows that all three domains are related and are likely to adopt similar folding patterns. This alignment was modified from an automatic sequence alignment according to the established rules for IgSF domains which take into account key features of the IgSF fold such as the C-strand tryptophan, the B/F disulfide bond, the salt bridge and hydrophobic core residues. Unlike CD4-2, FcγRII and FcεRI both appear to have the standard IgSF B/F disulfide bond, which in the case of FcγRII links $Cys^{107}$ and $Cys^{151}$. In addition, FcγRII and FcεRI both have tyrosine residues two residues before the F-strand cysteine which is more typical of the IgSF than the equivalent tryptophan of CD4-2. The $Lys^{136}$ -$Asp^{153}$ salt bridge of CD4-2 is retained in FcγRII but not in FcεRI. $Glu^{86}$ of FcγRII is located in a position which would normally by occupied by a hydrophobic residue which suggests that it must form part of an internal hydrogen or ionic bond. The precise alignments involving the putative Cγ-strand of FcγRII are somewhat arbitrary with $Phe^{129}$ begin designated as the equivalent of CD4 $Ile^{138}$, the hydrophobic core residue in the C"-strand. Computer modelling of FcγRII was carried using the I sight II/Homology and Discover programmes of the protein modelling software package of Biosym Technologies, using a Silicon Graphics Iris4d workstation. Sequences of FcγRII residues aligned with the β-sheet residues of CD4-2 were designated structurally conserved residues (SCR's) with other sequences benign designated as loops. The coordinates for the SCR residues were assigned using the coordinates of the equivalent residues in the Brookhaven PDB file 2CD4 as a template. Using the Homology loop search command, an automated search of the Brookhaven PDB file was then carried out on the loop regions for protein fragments with the correct number of residues and approximately the correct distance between the ends. Ten choices are given. The loop search procedure does not take into account sequence homologies. Since the E/F loops of FcγRII and CD4-2 have the same number of residues, the coordinates of the loop joining the E and F strands of FcγRII were taken directly from CD4-2 E/F section of the 2CD4 PDB file as a "designated loop". The most severe atomic overlaps (>0-0.8 A) were relieved by changing the Ca—Cb torsion angles of the sidechains of the $Phe^{97}$, $Gln^{122}$, $Phe^{136}$ and $Tyr^{157}$ using the Insight II Bumps and Transform commands. Refinement of the resulting structure was performed using the Homology commands Splice Repair, Relax-Loops-All-Atoms and Relax-SCR-All-Sidechains (after building the $Cys^{107}$-$Cys^{151}$ disulfide bond) all of which utilize the Discover molecular dynamics program.

Modelling studies suggest key residues involved in IgG Fc binding are all located in loop regions on the CC"FG face of the domain; $Pro^{114}$ (B/C loop); $Arg^{131}$ (C"/E loop), and first two outside key region $Ile^{155}Gly^{156}$ (F/G loop). Furthermore, these loops are the equivalents to the three CDR loops of an immunoglobulin $V_H$ and $V_L$ domain. According to the model, $Ile^{155}$ and $Gly^{156}$ are located in the groove between the B/C and FIG loops, though still exposed on the CC"FG face of FcγRII. $Ile^{155}$ is deeper in the groove than $Gly^{156}$. The mutation G156A would partially obscure $Ile^{155}$ while the mutation I155A would be much less accessible. As predicted, the carboxyl of $Glu^{86}$ appears to form a hydrogen bond with the hydroxyl of $Ser^{161}$ and this could explain the small effect of the mutation S161A on IgG binding through a minor disruption of the protein structure near the F/G loop. $Pro^{114}$ contributes to this hydrophobic pocket and it should be noted that the equivalent residue to $Pro^{114}$ in FcεRI is $Asp^{114}$ which would conflict with this hydrophobic pocket. In IgG the $C_H2$ hinge proximal has been shown to be an important component of the FcR binding site, and the key sequence is Leu234-Leu235-Gly236-Gly237, complimentary to $Ile^{155}$-$Gly^{156}$ of FcγRII.

EXAMPLE 5

Material and Methods

Chimeric $Fc_\gamma RII/Fc_\epsilon RI$ and mutant $Fc_\gamma RII$ receptor cDNAs and expression constructs: Chimeric $Fc_\gamma RII/Fc_\epsilon RIa$ chain or mutant $Fc_\gamma RII$ cDNAs were constructed by Splice Overlap Extension (SOE) PCR (27) using the $Fc_\gamma RIIa^{NR}$ cDNA (7) as template. SOE PCR was performed as follows: Two PCR reactions were used to amplify the $Fc_\gamma RII$-$Fc_\epsilon RI$ or $Fc_\gamma RII$ fragments to be spliced together. The reactions were performed on 100 ng of the $Fc_\gamma RIIaNR$ cDNA in the presence of 500 ng of each oligonucleotide primer, 1.25 nM dNTPs, 50 nM KCl, 10 mM Tris-Cl pH 8.3 and 1.5 nM $MgCl_2$ using 2.5 units of Taq polymerase (Amplitaq, Cetus) for 25 amplification cycles. A third PCR reaction was performed to splice the two fragments and amplify the spliced product. 100 ng of each fragment (purified by size fractionation through an agarose gel) (28) was used with the appropriate oligonucleotide primers under the above PCR conditions.

The chimeric $Fc_\gamma RII/Fc_\gamma RI$ a chain receptors were generated as follows. Chimera g, e109–116: oligonucleotide pairs (NR1+CHM10SEQ ID NO:32 and 36 ) and (CHM09+EG5, SEQ ID NO:35 and 36) were used to produce two fragments which were spliced together using oligonucleotides NR1 and EG5. Chimera g, e130–135: oligonucleotide pairs (NR1+PM12, SEQ ID NO:32 and 38) and (PM11+EG5, SEQ ID NO:37 and 34) followed NR1 and EG5. The sequence of the oligonucleotide used and their positions of hybridization with the $Fc_\gamma RIIaNR$ cDNA are:

NR1 (SEQ ID NO:32), 5'-TACGAATTCCTATGGAGACCCAAATGTCTC-3', nucleotide position 10–30;

EG5 (, SEQ ID NO:34), 5'-TTTGTCGACCACATGGCATAACG-3', (967–981);

CHM09 (SEQ ID NO:35), 5'-CACATCCCAGTTCCTCCAACCGTGGCACCTCAGCATG-3' (419–437 with nucleotides 442–462 of Fc$_\epsilon$RI a chain); CHM10 (SEQ ID NO:36), 5'-AGGAACTGGGATGTGTACAAGGTCACATTCTTCCAG-3' (462–487 with 446–462 of Fc$_\epsilon$RI a chain), PM11 (SEQ ID NO:37), 5'-GTGGTTCTCATACCAGAATTTCTGGGGATTTTCC-3', (473–490 with 492–506 of Fc$_\epsilon$RI a chain); PM12 (SEQ ID NO:38), 5'-CTGGTATGAGAACCACACCTTCTCCATCCCAC-3' (516–531 with 491–506 of Fc$_\epsilon$RI a chain).

Sequences derived from Fc$_\epsilon$RI a chain are underlined, Fc$_\gamma$RII not underlined; non-homologous sequences including restriction enzyme sites used in cloning of the PCR products are in bold type. Nucleotide positions refer to the previously published Fc$_\gamma$RIIa and Fc$_\epsilon$RI a chain cDNA sequences (7, 13).

The Fc$_\gamma$RII Alanine point mutant cDNAs were generated using the following oligonucleotide combinations. Pro$^{114}$-Ala, (GBC01+EG5, SEQ ID NO:39 and 34 ) and (GBC02+ NR1, SEQ ID NO:40 and 32); Lys$^{113}$-Ala: (GBC03+EG5, SEQ ID NO:41 and 34) and (GBC04+NR1, SEQ ID NO:42 and 32); Leu$^{115}$-Ala, (BGC05 +EG5, SEQ ID NO:43 and 34) and (GBC06 +NR1, SEQ ID NO:44 and 32); Val$^{116}$-Ala, (GBC07+EG5, SEQ ID NO:45 and 34) and GBC08+ NR1, SEQ ID NO:46 and 32); Phe$^{129}$-Ala, (GCE01+EG5, SEQ ID NO:47 and 34) and (GCE02+NR1 , SEQ ID NO:48 and 32); Ser$^{130}$-Ala, (GCE03+EG5, SEQ ID NO:49 and 34) and GCE04+NR1, SEQ ID NO:50 and 32); Arg/His$^{131}$-Ala (GCE05+EG5, SEQ ID NO:51 and 34) and GCE06+NR1, SEQ ID NO:56 and 32); Leu$^{132}$-Ala, (GCE07+EG5, SEQ ID NO:53 and 34) and GCE08+NR1, SEQ ID NO:54 and 32); Asp$^{133}$-Ala, (GCE09+EG5) and (GCE10+NR1, SEQ ID NO:56 and 32); Pro$^{134}$-Ala, (GCE11+EG5, SEQ ID NO:57 and 34) and (GCE12+NR1, SEQ ID NO:58 and 32). Oligonucleotide NR1 and EG5 were used to splice together the two component fragments of each mutant to produce the point substituted cDNAs. The sequence of the oligonucleotides used and their positions of hybridization with the Fc$_\gamma$RIIaNR cDNA are: NR1 and EG5 as described above;

GBC01, SEQ ID NO:39), 5'-GAAGGACAAGGCTCTGGTCAAG-3', (nucleotide position 443–464);
GBC02 (SEQ ID NO:40), 5'-CTTGACCAGAGCCTTGTCCTTC-3', (443–464);
GBC03 (SEQ ID NO:41), 5'-CTGGAAGGACGCTCCTCTGGTC-3', (440–461);
GBC04 (SEQ ID NO:42), 5'-GACCAGAGGAGCGTCCTTCCAG-3', (440–461);
GBC05 (SEQ ID NO:43), 5'-GGACAAGCCTGCTGTCAAGGTC-3', (446–467);
GBC06 (SEQ ID NO:44), 5'-GACCTTGACAGCAGGCTTGTCC-3', (446–467);
GBC07 (SEQ ID NO:45), 5'-GACAAGCCTCTGGCTAAGGTCAC-3', (447–469);
GBC08 (SEQ ID NO:46), 5'-GTGACCTTAGCCAGAGGCTTGTC-3', (447–469);
GCE01 (SEQ ID NO:47), 5'-CCCAGAAAGCTTCCCGTTTGG-3', (490–611);
GCE02 (SEQ ID NO:48), 5'-CCAAACGGGAAGCTTTCTGGG-3', (490–611);
GCE03 (SEQ ID NO:49), 5'-CAGAAATTCGCTCGTTTGGATC-3', (492–614);
GCE04 (SEQ ID NO:50), 5'-GATCCAAACGAGCGATTTCTG-3', (492–614);
GCE05 (SEQ ID NO:51), 5'-GAAATTCTCCGCTTTGGATCCC-3', (494–616);
GCE06 (SEQ ID NO:52), 5'-GGGATCCAAAGCGGAGAATTTC-3', (494–616);
GCE07 (SEQ ID NO:53), 5'-ATTCTCCCGTGCTGATCCCACC-3', (497–619);
GCE08 (SEQ ID NO:54), 5'-GGTGGGATCAGCACGGGAGAAT-3', (497–619);
GCE09 (SEQ ID NO:55), 5'-CTCCCGTTTTGGCTCCCACCTTC-3', (500–622);
GCE10 (SEQ ID NO:56), 5'-GAAGGTGGGAGCCAAACGGGAG-3', (500–622);
GCE11 (SEQ ID NO:57), 5'-CCGTTTGGATGCTACCTTCTCC-3', (503–625);
GCE12 (SEQ ID NO:58), 5'-GGAGAAGGTAGCATCCAAACGG-3', (503–625).

The Ala codon or its complement are shown in bold type.

Chimeric and mutant receptor cDNA expression constructs were produced by subcloning the cDNAs into the eukaryotic expression vector pKC3 (29). Each cDNA was engineered in the PCR reactions to have an EcoRI site at their 5' end (the 5'-flanking oligonucleotide primer NR1 containing an EcoRI recognition site), and a SalI site at their 3' end (the 3'-flanking oligonucleotide primer EG5, containing a SalI recognition site), which enabled the cDNAs to be cloned into the EcoRI and SalI sites of pKC3. The nucleotide sequence integrities of the chimeric cDNAs were determined by dideoxynucleotide chain-termination sequencing (30) using Sequenase™ (United States Biochemical Corp., Cleveland, Ohio) as described (31).

Transfections-COS-7 cells (30–50% confluent per 5cm$^2$ Petri-dish) were transiently transfected with FcR cDNA expression constructs by the DEAE-dextran method (32). Cells were incubated with a transfection mixture (1ml/5cm2 dish) consisting of 5–10 mg/ml DNA, 0.4 mg/ml DEAE-dextran (Pharmacia, Uppsala, Sweden) and 1 mM chloroquine (Sigma, St Louis, Mo.) in Dulbecco's Modified Eagles Medium (DME) (Flow Laboratories, Australia) containing 10% (v:v) Nuserum (Flow Laboratories, Australia), for 4hr. The transfection mixture was then removed, cells treated with 10% (v:v) dimethysulphoxide in Phosphate buffered saline (PBS, 7.6 mM Na$_2$HPO$_4$/3.25 mM NaH$_2$PO$_4$/145 mN NaCl) pH7.4 for 2 min, washed and returned to fully supplemented culture medium for 48–72 hr before use in assays. COS-7 cells were maintained in DME supplemented with 10% (v:v) heat inactivated fetal calf serum, 100 U/ml penicillin, 100 mg/ml streptomycin, 2 mM glutamine (Commonwealth Serum Laboratories, Australia) and 0.05 mM–2-mercaptoethanol (2mE) (Kock Light Ltd., UK).

Monoclonal antibodies and Ig reagents—The anti-Fc$_\gamma$RII mAb 8.2 was produced in this laboratory (19). The mouse IgE anti-TNP mAb (TIB142) was produced from a hybridoma cell line obtained from the American Type Culture Collection (Rockville, M.d.); the mouse IgG1 anti-TNP mAb (A3) was produced from a hybridoma cell line which was a gift of Dr A Lopez (33). Human IgG1 myeloma protein was purified from the serum of a myeloma patient as described (34). Human IgGI oligomers were prepared by chemical crosslinking using S-acetylmercaptosuccinic anhydride (SAMSA) (Sigma, St Louis, Mo.) and N-Succinimidyl 3-(2-pyridyldithio) propionate (SPDP) (Pierce Chemical Company, Rockford, Ill.) as follows: hIgG1 myeloma protein (5 mg at 10 mg/ml) in phosphate buffer (0.01M sodium phosphate pH 7.5/0.15M NaCl) was treated with a 5-fold molar excess of SPDP in dioxine, for 30 min. Excess reagents were removed by dialysis into PBS pH 7.0/2 mM EDTA. The SAMSA modified hIgGi was treated with 200 ml hydroxylamine (1 mM in PBS pH 7.0) for 30 min, then mixed with SPDP modified hIgG1 (1:1 molar ratio) and incubated for a further hr. The reaction was terminated with N-ethylmalemide (Sigma, St Louis, Mo.) added to a final concentration of 6.6 mM (35). All reactions were performed at room temperature. Dimeric hIgG1 was purified from monomeric and oligomeric hIgG1 by size fractionation chromatography on Sephacryl S-300 HR (Pharmacia LKB Biotechnology).

Erythrocyte-Antibody rosetting—COS-7 cell monolayers transfected with FcR expression constructs were incubated with EA complexes, prepared by coating sheep-red blood cells (SRBC) with trinitrobenzene sulphonate (TNBS) (Fluka Chemika, Switzerland) and then sensitising these cells with mouse IgG1 or IgE anti-TNBS mAb (36). Two ml of 2% EAs (v:v) were added per 5 $cm^2$ dish of transfected cells and incubated for 5 minutes at 37° C. Plates were then centrifuged at 500 g for 3 min and placed on ice for 30 min. Unbound EA were removed by washing with L-15 medium modified with glutamine (Flow Laboratories, Australia) and containing 0.5% Bovine serum albumin (BSA).

Direct binding of dimeric-hIgG1 or dimeric-mIgG1—COS-7 cells transfected with FcR expression constructs were harvested, washed in PBS/0.5% BSA and resuspended at 107/ml in L-15 medium/0.5% BSA. 50 ml of cells were incubated with 50ml serial dilutions of $^{125}$I-dimeric-hIgG1 for 120 min at 4° C. $^{125}$I-dimeric-Ig was prepared by the chloramine-T method as described (37) and shown to compete equally with unlabelled dimeric-Ig in binding to Fc receptor expressing COS-7 cells. Cell bound $^{125}$I-dimeric-IgG1 was determined following centrifugation of cells through a 3:2 (v:v) mixture of dibutylphthalate and dioctylphthalate oils (Fluka Chemika, Switzerland) and cell bound $^{125}$I-dimer determined. Non-specific dimer binding was determined by assaying on mock transfected cells and subtracted from total binding to give specific dimeric-IgG1 bound. Levels of cell surface $Fc_{65}$ RII expression were determined using the anti-$Fc_\gamma$RII mAb 8.2, shown to bind distantly to the binding site (19), and used to correct for variable cell surface receptor expression between the mutant FcγRII COS-7 cell transfectants. The binding of 8.2 was determined in a direct binding assay as described for the human IgG1-dimer binding assays.

Results

Chimeric receptors identify multiple regions of $Fc_\gamma$RII involved in IgG binding. In order to determine the roles of domain 1 and the B-C or C'-E loop regions of domain 2 in the binding of IgG by human $Fc_\gamma$RII, chimeric receptors were generated whereby each of these regions in $Fc_\gamma$RII were replaced with the equivalent regions of the human $Fc_\epsilon$RI a chain. Chimeric receptor cDNAs were constructed by SOE PCR, subcloned into the eukaryotic expression vector pKC3 and transiently transfected into COS-7 cells. The IgG binding capacities of the chimeric receptors were determined by both EA rosetting and the direct binding of dimeric hIgG1. The substitution of FcγRII domain 1 with that of the FcεRI α chain produced a receptor (designated $D1_{68}$ $D2_\gamma$) which as expected retained the capacity to bind the highly sensitized IgG-EA complexes (FIG. 7A), however in contrast to the wild-type receptor did not bind dimeric-hIgG1 (FIG. 8). Similarly, the replacement of the region of the $Fc_\gamma$RII α chain comprising residues $Ser^{109}$-$Val^{116}$ (B-C loop) or $Ser^{130}$-$Thr^{135}$ (C'-E loop) of $Fc_{65}$ RII domain 2 with the equivalent regions of the $Fc_\gamma$RI a chain (producing chimeras γ109–116ε and γ130–135ε respectively), also resulted in the loss of hIgG1-dimer binding (FIG. 8), yet these receptors retained the ability to bind IgG-EA complexes (FIG. 7B,C). COS-7 cells transfected with an expressible form of the $Fc_\epsilon$RI α chain (17) did not bind either hIgG1 dimers or IgG-EA (FIG. 7D, FIG. 8). Thus the ability of chimeric $Fc_\gamma$RII containing domain 1 or B-C, C'-E domain 2 substitutions to bind the highly substituted EA complexes but not dimeric-hIgG1, suggests that these receptors bind IgG with a lower affinity than wild-type $Fc_\gamma$RII. These findings demonstrate that although the domain 1 and domain 2 B-C, C'-E regions do not seem to directly bind IgG, they do appear to make a contribution to the binding of IgG by $Fc_\gamma$RII.

Fine structure analysis of the B-C and C'-E loops of $Fc_\gamma$RII domain 2. The contribution of the B-C and C'-E loop regions of $Fc_\gamma$RII to the binding of IgG was determined using a point mutagenesis strategy where individual residues in both the B-C (residues $Lys^{113}$-$Val^{116}$) and C'-E (residues $Phe^{129}$-$Pro^{134}$) loops were replaced with alanine. cDNAs encoding the mutant receptors were also generated using SOE PCR and subcloned into the eukaryotic expression vector pKC3. The resultant expression constructs were transiently transfected into COS-7 cells and the Ig binding capacity of the mutant receptors determined by assessing the binding of dimeric hIgG1. The levels of cell membrane expression of the mutants on the COS-7 cell transfectants were determined using the anti-$Fc_\gamma$RII mAb 8.2 (shown to detect an epitope distant to the binding site) and were comparable to the of the wild-type receptor (see legend FIGS. 9A–9D). The relative capacity of the mutant receptors to bind hIgG1 were determined using the direct binding assay following correction for variation in cell surface expression levels, and expressed as percentage of wild-type $Fc_\gamma$binding.

Figure 9D:
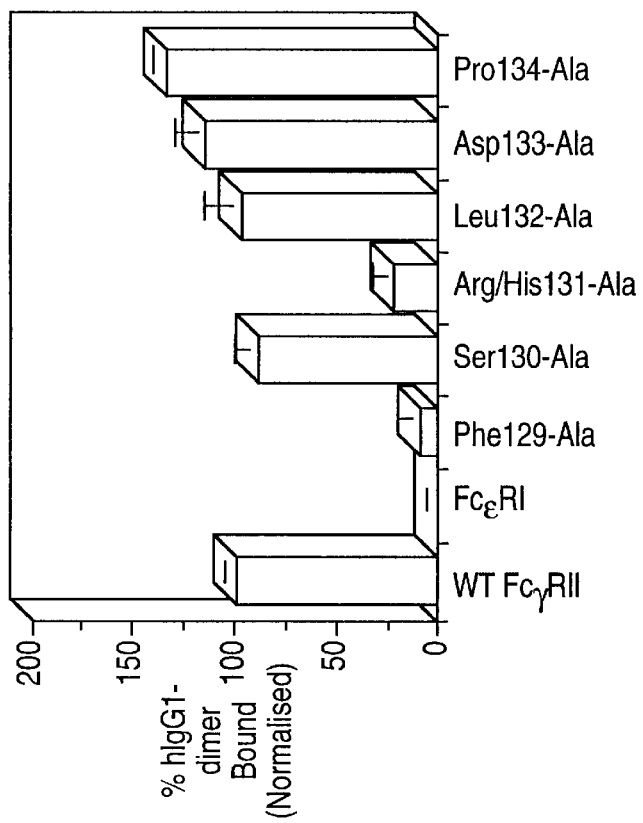
Figure 9C:
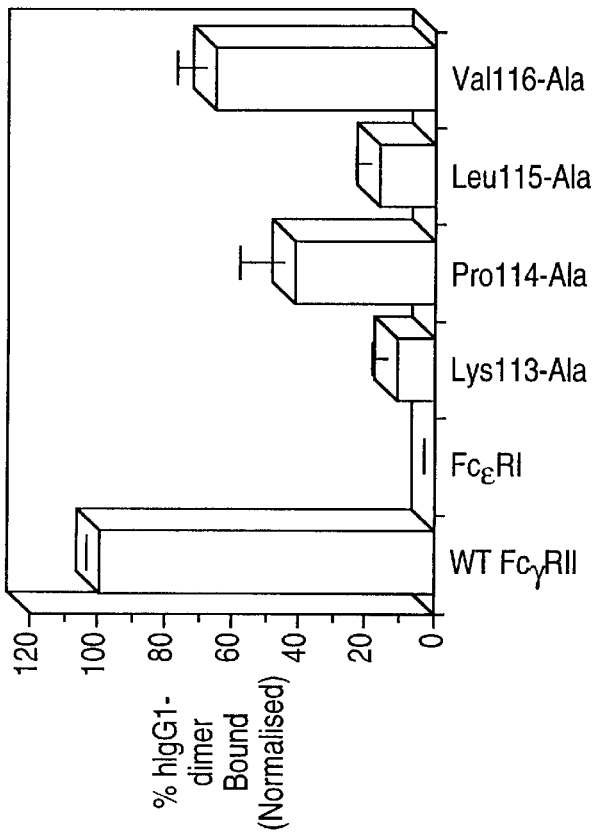
Figure 10:
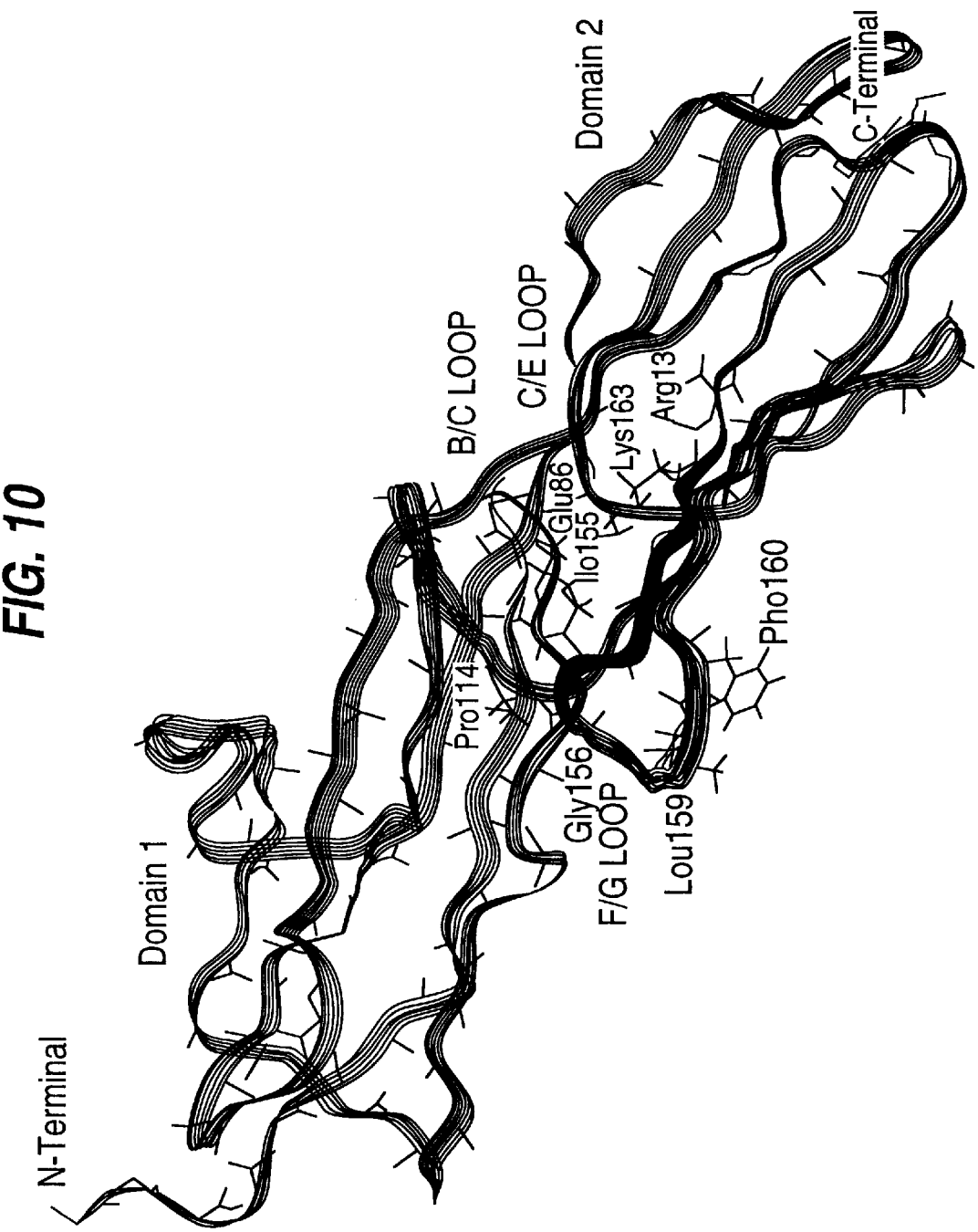
FIG. 10. Molecular model of the extracellular Ig interactive region of Fc$_γ$RII domains 1 and 2 model structure putatively involved in the interaction with IgG1. The position of the loops and G/A strand from domains 1 and 2 are indicated. Examples of residue mutations which alter Fc receptor function such as Phe$^{160}$ and Gly$^{156}$ are also shown.
Figure 13E:
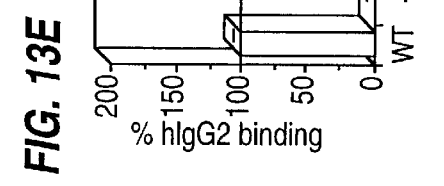
FIGS. 13A–13F. Histogram showing a comparison of Fc receptor mutants binding $IgG_1$ and $IgG_2$.
Figure 13F:
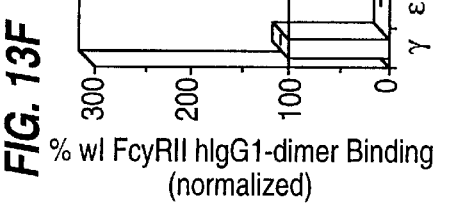
Figure 13C:
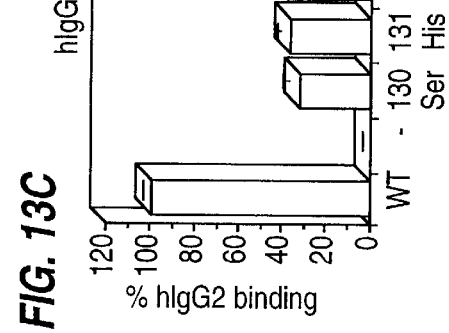
Figure 13D:
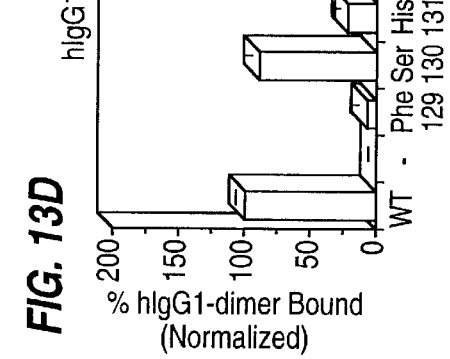
Figure 13A:
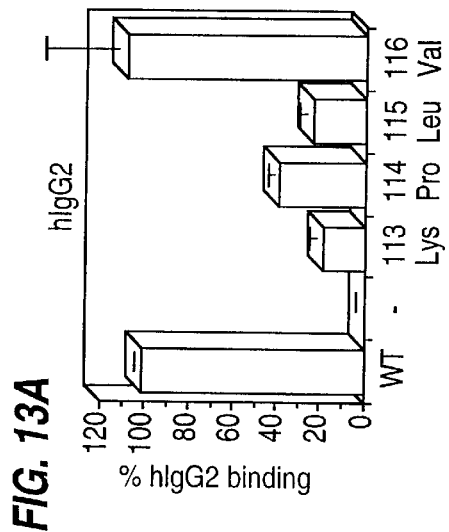
Figure 13B:
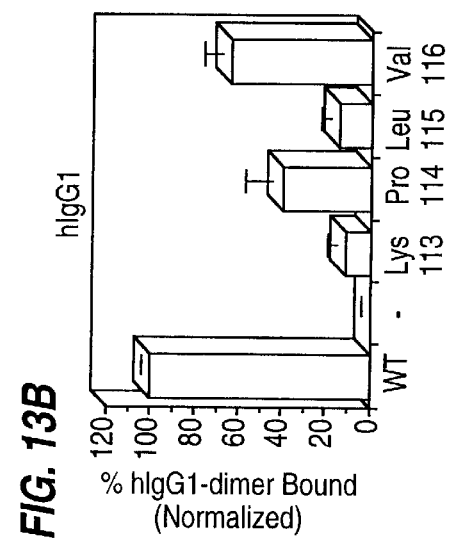
Figure 16B:
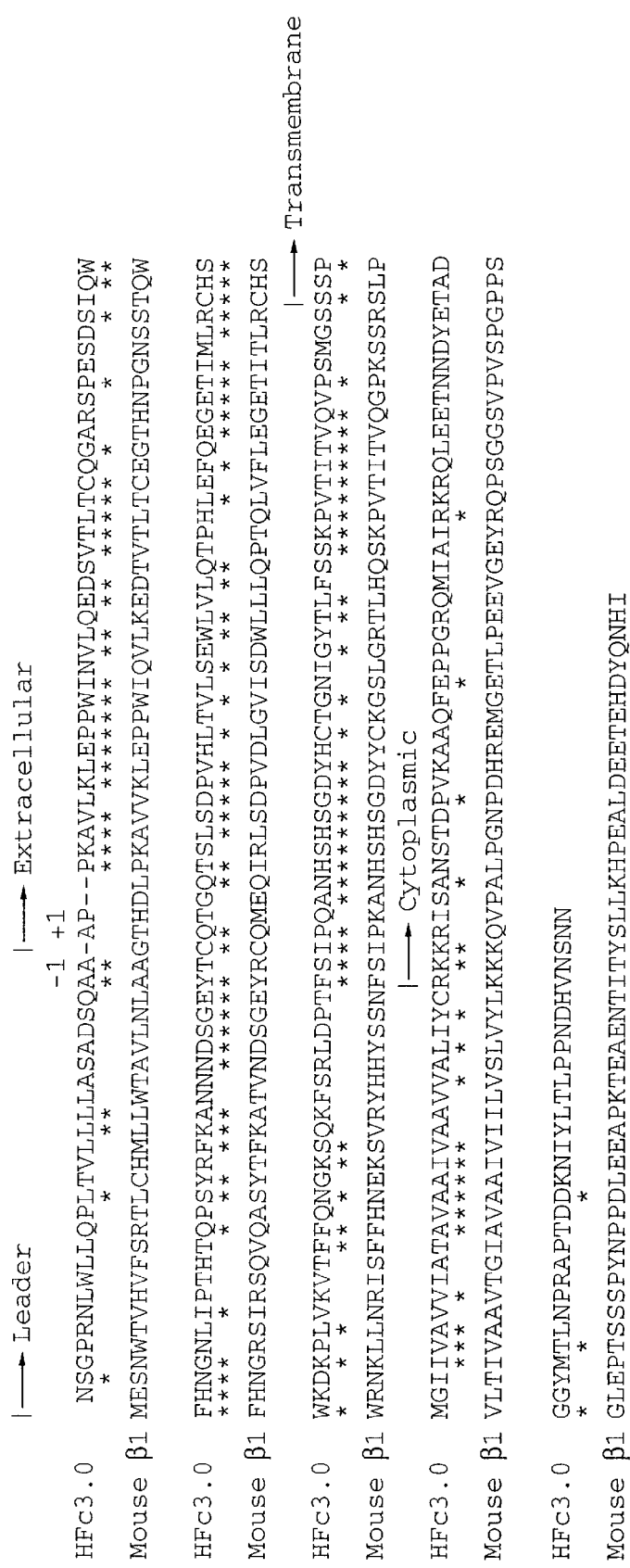

The replacement of the B-C loop residues ($Lys^{113}$, $Pro^{114}$, $Leu^{115}$, $Val^{116}$) in turn with Ala, in each case resulted in diminished hIgG1-dimer binding (FIG. 9C). The most dramatic effect was seen on substitution of $Lys^{113}$ and $Leu^{115}$, which exhibited only 15.9+3.4 (mean+SD) and 20.6+4.0 percent binding compared to wild-type $Fc_\gamma$RII. The replacement of $Pro^{114}$ or $Val^{116}$ with Ala had a lesser effect, these receptors displaying 53.5+13.5 and 73.5+7.9 percent wild-type binding respectively. These results suggest that each of these residues in the B-C loop contribute to the binding of IgG by $Fc_\gamma$RII whether as direct contact residues or indirectly by maintaining the correct conformation of the binding site. Alanine replacement of residues 129 to 134 of the C'-E loop ($Phe^{129}$, $Ser^{130}$, $Arg/His^{131}$, $Leu^{132}$, $Asp^{133}$, $Pro^{134}$) also suggests this region plays a role in the binding of IgG by $Fc_\gamma$RII (FIG. 9D). Substitution of $Phe^{129}$ and $Arg/His^{131}$ decreased hIgG1-dimer binding by over 90% and 80% respectively to 8.2+4.4 and 21.9+3.9 compared to that of wild-type $Fc_\gamma$RII. In contrast, replacement of residues $Asp^{133}$ and $Pro^{134}$ increased binding to 113.5+8.8 and 133.5+0.2 percent of the wild-type receptor. The substitution of $Ser^{130}$ or $Leu^{32}$ with Ala had no significant effect on the binding of hIgG1, as these mutants exhibited comparable binding to wild-type $Fc_\gamma$RII. These findings suggest $Phe^{129}$ and $Arg/His^{131}$ may play an important role in the binding of hIgG1, and the observation that the substitution of $Asp^{133}$ and $Pro^{134}$ increase binding also suggest an important role for these residues, which appears different from $Phe^{129}$ and $Arg/His^{131}$. Again, a distinction between a possible direct binding role or contribution to structural integrity of the receptor cannot be made, however these findings clearly identify both the B-C and C'-E loops as playing a role in the binding of IgG by $Fc_\gamma$RII. The positions of the residues proposed to have binding roles on the putative domain 2 model suggests that it is the region of the B-C-C'-E-F-G face forming the interface with domain 1 that is involved in the contact of $Fc_\gamma$RII with IgG (FIG. 10).

Discussion

The findings presented herein provide evidence to suggest that the interaction of IgG with hFc$_\gamma$RII involves multiple regions of the receptor. Previously, we have described the localization of a single region of hFc$_\gamma$RII capable of directly binding IgG situated in the second extracellular domain between residues Asn$^{154}$ to Ser$^{161}$ (20). Of the entire extracellular region, only the 154–161 segment was demonstrated to directly bind IgG, since insertion of only this region into the corresponding region of the human Fc$_{68}$ RI a chain, imparted IgG binding function to Fc$_\epsilon$RI. Moreover, replacement of this region in Fc$_\gamma$RII with that of Fc$_\epsilon$RIa resulted in loss of IgG binding, implying that residues Asn$^{154}$ to Ser$^{161}$ of Fc$_\gamma$RII comprises the key IgG1 interactive site of hFc$_\gamma$RII. However, the generation of further chimeric hFc$_\gamma$RII/Fc$_\epsilon$RIa receptors as described in this paper has suggested that two additional regions of hFc$_\gamma$RII domain 2, although not directly capable of binding IgG, also influence the binding of IgG by hFc$_\gamma$RII. The replacement of the regions encompassing Ser$^{109}$ to Val$^{116}$ (B-C loop) and Phe$^{129}$ to Pro$^{134}$ (C'-E loop) of hFc$_\gamma$RII with the equivalent regions of the Fc$_\epsilon$RI a chain, produced receptors which despite containing the putative binding site (Asn$^{154}$ to Ser$^{161}$) and retaining the ability to bind IgG-EA, lost the capacity to bind dimeric hIgG1. Indeed, site-directed mutagenesis performed on each individual residue of the 109–116 and 129–134 regions identified a number of residues which appear to play crucial roles in hIg1 binding by Fc$_\gamma$RII. The replacement of Lys$^{113}$, Pro$^{114}$, Leu$^{115}$ and Val$^{116}$ of the B-C loop, and Phe$^{129}$ and Arg/His$^{131}$ of the C'-E loop with alanine, all resulted in diminished hIgG1 binding. Therefore, these findings provide strong evidence to suggest that the B-C and C'-E loops of hFc$_\gamma$RII also contribute to the binding of IgG.

A number of other studies have provided evidence to support the proposed IgG binding roles of the B-C and C'-E loop regions of hFc$_\gamma$RII. Polymorphism studies of mouse and human Fc$_\gamma$RII have implicated residues 114, 131 and 159 in the binding of IgG by Fc$_\gamma$RII. These residues are located in the B-C (114) C'-E (131) and F-G (159) loops respectively. The Ly-17 polymorphism of mouse Fc$_\gamma$RII has been described at the molecular level as two allelic variants (Ly17.1 and Ly17.2) that differ at only residues 116 and 161 (the equivalent of residues 114 and 159 in the human). Monoclonal antibodies specific for the Ly17.2 form inhibit the binding of IgG to the receptor, implying that residues 116 and/or 161 are involved in binding themselves or closely situated to residues crucial in the interaction of Fc$_\gamma$RII with IgG (24, 25). Furthermore, the high responder/low responder polymorphism of hFc$_\gamma$RIIa results in an amino acid substitution at residue 131, which has been shown to influence the binding of mouse IgG1 and human IgG2 (21–23). The findings described herein also suggest the nature of the residue at 131 plays a role in the binding of hIgG1, as replacement with alanine results in a marked reduction in binding of this isotype to hFc$_\gamma$RII. Thus, although the F-G loop of hFc$_\gamma$RII is clearly the major region involved in the direct interaction with IgG, as demonstrated in that only this region has been definitively shown to directly bind IgG (20), residue 131 also appears to play a binding role. However, the question of whether residue 131 is directly participating in IgG binding or providing a secondary or indirect influence remains to be determined.

The molecular model of the entire F$_{c\gamma}$RII shows that the regions involved in Ig binding are located on the same face of domain 2 and at the interface between domains 1 and 2. Furthermore, this also indicates that the A/B and E/F loops of domain 1 as well as the strand connecting domains 1 and 2 (G/A strand) are located in the same region (interdomain interface) and contribute to the binding area of the domain. This area forms a hydrophobic pocket and development of receptor antagonists would be targeted at this region.

Furthermore since Fc$_\gamma$RII and FCεRI as well as other FcR are homologous then their overall structure and general principles of the location of the binding sites would be similar to that disclosed in this application.

The studies described herein demonstrate that domain 1 of hFc$_\gamma$RII, although does not appear to play a direct role in IgG binding, does play an important role in the affinity of IgG binding by hFc$_\gamma$RII. This is suggested as replacement of domain 1 of hFc$_\gamma$RII with domain 1 of hFc$_\epsilon$eRI, reduced the capacity to bind IgG, as shown by the failure of this receptor to bind dimeric hIgG1. These data imply that the IgG binding role of domain 1 is likely to be an influence on receptor conformation, stabilizing the structure of domain 2 to enable efficient IgG binding by hFc$_\gamma$RII. This proposal is consistent with the localization of the IgG binding site of hFc$_\gamma$RII to loop regions in domain 2 at the interface with domain 1. The binding site is therefore in close proximity to domain 1 and as such predicted to be influenced in conformation, presumably by the loop and strand region at the bottom of domain 1 i.e. G strand, and the A-B, E-F and C'-C loops.

Further support for the involvement of the B-C and C'-E loops of hFc$_\gamma$RII domain 2 in the binding of IgG has been provided in the cloning and subsequent Ig binding studies of rat Fc$_\gamma$RIII (38), which is structurally and functionally homologous to Fc$_\gamma$RII. Two rat Fc$_\gamma$RIII isoforms, IIIA and IIIH, which have extensive amino acid differences in their second extracellular domains, have been shown to bind rat and mouse IgG subclasses differently. Both isoforms bind rtIgG1 rtIgG2b and mIgG1, however differ in that only the IIIH form binds rtIgG2b and mIgG2b. Significantly, the amino acid differences between rat Fc$_\gamma$IIIA and IIIH isoforms are situated predominantly in the predicted B-C and C'-E loops of domain 2 (FIG. 10). However, it should be noted that the F-G loop regions of rat Fc$_\gamma$RIIIA and IIIH are almost totally conserved, which together with the observation that both forms bind rtIgG1 rtIgG2 a and mIgG1, is consistent with the proposal that the F-G loop region is the major IgG interactive region, and that the B-C and C'-E loop regions provide supporting binding roles.

It is interesting to note that a number of parallels are also apparent in the molecular basis of the interaction of hFc$_\gamma$RII with IgG and that of hFc$_\epsilon$RI with IgE. The Ig binding roles of the two extracellular domains of hFc$_\epsilon$RI are similar to hFc$_\gamma$RII, with domain 2 responsible for the direct binding of IgE and domain 1 playing a supporting structural role (17,26). Furthermore, as described for hFc$_\epsilon$RII, we and others have also identified multiple IgE binding regions in domain 2 of hFc$_\epsilon$RI. Using chimeric hFc$_\gamma$RII/Fc$_\epsilon$RI receptors we have demonstrated that domain 2 of hFc$_\epsilon$RI contains at least 3 regions each capable of directly binding IgE, as the introduction of the Fc$_\epsilon$RI regions encompassed by residues Trp$^{87}$ to Lys$^{128}$, Tyr$^{129}$ to Asn$^{135}$ and Lys$^{154}$ to Glu$^{161}$ into the corresponding regions of hFc$_\gamma$RII was found to impart IgE binding to hFc$_\gamma$RII (17, 20). A similar study using chimeric Fc$_\gamma$RIII/Fc$_\epsilon$RI receptors has implicated 4 regions of hFc$_\epsilon$RI domain 2 in IgE binding, as the regions Ser$^{93}$ to Phe$^{104}$, Arg$^{111}$ to Glu$^{125}$, Asp$^{123}$ to Ser$^{137}$ and Lys$^{154}$ to Ile$^{167}$ of hFc$_\epsilon$RI when replaced with the corresponding regions of hFc$_\gamma$RIII, resulted in the loss or reduction of IgE binding (40). Taken together, these data suggest at least 4 regions of hFc$_\epsilon$RI domain 2 contribute to the binding of IgE, Ser$^{93}$ to Phe$^{104}$, Arg$^{11}$ to Glu$^{125}$, Tyr$^{129}$ to Asn$^{135}$ and Lys$^{154}$ to Ile$^{167}$. Three of these regions correspond to the 3 regions identified herein as important in the binding of IgG by Fc$_\gamma$RII, Arg$^{111}$ to Glu$^{125}$, Tyr$^{129}$ to Asn$^{135}$ and Lys$^{154}$ to Glu$^{161}$, which encompass the B-C, C'-E and F-G loops respectively. In addition, studies with anti-Fc$_\gamma$RII a chain mAb have indicated the region encompassed by residues 100–115 as containing an epitope of the mAb 15A5, which can completely block the binding of IgE to Fc$_\gamma$RI (41). Thus, as described herein for hFc$_\gamma$RII, these findings implicate the B-C, C'-E and F-G loops juxtaposed in domain 2 at the domain 1 interface, as the crucial IgE interactive region of hFc$_\gamma$RI.

EXAMPLE 6

The IgE Binding Site of Fc$_\gamma$RI

Similar experiments to those described for the IgG receptor Fc$_\gamma$RII were performed on the IgE receptor, Fc$_\gamma$RII.

Three regions of the IgE receptor were the target of mutagenesis experiments. These regions defined by residues 112 to 116, 129 to 134 and 154 to 161 are located in the second domain of Fc$_\epsilon$RI. The experiments where performed wherein individual amino acid residues were mutated to alanine and the effect on IgE binding measured. Mutation of the Fc$_\epsilon$RI was performed by splice overlap extension on described for the Fc$_\gamma$RII using the oligonucleotides shown in FIGS. 11A–11B (SEQ ID NO:95–122).

Mutation of Tyr$^{131}$ or Glu$^{132}$ profoundly decreased the capacity of Fc$_\epsilon$RI to bind IgE (FIG. 12A). By contrast mutation of Trp$^{130}$ resulted in enhancement or improvement of IgE binding by Fc$_\epsilon$RI.

Mutation of the residues in the segment from (and including) residue 154–161 also showed that mutation of Val$^{155}$ completely abated binding and mutation of Leu$^{158}$ or Asp$^{159}$ also decreased IgE binding (FIG. 12B). Furthermore mutation of Trp$^{156}$, Tyr$^{160}$ or Glu$^{161}$ enhanced IgE binding to Fc$_\epsilon$RI. Since domain 1 is also involved in Ig binding and since we have developed a molecular model of Fc$_\gamma$RII and since we know Fc$_\gamma$RII and Fc$_\epsilon$RI are highly related proteins it is likely that similar regions of Fc$_\epsilon$RI domain 1 to those of Fc$_\gamma$RII will be involved in binding i.e. in Fc$_\epsilon$RI the, A/B loop residues Asn$^{10}$ - Asn$^{21}$, C/C' loop, residues Asn$^{42}$ - Glu$^{47}$ and the E/F loop residues Lys$^{59}$- Asp$^{62}$.

On the basis of these studies it is clear that certain residues have a major role in Fc$_\epsilon$R interaction and that manipulation of these residues would be useful in the production of useful pharmaceutical or diagnostic reagents. Thus mutation of Tyr$^{131}$, Glu$^{132}$, Val$^{155}$, Leu$^{158}$, Asp$^{159}$ all decrease IgE binding. Conversely mutation of Trp$^{130}$, Trp$^{156}$, Tyr$^{160}$ or Glu$^{160}$ all improve Fc$_\epsilon$RI function since these mutant receptors are able to bind IgE more effectively then the wild type receptor.

EXAMPLE 7

Comparison of the binding of human IgG1 and IgG2 to the Alanine mutants of FcγRII The binding of human IgG2 was also assessed and some similarities and differences in the nature of mutations that affect binding of IgG1 or IgG2 were observed (FIGS. 13A–13F).

Mutations of Lys$^{113}$, Pro$^{114}$, Leu$^{115}$, Phe$^{129}$, His$^{131}$, I$^{155}$, G$^{156}$ decrease IgG1 and IgG2 binding.

Mutation of Val$^{116}$ decrease IgG1 binding only.

Mutation of Ser$^{130}$, Leu$^{132}$, Asp$^{133}$, Pro$^{134}$, Tyr$^{157}$ reduces IgG2 binding only.

Mutation of Thr$^{158}$ and Leu$^{159}$ also enhances IgG1 and IgG2 binding.

TABLE 2

The N-terminal sequence of the Fc receptor and amino acid sequences (SEQ ID NOS: 59, 61, 63 and 65–73) of Fc receptor peptides:

| Peptide | Sequence |
|---|---|
| NH2-terminal | THDLPKAVVKLEPP |
| L3 | KGSLGRTLHQSK |
| L4 | KPVTITVQGPK |
| L5 | KSVRHHYSS-FSIPK |
| L9 | KAVVKLEPPWIQLVK |
| V4 | ELSTTGGNSG(S)P(V)(K)N |
| V8 | EQTRLSDPVDLGVI |
| V10 | ENTITYSLLKHPE |
| V11 | EAENTITYSLLKHPE |
| V16 | THDLPKAVVKLEP--IQV |
| V17 | THDLPKAVVKLEPPWIQV |
| CNBr-1 | MRNKHLNRIVFL(Q/T)N(Y)(K) |

"-" indicates an unassigned residue
( ) indicates an uncertain assignment

TABLE 3

Amino acid Sequences of lysine-C peptides of the murine Fc
receptor and corresponding nucleotide sequence of oligonucleotide probes.
Oligonucleotide probes were constructed on the basis of codon usage
frequencies and synthesized to be complementary to mRNA:

```
L3 (SEQ ID NO: 61)  (Lys)-Gly-Ser-Leu-Gly-Arg-Thr-Leu-His-Gln-Ser-Lys
Probe 1 (SEQ ID NO: 60) 3' UUC-CCU-AGG-GAC-CCU-UCU-UGG-GAC-GUG-GUC-
AGG UUC 5'

L4 (SEQ ID NO: 63)  (Lys)-Pro-Val-Thr-Ile-Thr-Val-Gln-Gly-Pro-Lys
Probe 3 (SEQ ID NO: 62) 3' UUC-GGU-GAC-UGG-UAG-UGG-GAC-CUC-CUU-GGU-UUC 5'

L5 (SEQ ID NO: 65)  (Lys)-Ser-Val-Arg-Tyr-Gly-Gly-Tyr-Ser-Ser-Ser-Phe-Cys-Ile-Pro-Lys
Probe 2 (SEQ ID NO: 64) 3' UUC-AGG-CAC-USU-AUG-CCU-CCU-AUG-AGG-AGG-AGG-
AAG-ACG-UAG-GGU-UUC 5'
```

TABLE 4

Oligodeoxynucleotide probes used in this study

| Name | Sequence | Corresponding sequence in pFc113 cDNA |
|---|---|---|
| Probe 1.5 (SEQ ID NO: 74) | 5'ACGGGGGCTCGAGTTTGACCACAGCCTTTGGAAGATCATGAGTCCCAG3' | 135–182 |
| Probe 1.6 (SEQ ID NO: 75) | 5'TTCGGGATGCTTGAGGAGTGAGTAGGTGATCGTGTTCTCAGCCTC3' | 956–1000 |
| Probe 1.10 (SEQ ID NO: 76) | 5'GTGGTTGGCTTTGGGGATAGAGAAATTACT3' | 545–574 |
| Probe alpha (SEQ ID NO: 77) | 5'AGGGAGAAAGCAGTGTGGTACCAGAC3' | — |
| Probe beta 1 (SEQ ID NO: 78) | 5'CTGTCTGTACTCACCTACTTCCTCTGGAAG | 821–850 |
| Probe beta 2 (SEQ ID NO: 79) | 5'AGGAGGATTGTCTGGAACCTGCTT3' | — |

Sequences complementary to mRNA
Sequences from this paper and Hibbs et al 1986

TABLE 5

Comparison of Immune Complex Binding and FcR mRNA synthesis

| Cell Line (Type) | FcR mRNA* variant | % EA rosettes** gamma1/ gamma2b | Rabbit Ig | % Ly17+ cells° |
|---|---|---|---|---|
| K36 (T lymphoma) | beta1 | >99 | >99 | >99 |
| WEHI 3B (myelomonocytic) | alpha, beta1 | >99 | >99 | >99 |
| J774 (macrophage) | alpha, beta1, beta2 | >99 | >99 | >99 |
| Transfectants+ | NT | NT | NT | 70 |

*alpha, beta1, beta2 mRNA transcripts detected by Northern analysis using specific oligonucleotide probes (Table 1).
**% EA rosetting cells detected using IgG2b monoclonal anti-TNP antibodies or rabbit IgG anti sheep erythrocytes (see Materials and Methods).
°determined by sheep anti-mouse Ig rosetting wih anti-Ly-17.2 monoclonal antibody. Background levels of rosette formation were determined using an irrelevant antibody and were <5%. These cells are also tested with 2.4G2 antibody and show identical reactions to the Ly-17.2 antibody.
NT = not tested
+ The Pst-1 fragment of the pFc113 cDNA insert was subcloned into pKC3 and transfected into LTA-5 cells using the CaCl₂ method.

TABLE 6

EFFECTS OF MUTATION IN FcϵRI ON IgG BINDING

| Position | Residue* (amino acid) | Mutation* (amino acid) | Effect on IgE binding** (relative to normal FϵRI) |
|---|---|---|---|
| 129 | Y | A | 0 |
| 130 | W | A | ↑ |
| 131 | Y | A | |
| 132 | E | A | |
| 133 | N | A | 0 |
| 134 | H | A | 0 |
| 150 | Y | A | |
| 151 | C | A | |
| 152 | T | A | |
| 153 | G | A | |
| 154 | K | A | 0 |
| 155 | V | A | |
| 156 | W | A | ↑ |
| 157 | Q | A | 0 |
| 158 | L | A | |
| 159 | D | A | |
| 160 | Y | A | ↑ |
| 161 | E | A | ↑ |
| 162 | S | A | |
| 163 | E | A | 0 |

*single letter code
**0 = no change
↑ = increase
= decrease

References

Appella, E. Proc. Natl. Acad. Sci. USA 68: 590–594, 1971.
Anderson, C. L. and Abraham, G. N. J. Immunol. 125: 2735–2741, 1980.
Capron, M., Speigelberg, H. L., Prin, L., Bennich, H., Butterworth, A. E.,
Pierce, R. J., Quassi, M. A. and Capron, A. J. Immun, 132: 462–468, 1984.
Classon, B. J., Tsagaratos, J., McKenzie, I. F. C. and Walker, I. W. Proc. Natl. Acad. Sci. USA 83: 4499–4503, 1986a.
Classon, B. J., Tsagaratos, J., Kirszbaum, L., Maddox, J., Mackay, C. R., Brandon, M. R., McKenzie, I. F. C., and Walker, I. D. Immunogenetics 23: 129–132, 1986b.
Dayhoff, M. O., Barker, W. C., and Hunt, L. T. Methods in Enzymol. 91; 524–545, 1983.
Dickler, H. B. Adv. Immun. 24: 167–215, 1976.
Dickler, H. B. and Sachs, D. H. J. Exp. Med. 140: 779–796, 1974.
Dorrington, K. and Klein, M. In Froese, H. and Paraskeva, F. (Eds). Receptors and Ligands in Intracellular Communications, Vol. 2. Structure and Function of Fc receptors, Marcel Dekker, New York, 1983 pp. . . .
Engelhard, M. and Hilschmann, N. Hoppe-Seyler's Z. Physiol. Chem, 356: 1413–1444, 1975.
Fridman, W. H., Rabourdin-Combe, C., Neauport-Santes, C., and Gisler, R. Immun. Rev. 56: 51–88, 1981.
Gough, N. M., Metcalf, D., Gough, J., Grail, D. and Dunn, A. EMBO Journal 4, 645–653, 1985.
Green, G. A., Plutner, H. and Mellman, I. J. Biol. Chem. 260: 9867–9874, 1985.
Hamperly, J. J., Murray, B. A., Edelman, G. M. and Cunningham, B. Proc. Natl. Acad. Sci. USA 83: 3037–3041, 1986.

Hibbs, M. L., Hogarth, P. M. and McKenzie, I.F.C. Immunogenetics 22: 335–348, 1985.

Hibbs, M. L., Walker, I. D., Kirszbaum, L., Chambers, G. W., Pietersz, G. A., Deacon, N. J., McKenzie, I. F. C. and Hogarth, P. M. Proc. Natl. Acad. Sci. USA. 83: 6980–6984, 1986.

Holmes, K. L., Palfree, R. G. E., Hammerling, U. and Morse, H. C. Proc. Natl. Acad. Sci. USA 82: 7706–7710, 1985.

Hogarth, P. M., Edwards J. McKenzie I. F. C., Soding J. N. and Liew F. J. (1982) J. Immunol 46 135–144.

Hubscher, T. and Eisen, A. H. Int. Arch. Allergy Appl. Immun. 41: 689–699, 1971.

Humes, J. L., Binger, S., Galavage, M., Kuehl. F. A. Wightman, P. D., Dahlgren, M. E., Davies, P. and Bonney, R. J. J. Immun. 124: 2110–2127, 1980.

Hunkapillar M. W., Hewick R. M., Dreyer W. J. 9 Hoodle (1983) Methods Enzymol 91, 399–413.

Kolsch, E., Haubeck, H. and Schuler, W. In Froesse, A. and Paraskevas, F. (Eds) Receptors and Ligands in Intercellular Communication, Vol. 2. Structure and Function of Fc Receptors, Marcel Dekker, New York, 1983, pp 215–231, 1983.

Kulczycki, A., Solanki, L. and Cohen, L. J. Clin. Invest. 68: 1558–1564, 1981.

Kurlander, R. J., Ellison, D. M. and Hall, J. J. Immun. 133: 855–862, 1984.

Leslie, R. G. Q. Eur. J. Immun. 10: 323–346, 1980.

Lopez, A. F. Strath, M. and Sanderson, C. J. Immunology 48: 503–509. 1983.

Maniatis, T., Fritsch, E. F. and Gambrook, J. in Molecular Cloning, A Laboratory Manual, Cold Spring Harbor Laboratory, New York, 1982.

Mantorani, B. J. Immun. 115: 15–17 (1975).

Maxam, A. M. and Gilbert, W. Methods in Enzymol. 65: 499–560 (1980).

Mostov, K. E., Friedlander, M. and Blobel, G. Nature 308: 37–43 (1984).

Nishioka, Y. and Leder, P. J. Biol. Chem, 255: 3691–3694 (1980).

Novotny, J. and Margolies, N. M. Biochem. 22. 1153–1158 (1983).

Ozols, J., Gerard, C. and Stachelek, C. J. Biol. Chem. 252: 5986–5989 (1977).

Parish, C. R. and Haywood, J. A. Proc. Roy. Soc. lond. (Biol.) 187: 47–63 (1974).

Parish, C. R. and McKenzie, I. F. C. J. Immunol. Methods 20: 173–183 (1978).

Perussia, B., Starr, S., Abraham, S., Fanning, V. and Trincheri, G. J. Immunol. 130: 2142–2148 (1983).

Sanger, F., Nicklen, S. and Coulson, A. R. Proc. Natl. Acad. Sci. USA 74: 5463–5467 (1977).

Sjodahl, J. Eur. J. Biochem. 78: 471–490 (1977).

Speigelberg, H. L. Adv. Immun. 35: 61–88 (1985).

Teillaud, J., Diamond, B., Pollock, R. R., Fajtova, V. and Scharff, M. D. J. Immun. 134: 1774–1779 (1985).

Tourvieille, B., Gorman, S. D., Field, E. H., Hunkapiller, T. and Parnes, J. R. Science 234: 610–614 (1986).

Tsay, D. D., Ogden, D. and Schlamowitz, M. J. Immun. 124: 1562–1567 (1980)

Unkless, J. C. J. Exp. Med. 150: 580–596 (1979).

Unkless, J. L., Fleit, H. and Melman, I. S. Adv. Immun. 31: 247–270 (1981).

Winnacker, E. L. and Dorper, T. In Gassen, H. G. and Lang, A. (Eds) Chemical and Enzymatic Synthesis of Gene Fragments: A Laboratory Manual, Verlag Cherrie Weinhein, 1982, pp97–102.

Williams, A. F. Nature 314: 579–580 (1985).

Williams, A. F. and Gagnon, J. Science 216: 696–703 (1982).

Yodoi, J. and Ishizaka, K. J. Immun. 124: 1322–1329 (1980).

A deposit of the material referred to herein as pFc24, pFc113 (ATCC 67414), HFc3.0, HFc3.1 (ATCC 67415) and HFc 3.47 (ATCC 67416) was made with ATCC 12301 Parklawn Drive, Rockville, M.d. 20852 on or about 29th May, 1987 and with Dr. George Hodges of the Cancer Institute (also known as the Peter McCallum Clinic) of 481 Little Lonsdale Street, Melbourne, Victoria, Australia under terms and conditions permitting access to members of the public.

References

1. Unkless, J. C., , E. & Freedman V. H. (1988) Ann. Rev. Immunol. 6, 251–281.
2. Van de Winkel, J. G. J. & Anderson, C. L. (1991) J. Leuk. Biol. 49, 511–524.
3. Ravetch, J. V. & Kinet, J.-P. (1991) Ann. Rev. Immunol. 9, 457–492.
4. Graziano, R. F.& Fanger, M. W. (1987) J. Immunol. 139, 3536–3541.
5. Anderson, C. L., Shen, L., Eicher, D. M., Wewers, M. D. & Gill, J. K. (1990) J. Exp. Med. 171, 1333–1345.
6. Rigley, K. P. & Klaus, G. B. (1989) Eur. J. Immunol. 19, 481
7. Stuart, S. G., Troustine, M., Vaux, T., Koch, T., Martens, C., Mellman, I. & Moore, K. W. (1988) J. Exp. Med. 166, 1668–1684.
8. Hibbs, M. L., Bonadonna, L. Scott, B. M., McKenzie, I. F. C. & Hogarth, P. M. (1988) Proc. Natl. Acad. Sci. (USA) 85, 2240–2244.
9. Stengelin, S., Stamenkovic, I. & Seed, B. (1988) EMBO J. 7, 1053–1059.
10. Brooks, D. G., Qiu, W. Q., Luster, A. D. & Ravetch, J. V. (1989) J. Exp. Med. 170, 1369–1385.
11. Stuart, S. G., Simister, N. E., Clarkson, S. B., Shapino, M. & Mellman, I. (1989) EMBO J. 3657–3666.
12. Allen, J. M. & B. Seed. (1989) Science 243, 378–381.
13. Simmons, D. & Seed B. (1988) Nature 333, 568–570.
14. Ravetch, J. V. & Perussia, B. (1989) J. Exp. Med. 170, 481–491.
15. Shimizu, A., Tepler, I., Bemfrey, P. N., Berenstein, E. H. and Leder P. (1988) Proc. Natl. Acad. Sci USA 85, 1907–1911.
16. Maliszewski, C. R., March, C. J., Shoenbom, M. A., Gimpel, S. & Li, S. (1990) J. Exp. Med. 172, 1665–1672.
17. Hulett, M. D., McKenzie, I. F. C. & Hogarth, P. M. (1993) Eur. J. Immunol. 23, 640–645.
18. Hogarth, P. M., Hulett, M. D., Ierino, F. L. Tate, B., Powell, M. S. & Brinkworth, R. I. (1992) Immunol. Rev. 125, 21–35.
19. Ierino, F. L., Hulett, M. D., McKenzie, I. F. C. & Hogarth, P. M. (1993) J. Immunol. 150, 1794–1799.
20. Hulett, M. D., Witort, E., Brinkworth, R. I., McKenzie, I. F. C. & Hogarth, P. M. (1994) J. Biol. Chem. 269, 15287–15293.
21. Tax, W. J. M., Willems, H. W., Reekers, R. W. Capel, P. J. A. & Koene R. A. P. (1983) Nature 304, 445–447.
22. Warmerdam, P. A., Van de Winkel, J. G. J., Vlug, A., Westerdaal, N. A. L. & Capel, P. J. A. (1992) J. Immunol. 147, 1338–1343.
23. Tate, B. J., Witort, E., McKenzie, I. F. C. & Hogarth, P. M. (1992) Immunol. and Cell Biol. 70, 79–87.
24. Hibbs, M. L., Hogarth, P. M. & McKenzie, I. F. C. (1985) Immunogenetics 22, 335–348.

25. Lah, M., Quelch, K., Deacon, N. J., McKenzie, I. F. C. & Hogarth, P. M. (1990) Immunogenetics 31, 202–206.
26. Robinson, M. W. (1993) J. Biol. Chem. 268, 12736–12743.
27. Horton, R. M., Hunt, H. D., Ho, S. N., Pullin, J. K. & Pearse, L. R. (1988) Gene 77, 61–68.
28. Sambrook, J., Fritsch, E. F., and Maniatis, T. (1989) Molecular cloning: A Laboratory Manual, 2nd Ed., Cold Spring Harbor Laboratory, Cold Spring Harbor, N.Y.
29. Van Doren, K., Hanahan, D., & Gluzman, Y (1984) J. Virol. 50, 606–614.
30. Sanger, F., Nicklen, S., and Coulson, A. R. (1977) Proc. Natl. Acad. Sci. USA 74, 5463–5467.
31. Kraft, R., Tardiff, J., Krauter, K. S. and Leinward, L. A. (1988) Biotechniques 6, 544–547.
32. Seed, B., and Aruffo, A. (1987) Proc. Natl. Acad. Sci. USA 84, 3365–33??.
33. Lopez, A. F., Strath, M. and Sanderson, C. J. (1983) Immunology 48, 503–509.
34. Ey, P. L., Prowse, S. J. and Jenkins, C. R. (1978) Immunochemistry 15, 429–435.
35. Pietersz, G. A., Kanellos, J.& McKenzie, I. F. C. Cancer Res. 48, 4469–4476.
36. Parish, C. R. and Hayward, J. A. (1974) Proc.R. Soc. Lond. (Biol.) 187, 47–56.
37. Harlow, E. and Lane, D. (1988) Labelling antibodies. In Antibodies—A Laboratory Manual. Cold Spring Harbor Laboratories. Cold Spring Harbor, N.Y.
38. Farber, D. L., Giorda, R., Nettleton, M. Y., Trucco, M., Kochan, J. P. & Sears, D. W. (1993) J. Immunol. 150, 4364–4361.
39. Hibbs, M. L., Tolvanen, M. & Carpen, O. (1994). J. Immunol. 152, 4466–4474.
40. Mallimaci, M. A., Chizzonite, R., Griffen, M., Nettleton, M., Hakimi, J., Tsien, W-H. & Kochan, J. P. (1993). J. Biol. Chem. 268, 22079–22083.
41. Riske, F., Hakimi, J., Mallamaci, M., Griffen, M., Pilson, B., Tobkes, N., Lin, P., Danho, W., Kochan, J. & Chizzonite, R. (1991) J. Biol. Chem. 266, 11245–11251.

What is claimed is:

1. A nucleic acid molecule encoding a protein capable of binding the Fc portion of immunoglobulin or a fragment thereof capable of binding the Fc portion of immunoglobulin, wherein the protein is selected from the group consisting of:

a protein comprising the amino acid sequence of a naturally-occurring human FcγRII receptor protein wherein at least one of the amino acid residues corresponding to positions 160, 161, 185, 186, 187 or 188 of SEQ ID NO:83 is replaced with a different amino acid residue and wherein the protein exhibits enhanced IgG binding relative to the naturally-occurring human FcγRII receptor protein; and a protein comprising the amino acid sequence of a naturally-occurring murine FcγR receptor protein wherein at least one of the amino acid residues corresponding to positions 160, 161, 185, 186, 187 or 188 of SEQ ID NO:83 is replaced with a different amino acid residue and wherein the protein exhibits enhanced IgG binding relative to the naturally-occurring murine FcγRβII receptor protein.

2. The nucleic acid molecule according to claim 1, wherein the naturally-occurring human FcγRII receptor protein comprises the amino acid sequence of SEQ ID NO:90.

3. The nucleic acid molecule according to claim 1, wherein the naturally-occurring human FcγR receptor protein comprises the amino acid sequence of SEQ ID NO:91.

4. The nucleic acid molecule according to claim 1, wherein the naturally-occurring murine FcγR receptor protein comprises the amino acid sequence of SEQ ID NO:92.

5. The nucleic acid molecule according to claim 1, wherein the naturally-occurring murine FcγR receptor protein comprises the amino acid sequence of SEQ ID NO:93.

6. The nucleic acid molecule according to claim 1, wherein the naturally-occurring murine FcγR receptor protein comprises the amino acid sequence of SEQ ID NO:94.

7. The nucleic acid molecule according to claim 1, wherein the naturally-occurring human FcγRII receptor protein comprises the amino acid sequence of SEQ ID NO:83.

8. The nucleic acid molecule according to claim 1, wherein the naturally-occurring human FcγRII receptor protein comprises the amino acid sequence of SEQ ID NO:124.

9. The nucleic acid molecule according to claim 1, wherein the naturally-occurring human FcγRII receptor protein comprises the amino acid sequence of SEQ ID NO:130.

10. The nucleic acid molecule according to claim 1, wherein the naturally-occurring human FcγRII receptor protein comprises the amino acid sequence of SEQ ID NO:132.

11. The nucleic acid molecule according to claim 1, wherein the naturally-occurring murine FcγR receptor protein comprises the amino acid sequence of SEQ ID NO:81.

12. The nucleic acid molecule according to claim 1, wherein the naturally-occurring murine FcγR receptor protein comprises the amino acid sequence of SEQ ID NO:134.

13. The nucleic acid molecule according to claim 1, wherein the naturally-occurring murine FcγR receptor protein comprises the amino acid sequence of SEQ ID NO:136.

14. The nucleic acid molecule according to claim 1, wherein the different amino acid residue is a conservative substitution of the naturally-occurring amino acid residue.

15. The nucleic acid molecule according to claim 1, wherein the different amino acid residue is selected from the group consisting of alanine, glycine, serine, and asparagine.

16. The nucleic acid molecule according to claim 1, wherein the different amino acid residue is alanine.

17. The nucleic acid molecule according to claim 1, wherein the protein or fragment thereof encoded by the nucleic acid molecule is able to bind immunoglobulin complex and unable to bind uncomplexed immunoglobulin.

18. The nucleic acid molecule according to claim 1, wherein the protein is a fusion protein.

19. A vector comprising the nucleic acid molecule of claim 1.

20. A host cell transformed with a vector comprising the nucleic acid molecule of claim 1.

21. A method of producing the nucleic acid molecule of claim 1, comprising mutating a nucleic acid molecule encoding a protein selected from the group consisting of a naturally-occurring human FcγRII receptor protein and a naturally-occurring murine FcγR receptor protein, wherein the mutation results in a different amino acid residue at at least one position corresponding to positions 160, 161, 185, 186, 187 or 188 of SEQ ID NO:83.

22. A method of producing a protein exhibiting enhanced IgG binding relative to a naturally-occurring human FcγRII receptor protein or a naturally-occurring murine FcγR receptor protein, comprising (i) causing the nucleic acid molecule of claim 1 to be expressed and (ii) isolating and purifying the expressed protein.

23. A nucleic acid molecule encoding a protein capable of binding the Fc portion of immunoglobulin or a fragment thereof capable of binding the Fc portion of immunoglobulin, wherein the protein comprises the amino acid sequence of a naturally-occurring human FcεRI receptor protein wherein at least one of the amino acid residues corresponding to positions 44, 70, 74 or 75 of SEQ ID NO:89 is replaced with a different amino acid residue and wherein the protein exhibits enhanced IgG binding relative to the naturally-occurring human FcεRI receptor protein.

24. The nucleic acid molecule according to claim 23, wherein the naturally-occurring human FcεRI receptor protein comprises the amino acid sequence of SEQ ID NO:88.

25. The nucleic acid molecule according to claim 23, wherein the naturally-occurring human FcεRI receptor protein comprises the amino acid sequence of SEQ ID NO:89.

26. The nucleic acid molecule according to claim 23, wherein the naturally-occurring human FcεRI receptor protein comprises the amino acid sequence of SEQ ID NO:89.

27. The nucleic acid molecule according to claim 23, wherein the different amino acid residue is a conservative substitution of the naturally-occurring amino acid residue.

28. The nucleic acid molecule according to claim 23, wherein the different amino acid residue is selected from the group consisting of alanine, glycine, serine, and asparagine.

29. The nucleic acid molecule according to claim 23, wherein the different amino acid residue is alanine.

30. The nucleic acid molecule according to claim 23, wherein the protein or fragment thereof encoded by the nucleic acid molecule is able to bind immunoglobulin complex and unable to bind uncomplexed immunoglobulin.

31. The nucleic acid molecule according to claim 23, wherein the protein is a fusion protein.

32. A vector comprising the nucleic acid molecule of claim 23.

33. A host cell transformed with a vector comprising the nucleic acid molecule of claim 23.

34. A method of producing the nucleic acid molecule of claim 23, comprising mutating a nucleic acid molecule encoding a naturally-occurring human FcεRI receptor protein, wherein the mutation results in a different amino acid residue at at least one position corresponding to positions 44, 70, 74 or 75 of SEQ ID NO:89.

35. A method of producing a protein exhibiting enhanced IgE binding relative to a naturally-occurring human FcεRI receptor protein, comprising (i) causing the nucleic acid molecule of claim 23 to be expressed and (ii) isolating and purifying the expressed protein.

36. A protein capable of binding the Fc portion of immunoglobulin or a fragment thereof capable of binding the Fc portion of immunoglobulin wherein the protein is selected from the group consisting of:

a protein comprising the amino acid sequence of a naturally-occurring human FcγRII receptor protein wherein at least one of the amino acid residues corresponding to positions 160, 161, 185, 186, 187 or 188 of SEQ ID NO:83 is replaced with a different amino acid residue and wherein the protein exhibits enhanced IgG binding relative to the naturally-occurring human FcγRII receptor protein; and a protein comprising the amino acid sequence of a naturally-occurring murine FcγR receptor protein wherein at least one of the amino acid residues corresponding to positions 160, 161, 185, 186, 187 or 188 of SEQ ID NO:83 is replaced with a different amino acid residue and wherein the protein exhibits enhanced IgG binding relative to the naturally-occurring murine FcγRβII receptor protein.

37. The protein or fragment thereof according to claim 36, wherein the naturally-occurring human FcγRII receptor protein comprises the amino acid sequence of SEQ ID NO:83.

38. The protein or fragment thereof according to claim 36, wherein the naturally-occurring human FcγRII receptor protein comprises the amino acid sequence of SEQ ID NO:124.

39. The protein or fragment thereof according to claim 36, wherein the naturally-occurring human FcγRII receptor protein comprises the amino acid sequence of SEQ ID NO:130.

40. The protein or fragment thereof according to claim 36, wherein the naturally-occurring human FcγRII receptor protein comprises the amino acid sequence of SEQ ID NO:134.

41. The protein or fragment thereof according to claim 36, wherein the naturally-occurring murine FcγR receptor protein comprises the amino acid sequence of SEQ ID NO:81.

42. The protein or fragment thereof according to claim 36, wherein the naturally-occurring murine FcγR receptor protein comprises the amino acid sequence of SEQ ID NO:134.

43. The protein or fragment thereof according to claim 36, wherein the naturally-occurring murine FcγR receptor protein comprises the amino acid sequence of SEQ ID NO:136.

44. The protein or fragment thereof according to claim 36, wherein the different amino acid residue is a conservative substitution of the naturally-occurring amino acid residue.

45. The protein or fragment thereof according to claim 36, wherein the different amino acid residue is selected from the group consisting of alanine, glycine, serine, and asparagine.

46. The protein or fragment thereof according to claim 36, wherein the different amino acid residue is alanine.

47. The protein or fragment thereof according to claim 36, wherein the protein or fragment thereof is able to bind immunoglobulin complex and unable to bind uncomplexed immunoglobulin.

48. The protein or fragment thereof according to claim 36, wherein the protein is a fusion protein.

49. The protein or fragment thereof according to claim 36, wherein the protein is soluble in aqueous solutions.

50. A pharmaceutical composition comprising the protein of claim 36, together with a pharmaceutically acceptable carrier or diluent.

51. A kit for detecting immunoglobulin, including immune complexes, in a sample, comprising:

the protein or fragment thereof according to claim 36, and means for detecting the binding of immunoglobulin to the protein or fragment.

52. A protein capable of binding the Fc portion of immunoglobulin or a fragment thereof capable of binding the Fc portion of immunoglobulin, wherein the protein comprises the amino acid sequence of a naturally-occurring human FcεRI receptor protein wherein at least one of the amino acid residues corresponding to positions 44, 70, 74 or 75 of SEQ ID NO:89 is replaced with a different amino acid residue and wherein the protein exhibits enhanced IgG binding relative to the naturally-occurring human FcεRI receptor protein.

53. The protein or fragment thereof according to claim 52, wherein the naturally-occurring human FcεRI receptor protein comprises the amino acid sequence of SEQ ID NO:89.

54. The protein or fragment thereof according to claim 52, wherein the different amino acid residue is a conservative substitution of the naturally-occurring amino acid residue.

55. The protein or fragment thereof according to claim 52, wherein the different amino acid residue is selected from the group consisting of alanine, glycine, serine, and asparagine.

56. The protein or fragment thereof according to claim 52, wherein the different amino acid residue is alanine.

57. The protein or fragment thereof according to claim 52, wherein the protein or fragment thereof is able to bind immunoglobulin complex and unable to bind uncomplexed immunoglobulin.

58. The protein or fragment thereof according to claim 52, wherein the protein is a fusion protein.

59. The protein or fragment thereof according to claim 52, wherein the protein is soluble in aqueous solutions.

60. A pharmaceutical composition comprising the protein of claim 52, together with a pharmaceutically acceptable carrier or diluent.

61. A kit for detecting immunoglobulin, including immune complexes, in a sample, comprising:

the protein or fragment thereof according to claim 52, and means for detecting the binding of immunoglobulin to the protein or fragment.

\* \* \* \* \*

SEQUENCE LISTING

```
(1) GENERAL INFORMATION:

(iii) NUMBER OF SEQUENCES: 136

(2) INFORMATION FOR SEQ ID NO:1:

(i) SEQUENCE CHARACTERISTICS:
        (A) LENGTH: 86 base pairs
        (B) TYPE: nucleic acid
        (C) STRANDEDNESS: single
        (D) TOPOLOGY: linear (xi) SEQUENCE DESCRIPTION: SEQ ID NO:1:

ATGCTACTGT GGACAGCCGT GCTAAATCTG CTGCTGGGAC TCATGATCTT CCAAAGGCTG        60

TGGTCAAACT CGAGCCCCCG TGGATC                                            86

(2) INFORMATION FOR SEQ ID NO:2:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (xi) SEQUENCE DESCRIPTION: SEQ ID NO:2:

GAGCAGACCC GCCTCAGCGA CCCTGTAGAT CTGGGAGGAT T                            41

(2) INFORMATION FOR SEQ ID NO:3:

(i) SEQUENCE CHARACTERISTICS:
        (A) LENGTH: 66 base pairs
        (B) TYPE: nucleic acid
        (C) STRANDEDNESS: single
        (D) TOPOLOGY: linear (xi) SEQUENCE DESCRIPTION: SEQ ID NO:3:

AAAGGAAGTC TAGGAAGGAC ACTGCACCAG TCCAAGCCTG TCACCATCAC TGTCCAAGGG        60

CCCAAG                                                                  66

(2) INFORMATION FOR SEQ ID NO:4:

(i) SEQUENCE CHARACTERISTICS:
        (A) LENGTH: 69 base pairs
```

```
        (B) TYPE: nucleic acid
        (C) STRANDEDNESS: single
        (D) TOPOLOGY: linear (xi) SEQUENCE DESCRIPTION: SEQ ID NO:4:

GAGGCTGAGA ACACGATCAC CTACTCACTC CTCAAGCATC CCGAAGCCTT GGATGAAGAA      60

ACAGAGCAT                                                              69

(2) INFORMATION FOR SEQ ID NO:5:

(i) SEQUENCE CHARACTERISTICS:
        (A) LENGTH: 87 base pairs
        (B) TYPE: nucleic acid
        (C) STRANDEDNESS: single
        (D) TOPOLOGY: linear (xi) SEQUENCE DESCRIPTION: SEQ ID NO:5:

ATGGAGAGCA ACTGGACTGT CCATGTGTTC TCACGGACTT TGTGCCATAT GCTACTGTGG      60

ACAGCCGTGC TAAATCTTGC TGCTGGG                                          87

(2) INFORMATION FOR SEQ ID NO:6:

(i) SEQUENCE CHARACTERISTICS:
        (A) LENGTH: 129 base pairs
        (B) TYPE: nucleic acid
        (C) STRANDEDNESS: single
        (D) TOPOLOGY: linear (xi) SEQUENCE DESCRIPTION: SEQ ID NO:6:

TGCGAAGGGA CCCACAACCC TGGGAACTCT TCTACCCAGT GGTTCCACAA TGGGAGGTCC      60

ATCCGGAGCC AGGTCCAAGC CAGCTACACG TTTAAGGCCA CAGTCAATGA CAGTGGAGAA     120

TATCGGTGT                                                             129

(2) INFORMATION FOR SEQ ID NO:7:

(i) SEQUENCE CHARACTERISTICS:
        (A) LENGTH: 135 base pairs
        (B) TYPE: nucleic acid
        (C) STRANDEDNESS: single
        (D) TOPOLOGY: linear (xi) SEQUENCE DESCRIPTION: SEQ ID NO:7:

TGCCATAGCT GGAGGAACAA ACTACTGAAC AGGATCTCGT TCTTCCATAA TGAAAAATCC      60

GTGAGGTATC ATCACTACAG TAGTAATTTC TCTATCCCCA AAGCCAACCA CAGTCACAGT     120

GGGGACTACT ACTGC                                                      135

(2) INFORMATION FOR SEQ ID NO:8:

(i) SEQUENCE CHARACTERISTICS:
        (A) LENGTH: 84 base pairs
        (B) TYPE: nucleic acid
        (C) STRANDEDNESS: single
        (D) TOPOLOGY: linear (xi) SEQUENCE DESCRIPTION: SEQ ID NO:8:

TTACCAGTAT TGACAATTGT GGCTGCTGTC ACTGGGATTG CTGTCGCAGC CATTGTTATT      60

ATCCTAGTAT CCTTGGTCTA TCTC                                             84

(2) INFORMATION FOR SEQ ID NO:9:

(i) SEQUENCE CHARACTERISTICS:
        (A) LENGTH: 285 base pairs
        (B) TYPE: nucleic acid
```

(C) STRANDEDNESS: single
        (D) TOPOLOGY: linear (xi) SEQUENCE DESCRIPTION: SEQ ID NO:9:

AAGAAAAAGC AGGTTCCAGC TCTCCCAGGA AACCCTGATC ACAGGGAAAT GGGAGAAACC        60

CTTCCAGAGG AAGTAGGTGA GTACAGACAG CCCTCTGGGG GCTCAGTGCC TGTCAGCCCA       120

GGGCCTCCAT CTGGACTGGA GCCAACAAGC AGCAGCCCAT ACAATCCTCC TGATCTGGAA       180

GAAGCTCCCA AAACTGAGGC TGAGAACACG ATCACCTACT CACTCCTCAA GCATCCCGAA       240

GCCTTGGATG AAGAAACAGA GCATGATTAC CAAAACCACA TTTAG                      285

(2) INFORMATION FOR SEQ ID NO:10:

(i) SEQUENCE CHARACTERISTICS:
        (A) LENGTH: 81 base pairs
        (B) TYPE: nucleic acid
        (C) STRANDEDNESS: single
        (D) TOPOLOGY: linear (xi) SEQUENCE DESCRIPTION: SEQ ID NO:10:

AATTCCGGTC CCAGAAACCT GTGGCTGCTT CAACCATTGA CAGTTTTGCT GCTGCTGGCT        60

TCTGCAGACA GTCAAGCTGC A                                                 81

(2) INFORMATION FOR SEQ ID NO:11:

(i) SEQUENCE CHARACTERISTICS:
        (A) LENGTH: 129 base pairs
        (B) TYPE: nucleic acid
        (C) STRANDEDNESS: single
        (D) TOPOLOGY: linear (xi) SEQUENCE DESCRIPTION: SEQ ID NO:11:

TGCCAGGGGG CTCGCAGCCC TGAGAGCGAC TCCATTCAGT GGTTCCACAA TGGGAATCTC        60

ATTCCCACCC ACACGCAGCC CAGCTACAGG TTCAAGGCCA ACAACAATGA CAGCGGGGAG       120

TACACGTGC                                                              129

(2) INFORMATION FOR SEQ ID NO:12:

(i) SEQUENCE CHARACTERISTICS:
        (A) LENGTH: 135 base pairs
        (B) TYPE: nucleic acid
        (C) STRANDEDNESS: single
        (D) TOPOLOGY: linear (xi) SEQUENCE DESCRIPTION: SEQ ID NO:12:

TGCCACAGCT GGAAGGACAA GCCTCTGGTC AAGGTCACAT TCTTCCAGAA TGGAAAATCC        60

CAGAAATTCT CCCGTTTGGA TCCCACCTTC TCCATCCCAC AAGCAAACCA CAGTCACAGT       120

GGTGATTACC ACTGC                                                       135

(2) INFORMATION FOR SEQ ID NO:13:

(i) SEQUENCE CHARACTERISTICS:
        (A) LENGTH: 84 base pairs
        (B) TYPE: nucleic acid
        (C) STRANDEDNESS: single
        (D) TOPOLOGY: linear (xi) SEQUENCE DESCRIPTION: SEQ ID NO:13:

TCACCAATGG GGATCATTGT GGCTGTGGTC ATTGCTACTG CTGTAGCAGC CATTGTTGCT        60

GCTGTAGTGG CCTTGATCTA CTGC                                              84

(2) INFORMATION FOR SEQ ID NO:14:

(i) SEQUENCE CHARACTERISTICS:
        (A) LENGTH: 216 base pairs
        (B) TYPE: nucleic acid
        (C) STRANDEDNESS: single
        (D) TOPOLOGY: linear (xi) SEQUENCE DESCRIPTION: SEQ ID NO:14:

```
AGGAAAAAGC GGATTTCAGC CAATTCCACT GATCCTGTGA AGGCTGCCCA ATTTGAGCCA      60

CCTGGACGTC AAATGATTGC CATCAGAAAG AGACAACTTG AAGAAACCAA CAATGACTAT     120

GAAACAGCTG ACGGCGGCTA CATGACTCTG AACCCCAGGG CACCTACTGA CGATAAAAAC     180

ATCTACCTGA CTCTTCCTCC CAACGACCAT GTCAAC                               216
```

(2) INFORMATION FOR SEQ ID NO:15:

(i) SEQUENCE CHARACTERISTICS:
        (A) LENGTH: 78 base pairs
        (B) TYPE: nucleic acid
        (C) STRANDEDNESS: single
        (D) TOPOLOGY: linear (xi) SEQUENCE DESCRIPTION: SEQ ID NO:15:

```
ACAGGAAACA TAGGCTACAC GCTGTTCTCA TCCAAGCCTG TGACCATCAC TGTCCAAGTG      60

CCCAGCATGG GCAGCTCT                                                    78
```

(2) INFORMATION FOR SEQ ID NO:16:

(i) SEQUENCE CHARACTERISTICS:
        (A) LENGTH: 29 amino acids
        (B) TYPE: amino acid
        (C) STRANDEDNESS: single
        (D) TOPOLOGY: linear (xi) SEQUENCE DESCRIPTION: SEQ ID NO:16:

```
Met Leu Leu Trp Thr Ala Val Leu Asn Leu Ala Ala Gly Thr His Asp
 1               5                  10                  15

Leu Pro Lys Ala Val Val Lys Leu Glu Pro Pro Trp Ile
             20                  25
```

(2) INFORMATION FOR SEQ ID NO:17:

(i) SEQUENCE CHARACTERISTICS:
        (A) LENGTH: 14 amino acids
        (B) TYPE: amino acid
        (C) STRANDEDNESS: single
        (D) TOPOLOGY: linear (xi) SEQUENCE DESCRIPTION: SEQ ID NO:17:

```
Glu Gln Thr Arg Leu Ser Asp Pro Val Asp Leu Gly Val Ile
 1               5                  10
```

(2) INFORMATION FOR SEQ ID NO:18:

(i) SEQUENCE CHARACTERISTICS:
        (A) LENGTH: 22 amino acids
        (B) TYPE: amino acid
        (C) STRANDEDNESS: single
        (D) TOPOLOGY: linear (xi) SEQUENCE DESCRIPTION: SEQ ID NO:18:

```
Lys Gly Ser Leu Gly Arg Thr Leu His Gln Ser Lys Pro Val Thr Ile
 1               5                  10                  15

Thr Val Gln Gly Pro Lys
             20
```

(2) INFORMATION FOR SEQ ID NO:19:

(i) SEQUENCE CHARACTERISTICS:
        (A) LENGTH: 23 amino acids
        (B) TYPE: amino acid
        (C) STRANDEDNESS: single
        (D) TOPOLOGY: linear (xi) SEQUENCE DESCRIPTION: SEQ ID NO:19:

Glu Ala Glu Asn Thr Ile Thr Tyr Ser Leu Leu Lys His Pro Glu Ala
    1              5                    10                15

Leu Asp Glu Glu Thr Glu His
                  20

(2) INFORMATION FOR SEQ ID NO:20:

(i) SEQUENCE CHARACTERISTICS:
        (A) LENGTH: 29 amino acids
        (B) TYPE: amino acid
        (C) STRANDEDNESS: single
        (D) TOPOLOGY: linear (xi) SEQUENCE DESCRIPTION: SEQ ID NO:20:

Met Glu Ser Asn Trp Thr Val His Val Phe Ser Arg Thr Leu Cys His
    1              5                    10                15

Met Leu Leu Trp Thr Ala Val Leu Asn Leu Ala Ala Gly
                  20                   25

(2) INFORMATION FOR SEQ ID NO:21:

(i) SEQUENCE CHARACTERISTICS:
        (A) LENGTH: 43 amino acids
        (B) TYPE: amino acid
        (C) STRANDEDNESS: single
        (D) TOPOLOGY: linear (xi) SEQUENCE DESCRIPTION: SEQ ID NO:21:

Cys Glu Gly Thr His Asn Pro Gly Asn Ser Ser Thr Gln Trp Phe His
    1              5                    10                15

Asn Gly Arg Ser Ile Arg Ser Gln Val Gln Ala Ser Tyr Thr Phe Lys
                  20                   25                30

Ala Thr Val Asn Asp Ser Gly Glu Tyr Arg Cys
                  35                   40

(2) INFORMATION FOR SEQ ID NO:22:

(i) SEQUENCE CHARACTERISTICS:
        (A) LENGTH: 45 amino acids
        (B) TYPE: amino acid
        (C) STRANDEDNESS: single
        (D) TOPOLOGY: linear (xi) SEQUENCE DESCRIPTION: SEQ ID NO:22:

Cys His Ser Trp Arg Asn Lys Leu Leu Asn Arg Ile Ser Phe Phe His
    1              5                    10                15

Asn Glu Lys Ser Val Arg Tyr His His Tyr Ser Ser Asn Phe Ser Ile
                  20                   25                30

Pro Lys Ala Asn His Ser His Ser Gly Asp Tyr Tyr Cys
                  35                   40                45

(2) INFORMATION FOR SEQ ID NO:23:

(i) SEQUENCE CHARACTERISTICS:
        (A) LENGTH: 28 amino acids (B) TYPE: amino acid
        (C) STRANDEDNESS: single
        (D) TOPOLOGY: linear (xi) SEQUENCE DESCRIPTION: SEQ ID NO:23:

Leu Pro Val Leu Thr Ile Val Ala Ala Val Thr Gly Ile Ala Val Ala
    1               5                   10                  15

Ala Ile Val Ile Ile Leu Val Ser Leu Val Tyr Leu
                20                  25

(2) INFORMATION FOR SEQ ID NO:24:

(i) SEQUENCE CHARACTERISTICS:
        (A) LENGTH: 94 amino acids
        (B) TYPE: amino acid
        (C) STRANDEDNESS: single
        (D) TOPOLOGY: linear (xi) SEQUENCE DESCRIPTION: SEQ ID NO:24:

Lys Lys Lys Gln Val Pro Ala Leu Pro Gly Asn Pro Asp His Arg Glu
    1               5                   10                  15

Met Gly Glu Thr Leu Pro Glu Glu Val Gly Glu Tyr Arg Gln Pro Ser
                20                  25                  30

Gly Gly Ser Val Pro Val Ser Pro Gly Pro Pro Ser Gly Leu Glu Pro
                35                  40                  45

Thr Ser Ser Pro Tyr Asn Pro Pro Asp Leu Glu Glu Ala Pro Lys
        50                  55                  60

Thr Glu Ala Glu Asn Thr Ile Thr Tyr Ser Leu Leu Lys His Pro Glu
    65                  70                  75                  80

Ala Leu Asp Glu Glu Thr Glu His Asp Tyr Gln Asn His Ile
                    85                  90

(2) INFORMATION FOR SEQ ID NO:25:

(i) SEQUENCE CHARACTERISTICS:
        (A) LENGTH: 26 amino acids
        (B) TYPE: amino acid
        (C) STRANDEDNESS: single
        (D) TOPOLOGY: linear (xi) SEQUENCE DESCRIPTION: SEQ ID NO:25:

Asn Ser Gly Pro Arg Asn Leu Trp Leu Leu Gln Pro Leu Thr Val Leu
    1               5                   10                  15

Leu Leu Ala Ser Ala Asp Ser Gln Ala Ala
                20                  25

(2) INFORMATION FOR SEQ ID NO:26:

(i) SEQUENCE CHARACTERISTICS:
        (A) LENGTH: 43 amino acids
        (B) TYPE: amino acid
        (C) STRANDEDNESS: single
        (D) TOPOLOGY: linear (xi) SEQUENCE DESCRIPTION: SEQ ID NO:26:

Cys Gln Gly Ala Arg Ser Pro Glu Ser Asp Ser Ile Gln Trp Phe His
    1               5                   10                  15

Asn Gly Asn Leu Ile Pro Thr His Thr Gln Pro Ser Tyr Arg Phe Lys
                20                  25                  30

Ala Asn Asn Asn Asp Ser Gly Glu Tyr Thr Cys
                35                  40

(2) INFORMATION FOR SEQ ID NO:27:

(i) SEQUENCE CHARACTERISTICS:
    (A) LENGTH: 45 amino acids
    (B) TYPE: amino acid
    (C) STRANDEDNESS: single
    (D) TOPOLOGY: linear (xi) SEQUENCE DESCRIPTION: SEQ ID NO:27:

Cys His Ser Trp Lys Asp Lys Pro Leu Val Lys Val Thr Phe Phe Gln
1               5                   10                  15

Asn Gly Lys Ser Gln Lys Phe Ser Arg Leu Asp Pro Thr Phe Ser Ile
                20                  25                  30

Pro Gln Ala Asn His Ser His Ser Gly Asp Tyr His Cys
                35                  40                  45

(2) INFORMATION FOR SEQ ID NO:28:

(i) SEQUENCE CHARACTERISTICS:
        (A) LENGTH: 28 amino acids
        (B) TYPE: amino acid
        (C) STRANDEDNESS: single
        (D) TOPOLOGY: linear (xi) SEQUENCE DESCRIPTION: SEQ ID NO:28:

Ser Pro Met Gly Ile Ile Val Ala Val Val Ile Ala Thr Ala Val Ala
1               5                   10                  15

Ala Ile Val Ala Ala Val Val Ala Leu Ile Tyr Cys
                20                  25

(2) INFORMATION FOR SEQ ID NO:29:

(i) SEQUENCE CHARACTERISTICS:
        (A) LENGTH: 75 amino acids
        (B) TYPE: amino acid
        (C) STRANDEDNESS: single
        (D) TOPOLOGY: linear (xi) SEQUENCE DESCRIPTION: SEQ ID NO:29:

Arg Lys Lys Arg Ile Ser Ala Asn Ser Thr Asp Pro Val Lys Ala Ala
1               5                   10                  15

Gln Phe Glu Pro Pro Gly Arg Gln Met Ile Ala Ile Arg Lys Arg Gln
                20                  25                  30

Leu Glu Glu Thr Asn Asn Asp Tyr Glu Thr Ala Asp Gly Gly Tyr Met
                35                  40                  45

Thr Leu Asn Pro Arg Ala Pro Thr Asp Asp Lys Asn Ile Tyr Leu Thr
                50                  55                  60

Leu Pro Pro Asn Asp His Val Asn Ser Asn Asn
65                  70                  75

(2) INFORMATION FOR SEQ ID NO:30:

(i) SEQUENCE CHARACTERISTICS:
        (A) LENGTH: 26 amino acids
        (B) TYPE: amino acid
        (C) STRANDEDNESS: single
        (D) TOPOLOGY: linear (xi) SEQUENCE DESCRIPTION: SEQ ID NO:30:

Thr Gly Asn Ile Gly Tyr Thr Leu Phe Ser Ser Lys Pro Val Thr Ile
1               5                   10                  15

Thr Val Gln Val Pro Ser Met Gly Ser Ser
                20                  25

(2) INFORMATION FOR SEQ ID NO:31:

(i) SEQUENCE CHARACTERISTICS:
       (A) LENGTH: 5 amino acids
       (B) TYPE: amino acid
       (C) STRANDEDNESS: single
       (D) TOPOLOGY: linear (xi) SEQUENCE DESCRIPTION: SEQ ID NO:31:

Gly Xaa Tyr Xaa Cys
   1               5

(2) INFORMATION FOR SEQ ID NO:32:

(i) SEQUENCE CHARACTERISTICS:
       (A) LENGTH: 30 base pairs
       (B) TYPE: nucleic acid
       (C) STRANDEDNESS: single
       (D) TOPOLOGY: linear (xi) SEQUENCE DESCRIPTION: SEQ ID NO:32:

TACGAATTCC TATGGAGACC CAAATGTCTC                                     30

(2) INFORMATION FOR SEQ ID NO:33:

(i) SEQUENCE CHARACTERISTICS:
       (A) LENGTH: 30 base pairs
       (B) TYPE: nucleic acid
       (C) STRANDEDNESS: single
       (D) TOPOLOGY: linear (xi) SEQUENCE DESCRIPTION: SEQ ID NO:33:

CATTCTAGAC TATTGGACAG TGATGGTCAC                                     30

(2) INFORMATION FOR SEQ ID NO:34:

(i) SEQUENCE CHARACTERISTICS:
       (A) LENGTH: 23 base pairs
       (B) TYPE: nucleic acid
       (C) STRANDEDNESS: single
       (D) TOPOLOGY: linear (xi) SEQUENCE DESCRIPTION: SEQ ID NO:34:

TTTGTCGACC ACATGGCATA ACG                                            23

(2) INFORMATION FOR SEQ ID NO:35:

(i) SEQUENCE CHARACTERISTICS:
       (A) LENGTH: 37 base pairs
       (B) TYPE: nucleic acid
       (C) STRANDEDNESS: single
       (D) TOPOLOGY: linear (xi) SEQUENCE DESCRIPTION: SEQ ID NO:35:

CACATCCCAG TTCCTCCAAC CGTGGCACCT CAGCATG                             37

(2) INFORMATION FOR SEQ ID NO:36:

(i) SEQUENCE CHARACTERISTICS:
       (A) LENGTH: 36 base pairs
       (B) TYPE: nucleic acid
       (C) STRANDEDNESS: single
       (D) TOPOLOGY: linear (xi) SEQUENCE DESCRIPTION: SEQ ID NO:36:

AGGAACTGGG ATGTGTACAA GGTCACATTC TTCCAG                              36

(2) INFORMATION FOR SEQ ID NO:37:

```
    (i) SEQUENCE CHARACTERISTICS:
         (A) LENGTH: 34 base pairs
         (B) TYPE: nucleic acid
         (C) STRANDEDNESS: single
         (D) TOPOLOGY: linear (xi) SEQUENCE DESCRIPTION: SEQ ID NO:37:

GTGGTTCTCA TACCAGAATT TCTGGGGATT TTCC                              34

(2) INFORMATION FOR SEQ ID NO:38:

(i) SEQUENCE CHARACTERISTICS:
         (A) LENGTH: 32 base pairs
         (B) TYPE: nucleic acid
         (C) STRANDEDNESS: single
         (D) TOPOLOGY: linear (xi) SEQUENCE DESCRIPTION: SEQ ID NO:38:

CTGGTATGAG AACCACACCT TCTCCATCCC AC                                32

(2) INFORMATION FOR SEQ ID NO:39:

(i) SEQUENCE CHARACTERISTICS:
         (A) LENGTH: 22 base pairs
         (B) TYPE: nucleic acid
         (C) STRANDEDNESS: single
         (D) TOPOLOGY: linear (xi) SEQUENCE DESCRIPTION: SEQ ID NO:39:

GAAGGACAAG GCTCTGGTCA AG                                           22

(2) INFORMATION FOR SEQ ID NO:40:

(i) SEQUENCE CHARACTERISTICS:
         (A) LENGTH: 22 base pairs
         (B) TYPE: nucleic acid
         (C) STRANDEDNESS: single
         (D) TOPOLOGY: linear (xi) SEQUENCE DESCRIPTION: SEQ ID NO:40:

CTTGACCAGA GCCTTGTCCT TC                                           22

(2) INFORMATION FOR SEQ ID NO:41:

(i) SEQUENCE CHARACTERISTICS:
         (A) LENGTH: 22 base pairs
         (B) TYPE: nucleic acid
         (C) STRANDEDNESS: single
         (D) TOPOLOGY: linear (xi) SEQUENCE DESCRIPTION: SEQ ID NO:41:

CTGGAAGGAC GCTCCTCTGG TC                                           22

(2) INFORMATION FOR SEQ ID NO:42:

(i) SEQUENCE CHARACTERISTICS:
         (A) LENGTH: 22 base pairs
         (B) TYPE: nucleic acid
         (C) STRANDEDNESS: single
         (D) TOPOLOGY: linear (xi) SEQUENCE DESCRIPTION: SEQ ID NO:42:

GACCAGAGGA GCGTCCTTCC AG                                           22

(2) INFORMATION FOR SEQ ID NO:43:

(i) SEQUENCE CHARACTERISTICS:
         (A) LENGTH: 22 base pairs
```

```
        (B) TYPE: nucleic acid
        (C) STRANDEDNESS: single
        (D) TOPOLOGY: linear (xi) SEQUENCE DESCRIPTION: SEQ ID NO:43:

GGACAAGCCT GCTGTCAAGG TC                                                    22

(2) INFORMATION FOR SEQ ID NO:44:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (xi) SEQUENCE DESCRIPTION: SEQ ID NO:44:

GACCTTGACA GCAGGCTTGT CC                                                    22

(2) INFORMATION FOR SEQ ID NO:45:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (xi) SEQUENCE DESCRIPTION: SEQ ID NO:45:

GACAAGCCTC TGGCTAAGGT CAC                                                   23

(2) INFORMATION FOR SEQ ID NO:46:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (xi) SEQUENCE DESCRIPTION: SEQ ID NO:46:

GTGACCTTAG CCAGAGGCTT GTC                                                   23

(2) INFORMATION FOR SEQ ID NO:47:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:47:

CCCAGAAAGC TTCCCGTTTG G                                                     21

(2) INFORMATION FOR SEQ ID NO:48:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:48:

CCAAACGGGA AGCTTTCTGG G                                                     21

(2) INFORMATION FOR SEQ ID NO:49:

(i) SEQUENCE CHARACTERISTICS:
        (A) LENGTH: 22 base pairs
        (B) TYPE: nucleic acid
        (C) STRANDEDNESS: single
```

(D) TOPOLOGY: linear (xi) SEQUENCE DESCRIPTION: SEQ ID NO:49:

CAGAAATTCG CTCGTTTGGA TC                                                  22

(2) INFORMATION FOR SEQ ID NO:50:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (xi) SEQUENCE DESCRIPTION: SEQ ID NO:50:

GATCCAAACG AGCGAATTTC TG                                                  22

(2) INFORMATION FOR SEQ ID NO:51:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (xi) SEQUENCE DESCRIPTION: SEQ ID NO:51:

GAAATTCTCC GCTTTGGATC CC                                                  22

(2) INFORMATION FOR SEQ ID NO:52:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (xi) SEQUENCE DESCRIPTION: SEQ ID NO:52:

GGGATCCAAA GCGGAGAATT TC                                                  22

(2) INFORMATION FOR SEQ ID NO:53:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (xi) SEQUENCE DESCRIPTION: SEQ ID NO:53:

ATTCTCCCGT GCTGATCCCA CC                                                  22

(2) INFORMATION FOR SEQ ID NO:54:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (xi) SEQUENCE DESCRIPTION: SEQ ID NO:54:

GGTGGGATCA GCACGGGAGA AT                                                  22

(2) INFORMATION FOR SEQ ID NO:55:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (xi) SEQUENCE DESCRIPTION: SEQ ID NO:55:

CTCCCGTTTG GCTCCCACCT TC                                           22

(2) INFORMATION FOR SEQ ID NO:56:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (xi) SEQUENCE DESCRIPTION: SEQ ID NO:56:

GAAGGTGGGA GCCAAACGGG AG                                           22

(2) INFORMATION FOR SEQ ID NO:57:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (xi) SEQUENCE DESCRIPTION: SEQ ID NO:57:

CCGTTTGGAT GCTACCTTCT CC                                           22

(2) INFORMATION FOR SEQ ID NO:58:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (xi) SEQUENCE DESCRIPTION: SEQ ID NO:58:

GGAGAAGGTA GCATCCAAAC GG                                           22

(2) INFORMATION FOR SEQ ID NO:59:

(i) SEQUENCE CHARACTERISTICS:
        (A) LENGTH: 14 amino acids
        (B) TYPE: amino acid
        (C) STRANDEDNESS: single
        (D) TOPOLOGY: linear (xi) SEQUENCE DESCRIPTION: SEQ ID NO:59:

Thr His Asp Leu Pro Lys Ala Val Val Lys Leu Glu Pro Pro
    1            5                  10

(2) INFORMATION FOR SEQ ID NO:60:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:60:

CUUGGACUGG UGCAGGGUUC UUCCCAGGGA UCCCUU                            36

(2) INFORMATION FOR SEQ ID NO:61:

(i) SEQUENCE CHARACTERISTICS:
        (A) LENGTH: 12 amino acids
        (B) TYPE: amino acid
        (C) STRANDEDNESS: single
        (D) TOPOLOGY: linear (xi) SEQUENCE DESCRIPTION: SEQ ID NO:61:

```
    Lys Gly Ser Leu Gly Arg Thr Leu His Gln Ser Lys
    1               5                   10
```

(2) INFORMATION FOR SEQ ID NO:62:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (xi) SEQUENCE DESCRIPTION: SEQ ID NO:62:

```
CUUUGGUUCC UCCAGGGUGA UGGUCAGUGG CUU                                 33
```

(2) INFORMATION FOR SEQ ID NO:63:

(i) SEQUENCE CHARACTERISTICS:
        (A) LENGTH: 11 amino acids
        (B) TYPE: amino acid
        (C) STRANDEDNESS: single
        (D) TOPOLOGY: linear (xi) SEQUENCE DESCRIPTION: SEQ ID NO:63:

```
    Lys Pro Val Thr Ile Thr Val Gln Gly Pro Lys
    1               5                   10
```

(2) INFORMATION FOR SEQ ID NO:64:

(i) SEQUENCE CHARACTERISTICS:
        (A) LENGTH: 47 base pairs
        (B) TYPE: nucleic acid
        (C) STRANDEDNESS: single
        (D) TOPOLOGY: linear (xi) SEQUENCE DESCRIPTION: SEQ ID NO:64:

```
CUUUGGGUAG CAGAAGGAGG AGGAGUAUCC UCCGUAUUCA CGGACUU                  47
```

(2) INFORMATION FOR SEQ ID NO:65:

(i) SEQUENCE CHARACTERISTICS:
        (A) LENGTH: 15 amino acids
        (B) TYPE: amino acid
        (C) STRANDEDNESS: single
        (D) TOPOLOGY: linear (xi) SEQUENCE DESCRIPTION: SEQ ID NO:65:

```
    Lys Ser Val Arg His His Tyr Ser Ser Xaa Phe Ser Ile Pro Lys
    1               5                   10                  15
```

(2) INFORMATION FOR SEQ ID NO:66:

(i) SEQUENCE CHARACTERISTICS:
        (A) LENGTH: 15 amino acids
        (B) TYPE: amino acid
        (C) STRANDEDNESS: single
        (D) TOPOLOGY: linear (xi) SEQUENCE DESCRIPTION: SEQ ID NO:66:

```
    Lys Ala Val Val Lys Leu Glu Pro Pro Trp Ile Gln Leu Val Lys
    1               5                   10                  15
```

(2) INFORMATION FOR SEQ ID NO:67:

(i) SEQUENCE CHARACTERISTICS:
        (A) LENGTH: 15 amino acids
        (B) TYPE: amino acid
        (C) STRANDEDNESS: single
        (D) TOPOLOGY: linear (xi) SEQUENCE DESCRIPTION: SEQ ID NO:67:

Glu Leu Ser Thr Thr Gly Gly Asn Ser Gly Ser Pro Val Lys Asn
1               5                   10                  15

(2) INFORMATION FOR SEQ ID NO:68:

(i) SEQUENCE CHARACTERISTICS:
　　　　(A) LENGTH: 14 amino acids
　　　　(B) TYPE: amino acid
　　　　(C) STRANDEDNESS: single
　　　　(D) TOPOLOGY: linear (xi) SEQUENCE DESCRIPTION: SEQ ID NO:68:

Glu Gln Thr Arg Leu Ser Asp Pro Val Asp Leu Gly Val Ile
1               5                   10

(2) INFORMATION FOR SEQ ID NO:69:

(i) SEQUENCE CHARACTERISTICS:
　　　　(A) LENGTH: 13 amino acids
　　　　(B) TYPE: amino acid
　　　　(C) STRANDEDNESS: single
　　　　(D) TOPOLOGY: linear (xi) SEQUENCE DESCRIPTION: SEQ ID NO:69:

Glu Asn Thr Ile Thr Tyr Ser Leu Leu Lys His Pro Glu
1               5                   10

(2) INFORMATION FOR SEQ ID NO:70:

(i) SEQUENCE CHARACTERISTICS:
　　　　(A) LENGTH: 15 amino acids
　　　　(B) TYPE: amino acid
　　　　(C) STRANDEDNESS: single
　　　　(D) TOPOLOGY: linear (xi) SEQUENCE DESCRIPTION: SEQ ID NO:70:

Glu Ala Glu Asn Thr Ile Thr Tyr Ser Leu Leu Lys His Pro Glu
1               5                   10                  15

(2) INFORMATION FOR SEQ ID NO:71:

(i) SEQUENCE CHARACTERISTICS:
　　　　(A) LENGTH: 18 amino acids
　　　　(B) TYPE: amino acid
　　　　(C) STRANDEDNESS: single
　　　　(D) TOPOLOGY: linear (xi) SEQUENCE DESCRIPTION: SEQ ID NO:71:

Thr His Asp Leu Pro Lys Ala Val Val Lys Leu Glu Pro Xaa Xaa Ile
1               5                   10                  15

Gln Val (2) INFORMATION FOR SEQ ID NO:72:

(i) SEQUENCE CHARACTERISTICS:
　　　　(A) LENGTH: 18 amino acids
　　　　(B) TYPE: amino acid
　　　　(C) STRANDEDNESS: single
　　　　(D) TOPOLOGY: linear (xi) SEQUENCE DESCRIPTION: SEQ ID NO:72:

Thr His Asp Leu Pro Lys Ala Val Val Lys Leu Glu Pro Pro Trp Ile
1               5                   10                  15

Gln Val (2) INFORMATION FOR SEQ ID NO:73:

(i) SEQUENCE CHARACTERISTICS:
        (A) LENGTH: 16 amino acids
        (B) TYPE: amino acid
        (C) STRANDEDNESS: single
        (D) TOPOLOGY: linear (ix) FEATURE:
        (A) NAME/KEY: Modified-site
        (B) LOCATION: 13
        (D) OTHER INFORMATION: /note= "The Xaa at position 13 is
            Gln or Thr."

(xi) SEQUENCE DESCRIPTION: SEQ ID NO:73:

Met Arg Asn Lys His Leu Asn Arg Ile Val Phe Leu Xaa Asn Tyr Lys
    1             5                 10              15

(2) INFORMATION FOR SEQ ID NO:74:

(i) SEQUENCE CHARACTERISTICS:
        (A) LENGTH: 48 base pairs
        (B) TYPE: nucleic acid
        (C) STRANDEDNESS: single
        (D) TOPOLOGY: linear (xi) SEQUENCE DESCRIPTION: SEQ ID NO:74:

ACGGGGGCTC GAGTTTGACC ACAGCCTTTG GAAGATCATG AGTCCCAG           48

(2) INFORMATION FOR SEQ ID NO:75:

(i) SEQUENCE CHARACTERISTICS:
        (A) LENGTH: 45 base pairs
        (B) TYPE: nucleic acid
        (C) STRANDEDNESS: single
        (D) TOPOLOGY: linear (xi) SEQUENCE DESCRIPTION: SEQ ID NO:75:

TTCGGGATGC TTGAGGAGTG AGTAGGTGAT CGTGTTCTCA GCCTC              45

(2) INFORMATION FOR SEQ ID NO:76:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (xi) SEQUENCE DESCRIPTION: SEQ ID NO:76:

GTGGTTGGCT TTGGGGATAG AGAAATTACT                           30

(2) INFORMATION FOR SEQ ID NO:77:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (xi) SEQUENCE DESCRIPTION: SEQ ID NO:77:

AGGGAGAAAG CAGTGTGGTA CCAGAC                               26

(2) INFORMATION FOR SEQ ID NO:78:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (xi) SEQUENCE DESCRIPTION: SEQ ID NO:78:

CTGTCTGTAC TCACCTACTT CCTCTGGAAG 30

(2) INFORMATION FOR SEQ ID NO:79:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (xi) SEQUENCE DESCRIPTION: SEQ ID NO:79:

AGGAGGATTG TCTGGAACCT GCTT 24

(2) INFORMATION FOR SEQ ID NO:80:

(i) SEQUENCE CHARACTERISTICS:
        (A) LENGTH: 1305 base pairs
        (B) TYPE: nucleic acid
        (C) STRANDEDNESS: single
        (D) TOPOLOGY: linear (ix) FEATURE:
        (A) NAME/KEY: CDS
        (B) LOCATION: 53..1042

(ix) FEATURE:
        (A) NAME/KEY: mat_peptide
        (B) LOCATION: 53..1042

(xi) SEQUENCE DESCRIPTION: SEQ ID NO:80:

```
CTGCAGACTC GCTCCAGAGC TGATGGGAAT CCTGCCGTTC CTACTGATCC CC ATG        55
                                                             Met
                                                               1

GAG AGC AAC TGG ACT GTC CAT GTG TTC TCA CGG ACT TTG TGC CAT ATG     103
Glu Ser Asn Trp Thr Val His Val Phe Ser Arg Thr Leu Cys His Met
        5                  10                  15

CTA CTG TGG ACA GCC GTG CTA AAT CTT GCT GCT GGG ACT CAT GAT CTT     151
Leu Leu Trp Thr Ala Val Leu Asn Leu Ala Ala Gly Thr His Asp Leu
         20                 25                  30

CCA AAG GCT GTG GTC AAA CTC GAG CCC CCG TGG ATC CAG GTG CTC AAG     199
Pro Lys Ala Val Val Lys Leu Glu Pro Pro Trp Ile Gln Val Leu Lys
     35                  40                  45

GAA GAC ACG GTG ACA CTG ACA TGC GAA GGG ACC CAC AAC CCT GGG AAC     247
Glu Asp Thr Val Thr Leu Thr Cys Glu Gly Thr His Asn Pro Gly Asn
 50                  55                  60                  65

TCT TCT ACC CAG TGG TTC CAC AAT GGG AGG TCC ATC CGG AGC CAG GTC     295
Ser Ser Thr Gln Trp Phe His Asn Gly Arg Ser Ile Arg Ser Gln Val
                 70                  75                  80

CAA GCC AGC TAC ACG TTT AAG GCC ACA GTC AAT GAC AGT GGA GAA TAT     343
Gln Ala Ser Tyr Thr Phe Lys Ala Thr Val Asn Asp Ser Gly Glu Tyr
             85                  90                  95

CGG TGT CAA ATG GAG CAG ACC CGC CTC AGC GAC CCT GTA GAT CTG GGA     391
Arg Cys Gln Met Glu Gln Thr Arg Leu Ser Asp Pro Val Asp Leu Gly
        100                 105                 110

GTG ATT TCT GAC TGG CTG CTG CTC CAG ACC CCT CAG CTG GTG TTT CTG     439
Val Ile Ser Asp Trp Leu Leu Leu Gln Thr Pro Gln Leu Val Phe Leu
    115                 120                 125

GAA GGG GAA ACC ATC ACG CTA AGG TGC CAT AGC TGG AGG AAC AAA CTA     487
Glu Gly Glu Thr Ile Thr Leu Arg Cys His Ser Trp Arg Asn Lys Leu
130                 135                 140                 145

CTG AAC AGG ATC TCG TTC TTC CAT AAT GAA AAA TCC GTG AGG TAT CAT     535
Leu Asn Arg Ile Ser Phe Phe His Asn Glu Lys Ser Val Arg Tyr His
                150                 155                 160
```

```
CAC TAC AGT AGT AAT TTC TCT ATC CCC AAA GCC AAC CAC AGT CAC AGT      583
His Tyr Ser Ser Asn Phe Ser Ile Pro Lys Ala Asn His Ser His Ser
            165                 170                 175

GGG GAC TAC TAC TGC AAA GGA AGT CTA GGA AGG ACA CTG CAC CAG TCC      631
Gly Asp Tyr Tyr Cys Lys Gly Ser Leu Gly Arg Thr Leu His Gln Ser
            180                 185                 190

AAG CCT GTC ACC ATC ACT GTC CAA GGG CCC AAG TCC AGC AGG TCT TTA      679
Lys Pro Val Thr Ile Thr Val Gln Gly Pro Lys Ser Ser Arg Ser Leu
195                 200                 205

CCA GTA TTG ACA ATT GTG GCT GCT GTC ACT GGG ATT GCT GTC GCA GCC      727
Pro Val Leu Thr Ile Val Ala Ala Val Thr Gly Ile Ala Val Ala Ala
210                 215                 220                 225

ATT GTT ATT ATC CTA GTA TCC TTG GTC TAT CTC AAG AAA AAG CAG GTT      775
Ile Val Ile Ile Leu Val Ser Leu Val Tyr Leu Lys Lys Lys Gln Val
            230                 235                 240

CCA GCT CTC CCA GGA AAC CCT GAT CAC AGG GAA ATG GGA GAA ACC CTT      823
Pro Ala Leu Pro Gly Asn Pro Asp His Arg Glu Met Gly Glu Thr Leu
            245                 250                 255

CCA GAG GAA GTA GGT GAG TAC AGA CAG CCC TCT GGG GGC TCA GTG CCT      871
Pro Glu Glu Val Gly Glu Tyr Arg Gln Pro Ser Gly Gly Ser Val Pro
            260                 265                 270

GTC AGC CCA GGG CCT CCA TCT GGA CTG GAG CCA ACA AGC AGC AGC CCA      919
Val Ser Pro Gly Pro Pro Ser Gly Leu Glu Pro Thr Ser Ser Ser Pro
275                 280                 285

TAC AAT CCT CCT GAT CTG GAA GAA GCT CCC AAA ACT GAG GCT GAG AAC      967
Tyr Asn Pro Pro Asp Leu Glu Glu Ala Pro Lys Thr Glu Ala Glu Asn
290                 295                 300                 305

ACG ATC ACC TAC TCA CTC CTC AAG CAT CCC GAA GCC TTG GAT GAA GAA     1015
Thr Ile Thr Tyr Ser Leu Leu Lys His Pro Glu Ala Leu Asp Glu Glu
            310                 315                 320

ACA GAG CAT GAT TAC CAA AAC CAC ATT TAGTCTCCCT TGGCATTGGG           1062
Thr Glu His Asp Tyr Gln Asn His Ile
            325                 330

AAAAGCAAGC CAGAAAGGCC AGGATCTAGT GTCTCCTGGT CCAAGGGATG CTGTAGATAT   1122

TAAAGAAAAC ATCCAGAGTC ACTTCTGTGA GTCCTGAAAC CAACAGACAC TACGAGATTG   1182

GTTCCCAATG GTTGACTGTA CTAATGACTC CCATAACTTA CAGCTTCCCA ACTCAAGACT   1242

CTTCTGCTAT CGATCCACAC TGCCACTAAA ATTAATCAAC TTACTGCCGT TAAGAGACTG   1302

CAG                                                                 1305

(2) INFORMATION FOR SEQ ID NO:81:

(i) SEQUENCE CHARACTERISTICS:
         (A) LENGTH: 330 amino acids
         (B) TYPE: amino acid
         (D) TOPOLOGY: linear (ii) MOLECULE TYPE: protein (xi) SEQUENCE DESCRIPTION: SEQ ID NO:81:

Met Glu Ser Asn Trp Thr Val His Val Phe Ser Arg Thr Leu Cys His
1               5                   10                  15

Met Leu Leu Trp Thr Ala Val Leu Asn Leu Ala Ala Gly Thr His Asp
            20                  25                  30

Leu Pro Lys Ala Val Val Lys Leu Glu Pro Pro Trp Ile Gln Val Leu
        35                  40                  45

Lys Glu Asp Thr Val Thr Leu Thr Cys Glu Gly Thr His Asn Pro Gly
    50                  55                  60

Asn Ser Ser Thr Gln Trp Phe His Asn Gly Arg Ser Ile Arg Ser Gln
```

```
                65                  70                  75                  80
Val Gln Ala Ser Tyr Thr Phe Lys Ala Thr Val Asn Asp Ser Gly Glu
                    85                  90                  95

Tyr Arg Cys Gln Met Glu Gln Thr Arg Leu Ser Asp Pro Val Asp Leu
            100                 105                 110

Gly Val Ile Ser Asp Trp Leu Leu Gln Thr Pro Gln Leu Val Phe
            115                 120                 125

Leu Glu Gly Glu Thr Ile Thr Leu Arg Cys His Ser Trp Arg Asn Lys
130                 135                 140

Leu Leu Asn Arg Ile Ser Phe Phe His Asn Glu Lys Ser Val Arg Tyr
145                 150                 155                 160

His His Tyr Ser Ser Asn Phe Ser Ile Pro Lys Ala Asn His Ser His
                165                 170                 175

Ser Gly Asp Tyr Tyr Cys Lys Gly Ser Leu Gly Arg Thr Leu His Gln
                180                 185                 190

Ser Lys Pro Val Thr Ile Thr Val Gln Gly Pro Lys Ser Ser Arg Ser
            195                 200                 205

Leu Pro Val Leu Thr Ile Val Ala Ala Val Thr Gly Ile Ala Val Ala
210                 215                 220

Ala Ile Val Ile Ile Leu Val Ser Leu Val Tyr Leu Lys Lys Lys Gln
225                 230                 235                 240

Val Pro Ala Leu Pro Gly Asn Pro Asp His Arg Glu Met Gly Glu Thr
                245                 250                 255

Leu Pro Glu Glu Val Gly Glu Tyr Arg Gln Pro Ser Gly Gly Ser Val
                260                 265                 270

Pro Val Ser Pro Gly Pro Pro Ser Gly Leu Glu Pro Thr Ser Ser Ser
            275                 280                 285

Pro Tyr Asn Pro Pro Asp Leu Glu Glu Ala Pro Lys Thr Glu Ala Glu
            290                 295                 300

Asn Thr Ile Thr Tyr Ser Leu Leu Lys His Pro Glu Ala Leu Asp Glu
305                 310                 315                 320

Glu Thr Glu His Asp Tyr Gln Asn His Ile
                325                 330

(2) INFORMATION FOR SEQ ID NO:82:

(i) SEQUENCE CHARACTERISTICS:
        (A) LENGTH: 924 base pairs
        (B) TYPE: nucleic acid
        (C) STRANDEDNESS: single
        (D) TOPOLOGY: linear (ix) FEATURE:
        (A) NAME/KEY: CDS
        (B) LOCATION: 2..922

(ix) FEATURE:
        (A) NAME/KEY: mat_peptide
        (B) LOCATION: 2..922

(xi) SEQUENCE DESCRIPTION: SEQ ID NO:82:

G AAT TCC GGT CCC AGA AAC CTG TGG CTG CTT CAA CCA TTG ACA GTT      46
  Asn Ser Gly Pro Arg Asn Leu Trp Leu Leu Gln Pro Leu Thr Val
   1               5                  10                  15

TTG CTG CTG CTG GCT TCT GCA GAC AGT CAA GCT GCA GCT CCC CCA AAG    94
Leu Leu Leu Leu Ala Ser Ala Asp Ser Gln Ala Ala Ala Pro Pro Lys
                 20                  25                  30

GCT GTG CTG AAA CTT GAG CCC CCG TGG ATC AAC GTG CTC CAG GAG GAC   142
Ala Val Leu Lys Leu Glu Pro Pro Trp Ile Asn Val Leu Gln Glu Asp
             35                  40                  45
```

```
TCT GTG ACT CTG ACA TGC CAG GGG GCT CGC AGC CCT GAG AGC GAC TCC      190
Ser Val Thr Leu Thr Cys Gln Gly Ala Arg Ser Pro Glu Ser Asp Ser
         50                      55                      60

ATT CAG TGG TTC CAC AAT GGG AAT CTC ATT CCC ACC CAC ACG CAG CCC      238
Ile Gln Trp Phe His Asn Gly Asn Leu Ile Pro Thr His Thr Gln Pro
     65                      70                      75

AGC TAC AGG TTC AAG GCC AAC AAC AAT GAC AGC GGG GAG TAC ACG TGC      286
Ser Tyr Arg Phe Lys Ala Asn Asn Asn Asp Ser Gly Glu Tyr Thr Cys
 80                      85                      90              95

CAG ACT GGC CAG ACC AGC CTC AGC GAC CCT GTG CAT CTG ACT GTG CTT      334
Gln Thr Gly Gln Thr Ser Leu Ser Asp Pro Val His Leu Thr Val Leu
                100                     105                     110

TCC GAA TGG CTG GTG CTC CAG ACC CCT CAC CTG GAG TTC CAG GAG GGA      382
Ser Glu Trp Leu Val Leu Gln Thr Pro His Leu Glu Phe Gln Glu Gly
            115                     120                     125

GAA ACC ATC ATG CTG AGG TGC CAC AGC TGG AAG GAC AAG CCT CTG GTC      430
Glu Thr Ile Met Leu Arg Cys His Ser Trp Lys Asp Lys Pro Leu Val
        130                     135                     140

AAG GTC ACA TTC TTC CAG AAT GGA AAA TCC CAG AAA TTC TCC CGT TTG      478
Lys Val Thr Phe Phe Gln Asn Gly Lys Ser Gln Lys Phe Ser Arg Leu
    145                     150                     155

GAT CCC ACC TTC TCC ATC CCA CAA GCA AAC CAC AGT CAC AGT GGT GAT      526
Asp Pro Thr Phe Ser Ile Pro Gln Ala Asn His Ser His Ser Gly Asp
160                     165                     170                 175

TAC CAC TGC ACA GGA AAC ATA GGC TAC ACG CTG TTC TCA TCC AAG CCT      574
Tyr His Cys Thr Gly Asn Ile Gly Tyr Thr Leu Phe Ser Ser Lys Pro
                180                     185                     190

GTG ACC ATC ACT GTC CAA GTG CCC AGC ATG GGC AGC TCT TCA CCA ATG      622
Val Thr Ile Thr Val Gln Val Pro Ser Met Gly Ser Ser Ser Pro Met
            195                     200                     205

GGG ATC ATT GTG GCT GTG GTC ATT GCG ACT GCT GTA GCA GCC ATT GTT      670
Gly Ile Ile Val Ala Val Val Ile Ala Thr Ala Val Ala Ala Ile Val
        210                     215                     220

GCT GCT GTA GTG GCC TTG ATC TAC TGC AGG AAA AAG CGG ATT TCA GCC      718
Ala Ala Val Val Ala Leu Ile Tyr Cys Arg Lys Lys Arg Ile Ser Ala
    225                     230                     235

AAT TCC ACT GAT CCT GTG AAG GCT GCC CAA TTT GAG CCA CCT GGA CGT      766
Asn Ser Thr Asp Pro Val Lys Ala Ala Gln Phe Glu Pro Pro Gly Arg
240                     245                     250                 255

CAA ATG ATT GCC ATC AGA AAG AGA CAA CTT GAA GAA ACC AAC AAT GAC      814
Gln Met Ile Ala Ile Arg Lys Arg Gln Leu Glu Glu Thr Asn Asn Asp
                260                     265                     270

TAT GAA ACA GCT GAC GGC GGC TAC ATG ACT CTG AAC CCC AGG GCA CCT      862
Tyr Glu Thr Ala Asp Gly Gly Tyr Met Thr Leu Asn Pro Arg Ala Pro
            275                     280                     285

ACT GAC GAT AAA AAC ATC TAC CTG ACT CTT CCT CCC AAC GAC CAT GTC      910
Thr Asp Asp Lys Asn Ile Tyr Leu Thr Leu Pro Pro Asn Asp His Val
        290                     295                     300

AAC AGT AAT AAC TA                                                   924
Asn Ser Asn Asn
    305
```

(2) INFORMATION FOR SEQ ID NO:83:

(i) SEQUENCE CHARACTERISTICS:
        (A) LENGTH: 307 amino acids
        (B) TYPE: amino acid
        (D) TOPOLOGY: linear (ii) MOLECULE TYPE: protein (xi) SEQUENCE DESCRIPTION: SEQ ID NO:83:

```
Asn Ser Gly Pro Arg Asn Leu Trp Leu Leu Gln Pro Leu Thr Val Leu
 1               5                  10                  15

Leu Leu Leu Ala Ser Ala Asp Ser Gln Ala Ala Pro Pro Lys Ala
            20                  25                  30

Val Leu Lys Leu Glu Pro Pro Trp Ile Asn Val Leu Gln Glu Asp Ser
            35                  40                  45

Val Thr Leu Thr Cys Gln Gly Ala Arg Ser Pro Glu Ser Asp Ser Ile
 50                  55                  60

Gln Trp Phe His Asn Gly Asn Leu Ile Pro Thr His Thr Gln Pro Ser
 65                  70                  75                  80

Tyr Arg Phe Lys Ala Asn Asn Asn Asp Ser Gly Glu Tyr Thr Cys Gln
                85                  90                  95

Thr Gly Gln Thr Ser Leu Ser Asp Pro Val His Leu Thr Val Leu Ser
            100                 105                 110

Glu Trp Leu Val Leu Gln Thr Pro His Leu Glu Phe Gln Glu Gly Glu
            115                 120                 125

Thr Ile Met Leu Arg Cys His Ser Trp Lys Asp Lys Pro Leu Val Lys
 130                 135                 140

Val Thr Phe Phe Gln Asn Gly Lys Ser Gln Lys Phe Ser Arg Leu Asp
145                 150                 155                 160

Pro Thr Phe Ser Ile Pro Gln Ala Asn His Ser His Ser Gly Asp Tyr
                165                 170                 175

His Cys Thr Gly Asn Ile Gly Tyr Thr Leu Phe Ser Ser Lys Pro Val
            180                 185                 190

Thr Ile Thr Val Gln Val Pro Ser Met Gly Ser Ser Ser Pro Met Gly
            195                 200                 205

Ile Ile Val Ala Val Val Ile Ala Thr Ala Val Ala Ala Ile Val Ala
 210                 215                 220

Ala Val Val Ala Leu Ile Tyr Cys Arg Lys Lys Arg Ile Ser Ala Asn
225                 230                 235                 240

Ser Thr Asp Pro Val Lys Ala Ala Gln Phe Glu Pro Pro Gly Arg Gln
                245                 250                 255

Met Ile Ala Ile Arg Lys Arg Gln Leu Glu Glu Thr Asn Asn Asp Tyr
            260                 265                 270

Glu Thr Ala Asp Gly Gly Tyr Met Thr Leu Asn Pro Arg Ala Pro Thr
            275                 280                 285

Asp Asp Lys Asn Ile Tyr Leu Thr Leu Pro Pro Asn Asp His Val Asn
            290                 295                 300

Ser Asn Asn
305

(2) INFORMATION FOR SEQ ID NO:84:

(i) SEQUENCE CHARACTERISTICS:
        (A) LENGTH: 80 amino acids
        (B) TYPE: amino acid
        (C) STRANDEDNESS: single
        (D) TOPOLOGY: linear (xi) SEQUENCE DESCRIPTION: SEQ ID NO:84:

Phe Gly Leu Thr Ala Asn Ser Asp Thr His Leu Leu Gln Gly Gln Ser
         1               5                  10                  15

Leu Thr Leu Thr Leu Glu Ser Pro Pro Gly Ser Ser Pro Ser Val Gln
                      20                  25                  30

Cys Arg Ser Pro Arg Gly Lys Asn Ile Gln Gly Gly Lys Thr Leu Ser
                       35                  40                  45
```

Val Ser Gln Leu Glu Leu Gln Asp Ser Gly Thr Trp Thr Cys Thr Val
    50                  55                  60

Leu Gln Asn Gln Lys Lys Val Gln Phe Lys Ile Asp Ile Val Val Leu
65                  70                  75                  80

(2) INFORMATION FOR SEQ ID NO:85:

(i) SEQUENCE CHARACTERISTICS:
        (A) LENGTH: 81 amino acids
        (B) TYPE: amino acid
        (C) STRANDEDNESS: single
        (D) TOPOLOGY: linear (xi) SEQUENCE DESCRIPTION: SEQ ID NO:85:

Phe Lys Val Thr Phe Ser Pro Gly Thr Ser Leu Leu Gln Gly Gln Ser
1               5                   10                  15

Leu Thr Leu Thr Leu Asp Ser Asn Ser Lys Val Ser Asn Pro Leu Thr
                20                  25                  30

Glu Cys Lys His Lys Lys Gly Lys Val Val Ser Gly Ser Lys Val Leu
            35                  40                  45

Ser Met Ser Asn Leu Arg Val Gln Asp Ser Asp Phe Trp Asn Cys Thr
        50                  55                  60

Val Thr Leu Asp Gln Lys Lys Asn Trp Phe Gly Met Thr Leu Ser Val
65                  70                  75                  80

Leu (2) INFORMATION FOR SEQ ID NO:86:

(i) SEQUENCE CHARACTERISTICS:
        (A) LENGTH: 81 amino acids
        (B) TYPE: amino acid
        (C) STRANDEDNESS: single
        (D) TOPOLOGY: linear (xi) SEQUENCE DESCRIPTION: SEQ ID NO:86:

Phe Arg Val Thr Phe Asn Pro Gly Thr Arg Leu Leu Gln Gly Gln Ser
1               5                   10                  15

Leu Thr Leu Ile Leu Asp Ser Asn Pro Lys Val Ser Asp Pro Pro Ile
                20                  25                  30

Glu Cys Lys His Lys Ser Ser Asn Ile Val Lys Asp Ser Lys Ala Phe
            35                  40                  45

Ser Thr His Ser Leu Arg Ile Gln Asp Ser Gly Ile Trp Asn Cys Thr
        50                  55                  60

Val Thr Leu Asn Gln Lys Lys His Ser Phe Asp Met Lys Leu Ser Val
65                  70                  75                  80

Leu (2) INFORMATION FOR SEQ ID NO:87:

(i) SEQUENCE CHARACTERISTICS:
        (A) LENGTH: 83 amino acids
        (B) TYPE: amino acid
        (C) STRANDEDNESS: single
        (D) TOPOLOGY: linear (xi) SEQUENCE DESCRIPTION: SEQ ID NO:87:

Thr Gly Lys Leu His Gln Glu Val Asn Leu Val Val Met Arg Ala Thr
1               5                   10                  15

Gln Leu Gln Lys Asn Leu Thr Cys Glu Val Asn Glu Pro Thr Ser Pro
                20                  25                  30

```
            Lys Leu Met Leu Ser Leu Lys Leu Glu Asn Lys Glu Ala Leu Val Ser
                         35                  40                  45

Lys Arg Glu Lys Ala Val Trp Val Leu Asn Pro Glu Ala Gly Met Trp
             50                  55                  60

Gln Cys Leu Leu Ser Asp Ser Gly Gln Val Leu Glu Ser Asn Ile
             65                  70                  75                  80

Lys Val Leu (2) INFORMATION FOR SEQ ID NO:88:

(i) SEQUENCE CHARACTERISTICS:
         (A) LENGTH: 87 amino acids
         (B) TYPE: amino acid
         (C) STRANDEDNESS: single
         (D) TOPOLOGY: linear (xi) SEQUENCE DESCRIPTION: SEQ ID NO:88:

Pro Gln Lys Pro Lys Val Ser Leu Asn Pro Pro Trp Asn Arg Ile Phe
             1               5                  10                  15

Lys Gly Glu Asn Val Thr Leu Thr Cys Asn Gly Asn Asn Glu Glu Glu
                         20                  25                  30

Val Ser Ser Thr Lys Trp Phe His Asn Gly Ser Leu Ser Glu Glu Thr
                         35                  40                  45

Asn Ser Ser Leu Asn Ile Val Asn Ala Lys Phe Glu Asp Ser Gly Glu
                 50                  55                  60

Tyr Lys Cys Gln His Gln Gln Val Asn Glu Ser Glu Pro Val Tyr Leu
             65                  70                  75                  80

Glu Val Phe Ser Asp Trp Leu
                              85

(2) INFORMATION FOR SEQ ID NO:89:

(i) SEQUENCE CHARACTERISTICS:
         (A) LENGTH: 84 amino acids
         (B) TYPE: amino acid
         (C) STRANDEDNESS: single
         (D) TOPOLOGY: linear (xi) SEQUENCE DESCRIPTION: SEQ ID NO:89:

Trp Leu Leu Leu Gln Ala Ser Ala Glu Val Val Met Glu Gly Gln Pro
             1               5                  10                  15

Leu Phe Leu Arg Cys His Gly Trp Arg Asn Asn Asp Val Tyr Lys Val
                         20                  25                  30

Ile Tyr Tyr Lys Asp Gly Glu Ala Leu Lys Tyr Trp Tyr Glu Asn His
                         35                  40                  45

Asn Ile Ser Ile Thr Asn Ala Thr Val Glu Asp Ser Gly Thr Tyr Tyr
                 50                  55                  60

Cys Thr Gly Lys Val Trp Gln Leu Asp Tyr Glu Ser Glu Pro Leu Asn
             65                  70                  75                  80

Ile Thr Val Ile (2) INFORMATION FOR SEQ ID NO:90:

(i) SEQUENCE CHARACTERISTICS:
         (A) LENGTH: 87 amino acids
         (B) TYPE: amino acid
         (C) STRANDEDNESS: single
         (D) TOPOLOGY: linear (xi) SEQUENCE DESCRIPTION: SEQ ID NO:90:

Pro Pro Lys Ala Val Leu Lys Leu Glu Pro Pro Trp Ile Asn Val Leu
```

```
              1           5                   10                  15
         Gln Glu Asp Ser Val Thr Leu Thr Cys Gln Gly Ala Arg Ser Pro Glu
                         20                  25                  30

Ser Asp Ser Ile Gln Trp Phe His Asn Gly Asn Leu Ile Pro Thr His
                         35                  40                  45

Thr Gln Pro Ser Tyr Arg Phe Lys Ala Asn Asn Asn Asp Ser Gly Glu
                         50                  55                  60

Tyr Thr Cys Gln Thr Gly Gln Thr Ser Leu Ser Asp Pro Phe His Leu
         65                  70                  75                  80

Thr Val Leu Ser Glu Trp Leu
                         85
```

(2) INFORMATION FOR SEQ ID NO:91:

(i) SEQUENCE CHARACTERISTICS:
        (A) LENGTH: 83 amino acids
        (B) TYPE: amino acid
        (C) STRANDEDNESS: single
        (D) TOPOLOGY: linear (xi) SEQUENCE DESCRIPTION: SEQ ID NO:91:

```
         Trp Leu Val Leu Gln Thr Pro Trp Leu Glu Phe Gln Glu Gly Glu Thr
         1               5                   10                  15

Ile Met Leu Arg Cys His Ser Trp Lys Asp Lys Pro Leu Val Lys Val
                         20                  25                  30

Thr Phe Phe Gln Asn Gly Lys Ser Gln Lys Phe Ser Arg Leu Asp Pro
                         35                  40                  45

Thr Phe Ser Ile Pro Gln Ala His Ser His Ser Gly Asp Tyr His Cys
                         50                  55                  60

Thr Gly Asn Ile Gly Tyr Thr Leu Phe Ser Ser Lys Pro Val Thr Ile
         65                  70                  75                  80

Thr Val Gln
```

(2) INFORMATION FOR SEQ ID NO:92:

(i) SEQUENCE CHARACTERISTICS:
        (A) LENGTH: 87 amino acids
        (B) TYPE: amino acid
        (C) STRANDEDNESS: single
        (D) TOPOLOGY: linear (xi) SEQUENCE DESCRIPTION: SEQ ID NO:92:

```
         Ala Thr Lys Ala Val Ile Thr Leu Gln Pro Pro Trp Val Ser Ile Phe
         1               5                   10                  15

Gln Lys Glu Asn Val Thr Leu Trp Cys Glu Gly Pro His Leu Pro Gly
                         20                  25                  30

Asp Ser Ser Thr Gln Trp Phe Ile Asn Gly Thr Ala Val Gln Ile Ser
                         35                  40                  45

Thr Pro Ser Tyr Ser Ile Pro Glu Ala Ser Phe Gln Asp Ser Gly Glu
                         50                  55                  60

Tyr Arg Cys Gln Ile Gly Ser Ser Met Pro Ser Asp Pro Val Gln Leu
         65                  70                  75                  80

Gln Ile His Asn Asp Trp Leu
                         85
```

(2) INFORMATION FOR SEQ ID NO:93:

(i) SEQUENCE CHARACTERISTICS:
        (A) LENGTH: 81 amino acids
        (B) TYPE: amino acid (C) STRANDEDNESS: single
        (D) TOPOLOGY: linear (xi) SEQUENCE DESCRIPTION: SEQ ID NO:93:

Leu Leu Gln Ala Ser Arg Arg Val Leu Thr Glu Glu Pro Leu Ala Leu
    1               5                   10                  15

Arg Cys His Gly Trp Lys Asn Lys Leu Val Tyr Asn Val Val Phe Tyr
                20                  25                  30

Arg Asn Gly Lys Ser Phe Gln Phe Ser Ser Asp Ser Glu Val Ala Ile
                35                  40                  45

Leu Lys Thr Asn Leu Ser His Ser Gly Ile Tyr His Cys Ser Gly Thr
        50                  55                  60

Gly Arg His Arg Tyr Thr Ser Ala Gly Val Ser Ile Thr Val Lys Glu
    65                  70                  75                  80

Leu (2) INFORMATION FOR SEQ ID NO:94:

(i) SEQUENCE CHARACTERISTICS:
        (A) LENGTH: 91 amino acids
        (B) TYPE: amino acid
        (C) STRANDEDNESS: single
        (D) TOPOLOGY: linear (xi) SEQUENCE DESCRIPTION: SEQ ID NO:94:

Phe Thr Thr Pro Val Leu Arg Ala Ser Val Ser Ser Pro Phe Pro Glu
    1               5                   10                  15

Gly Ser Leu Val Thr Leu Asn Cys Glu Thr Asn Leu Leu Leu Gln Arg
                20                  25                  30

Pro Gly Leu Gln Leu His Phe Ser Phe Tyr Val Gly Ser Lys Ile Leu
                35                  40                  45

Glu Tyr Arg Asn Thr Ser Ser Glu Tyr His Ile Ala Arg Ala Glu Arg
        50                  55                  60

Glu Asp Ala Gly Phe Tyr Trp Cys Glu Val Ala Thr Glu Asp Ser Ser
    65                  70                  75                  80

Val Leu Lys Arg Ser Pro Glu Leu Glu Leu Gln
                85                  90

(2) INFORMATION FOR SEQ ID NO:95:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (xi) SEQUENCE DESCRIPTION: SEQ ID NO:95:

CTGTACGGGC GCAGTGTGGC AGC                                         23

(2) INFORMATION FOR SEQ ID NO:96:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (xi) SEQUENCE DESCRIPTION: SEQ ID NO:96:

GCTGCCACAC TGCGCCCGTA CAG                                         23

(2) INFORMATION FOR SEQ ID NO:97:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (xi) SEQUENCE DESCRIPTION: SEQ ID NO:97:

GTACCGGCAA AGCATGGCAG CTGG                24

(2) INFORMATION FOR SEQ ID NO:98:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (xi) SEQUENCE DESCRIPTION: SEQ ID NO:98:

CCAGCTGCCA TGCTTTGCCC GTAC                24

(2) INFORMATION FOR SEQ ID NO:99:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (xi) SEQUENCE DESCRIPTION: SEQ ID NO:99:

GGGCAAAGTG GCACAGCTGG AC                  22

(2) INFORMATION FOR SEQ ID NO:100:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (xi) SEQUENCE DESCRIPTION: SEQ ID NO:100:

GTCCAGCTGT GCCACTTTGC CC                  22

(2) INFORMATION FOR SEQ ID NO:101:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (xi) SEQUENCE DESCRIPTION: SEQ ID NO:101:

GCAAAGTGTG GGCACTGGAC TATG                24

(2) INFORMATION FOR SEQ ID NO:102:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (xi) SEQUENCE DESCRIPTION: SEQ ID NO:102:

CATAGTCCAG TGCCCACACT TTGC                24

(2) INFORMATION FOR SEQ ID NO:103:

(i) SEQUENCE CHARACTERISTICS:
        (A) LENGTH: 23 base pairs (B) TYPE: nucleic acid
            (C) STRANDEDNESS: single
            (D) TOPOLOGY: linear (xi) SEQUENCE DESCRIPTION: SEQ ID NO:103:

GTGTGGCAGG CAGACTATGA GTC                                          23

(2) INFORMATION FOR SEQ ID NO:104:

(i) SEQUENCE CHARACTERISTICS:
            (A) LENGTH: 23 base pairs
            (B) TYPE: nucleic acid
            (C) STRANDEDNESS: single
            (D) TOPOLOGY: linear (xi) SEQUENCE DESCRIPTION: SEQ ID NO:104:

GACTCATAGT CTGCCTGCCA CAC                                          23

(2) INFORMATION FOR SEQ ID NO:105:

(i) SEQUENCE CHARACTERISTICS:
            (A) LENGTH: 23 base pairs
            (B) TYPE: nucleic acid
            (C) STRANDEDNESS: single
            (D) TOPOLOGY: linear (xi) SEQUENCE DESCRIPTION: SEQ ID NO:105:

GTGGCAGCTG GCATATGAGT CTG                                          23

(2) INFORMATION FOR SEQ ID NO:106:

(i) SEQUENCE CHARACTERISTICS:
            (A) LENGTH: 23 base pairs
            (B) TYPE: nucleic acid
            (C) STRANDEDNESS: single
            (D) TOPOLOGY: linear (xi) SEQUENCE DESCRIPTION: SEQ ID NO:106:

CAGACTCATA TGCCAGCTGC CAC                                          23

(2) INFORMATION FOR SEQ ID NO:107:

(i) SEQUENCE CHARACTERISTICS:
            (A) LENGTH: 23 base pairs
            (B) TYPE: nucleic acid
            (C) STRANDEDNESS: single
            (D) TOPOLOGY: linear (xi) SEQUENCE DESCRIPTION: SEQ ID NO:107:

GCAGCTGGAC GCAGAGTCTG AGC                                          23

(2) INFORMATION FOR SEQ ID NO:108:

(i) SEQUENCE CHARACTERISTICS:
            (A) LENGTH: 23 base pairs
            (B) TYPE: nucleic acid
            (C) STRANDEDNESS: single
            (D) TOPOLOGY: linear (xi) SEQUENCE DESCRIPTION: SEQ ID NO:108:

GCTCAGACTC TGCGTCCAGC TGC                                          23

(2) INFORMATION FOR SEQ ID NO:109:

(i) SEQUENCE CHARACTERISTICS:
            (A) LENGTH: 23 base pairs
            (B) TYPE: nucleic acid
            (C) STRANDEDNESS: single -continued (D) TOPOLOGY: linear (xi) SEQUENCE DESCRIPTION: SEQ ID NO:109:

GCTGGACTAT GCATCTGAGC CCC                                                    23

(2) INFORMATION FOR SEQ ID NO:110:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (xi) SEQUENCE DESCRIPTION: SEQ ID NO:110:

GGGGCTCAGA TGCATAGTCC AGC                                                    23

(2) INFORMATION FOR SEQ ID NO:111:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (xi) SEQUENCE DESCRIPTION: SEQ ID NO:111:

GCTCTCAAGG CATGGTATGA GAAC                                                   24

(2) INFORMATION FOR SEQ ID NO:112:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (xi) SEQUENCE DESCRIPTION: SEQ ID NO:112:

GTTCTCATAC CATGCCTTGA GAGC                                                   24

(2) INFORMATION FOR SEQ ID NO:113:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (xi) SEQUENCE DESCRIPTION: SEQ ID NO:113:

CTCAAGTACG CATATGAGAA CCAC                                                   24

(2) INFORMATION FOR SEQ ID NO:114:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (xi) SEQUENCE DESCRIPTION: SEQ ID NO:114:

GTGGTTCTCA TATGCGTACT TGAG                                                   24

(2) INFORMATION FOR SEQ ID NO:115:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (xi) SEQUENCE DESCRIPTION: SEQ ID NO:115:

CAAGTACTGG GCAGAGAACC AC                                                22

(2) INFORMATION FOR SEQ ID NO:116:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (xi) SEQUENCE DESCRIPTION: SEQ ID NO:116:

GTGGTTCTCT GCCCAGTACT TG                                                22

(2) INFORMATION FOR SEQ ID NO:117:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (xi) SEQUENCE DESCRIPTION: SEQ ID NO:117:

GTACTGGTAT GCAAACCACA ACATC                                             25

(2) INFORMATION FOR SEQ ID NO:118:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (xi) SEQUENCE DESCRIPTION: SEQ ID NO:118:

GATGTTGTGG TTTGCATACC AGTAC                                             25

(2) INFORMATION FOR SEQ ID NO:119:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (xi) SEQUENCE DESCRIPTION: SEQ ID NO:119:

CTGGTATGAG GCACACAACA TCTCC                                             25

(2) INFORMATION FOR SEQ ID NO:120:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (xi) SEQUENCE DESCRIPTION: SEQ ID NO:120:

GGAGATGTTG TGTGCCTCAT ACCAG                                             25

(2) INFORMATION FOR SEQ ID NO:121:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (xi) SEQUENCE DESCRIPTION: SEQ ID NO:121:

```
GGTATGAGAA CGCAAACATC TCCATTAC                                                   28

(2) INFORMATION FOR SEQ ID NO:122:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (xi) SEQUENCE DESCRIPTION: SEQ ID NO:122:

GTAATGGAGA TGTTTGCGTT CTCATACC                                                   28

(2) INFORMATION FOR SEQ ID NO:123:

(i) SEQUENCE CHARACTERISTICS:
        (A) LENGTH: 105 base pairs
        (B) TYPE: nucleic acid
        (C) STRANDEDNESS: single
        (D) TOPOLOGY: linear (ix) FEATURE:
        (A) NAME/KEY: CDS
        (B) LOCATION: 1..105

(ix) FEATURE:
        (A) NAME/KEY: mat_peptide
        (B) LOCATION: 1..105

(xi) SEQUENCE DESCRIPTION: SEQ ID NO:123:
```

TCC AAG CCT GTG ACC ATC ACT GTC CAA GTG CCC AGC ATG GGC AGC TCT                  48
Ser Lys Pro Val Thr Ile Thr Val Gln Val Pro Ser Met Gly Ser Ser
 1               5                  10                  15

TCA CCA NTG GGG ATC ATT GTG GCT GTG GTC ATT GCG ACT GCT GTA GCA                  96
Ser Pro Xaa Gly Ile Ile Val Ala Val Val Ile Ala Thr Ala Val Ala
                20                  25                  30

GCC ATT GTT                                                                     105
Ala Ile Val
        35

```
(2) INFORMATION FOR SEQ ID NO:124:

(i) SEQUENCE CHARACTERISTICS:
        (A) LENGTH: 35 amino acids
        (B) TYPE: amino acid
        (D) TOPOLOGY: linear (ii) MOLECULE TYPE: protein (xi) SEQUENCE DESCRIPTION: SEQ ID NO:124:
```

Ser Lys Pro Val Thr Ile Thr Val Gln Val Pro Ser Met Gly Ser Ser
 1               5                  10                  15

Ser Pro Xaa Gly Ile Ile Val Ala Val Val Ile Ala Thr Ala Val Ala
                20                  25                  30

Ala Ile Val
        35

```
(2) INFORMATION FOR SEQ ID NO:125:

(i) SEQUENCE CHARACTERISTICS:
        (A) LENGTH: 105 base pairs
        (B) TYPE: nucleic acid
        (C) STRANDEDNESS: single
        (D) TOPOLOGY: linear (ix) FEATURE:
        (A) NAME/KEY: CDS
        (B) LOCATION: 1..105
```

(ix) FEATURE:
    (A) NAME/KEY: mat_peptide
    (B) LOCATION: 1..105

(xi) SEQUENCE DESCRIPTION: SEQ ID NO:125:

```
TCC AAG CCT GTC ACC ATC ACT GTC CAA GGG CCC AAG TCC AGC AGG TCT      48
Ser Lys Pro Val Thr Ile Thr Val Gln Gly Pro Lys Ser Ser Arg Ser
 1               5                  10                  15

TTA CCA GTA TTG ACA ATT GTG GCT GCT GTC ACT GGG ATT GCT GTC GCA      96
Leu Pro Val Leu Thr Ile Val Ala Ala Val Thr Gly Ile Ala Val Ala
                20                  25                  30

GCC ATT GTT                                                         105
Ala Ile Val
        35
```

(2) INFORMATION FOR SEQ ID NO:126:

(i) SEQUENCE CHARACTERISTICS:
        (A) LENGTH: 35 amino acids
        (B) TYPE: amino acid
        (D) TOPOLOGY: linear (ii) MOLECULE TYPE: protein (xi) SEQUENCE DESCRIPTION: SEQ ID NO:126:

```
Ser Lys Pro Val Thr Ile Thr Val Gln Gly Pro Lys Ser Ser Arg Ser
 1               5                  10                  15

Leu Pro Val Leu Thr Ile Val Ala Ala Val Thr Gly Ile Ala Val Ala
                20                  25                  30

Ala Ile Val
        35
```

(2) INFORMATION FOR SEQ ID NO:127:

(i) SEQUENCE CHARACTERISTICS:
        (A) LENGTH: 57 base pairs
        (B) TYPE: nucleic acid
        (C) STRANDEDNESS: single
        (D) TOPOLOGY: linear (ix) FEATURE:
        (A) NAME/KEY: CDS
        (B) LOCATION: 1..57

(ix) FEATURE:
        (A) NAME/KEY: mat_peptide
        (B) LOCATION: 1..57

(xi) SEQUENCE DESCRIPTION: SEQ ID NO:127:

```
GCT GAG AAC ACG ATC ACC TAC TCA CTC CTC AAG CAT CCC GAA GCC TTG      48
Ala Glu Asn Thr Ile Thr Tyr Ser Leu Leu Lys His Pro Glu Ala Leu
 1               5                  10                  15

GAT GAA GAA                                                          57
Asp Glu Glu
```

(2) INFORMATION FOR SEQ ID NO:128:

(i) SEQUENCE CHARACTERISTICS:
        (A) LENGTH: 19 amino acids
        (B) TYPE: amino acid
        (D) TOPOLOGY: linear (ii) MOLECULE TYPE: protein (xi) SEQUENCE DESCRIPTION: SEQ ID NO:128:

```
Ala Glu Asn Thr Ile Thr Tyr Ser Leu Leu Lys His Pro Glu Ala Leu
 1               5                  10                  15
```

Asp Glu Glu (2) INFORMATION FOR SEQ ID NO:129:

(i) SEQUENCE CHARACTERISTICS:
        (A) LENGTH: 57 base pairs
        (B) TYPE: nucleic acid
        (C) STRANDEDNESS: single
        (D) TOPOLOGY: linear (ix) FEATURE:
        (A) NAME/KEY: CDS
        (B) LOCATION: 1..57

(ix) FEATURE:
        (A) NAME/KEY: mat_peptide
        (B) LOCATION: 1..57

(xi) SEQUENCE DESCRIPTION: SEQ ID NO:129:

```
GCT GAG AAC AAA ATC ACC TAT TCA CNG CTT ATG CNN TCG GAA GCN TCC        48
Ala Glu Asn Lys Ile Thr Tyr Ser Xaa Leu Met Xaa Ser Glu Xaa Ser
 1               5                  10                  15

NAN GAA GAA                                                            57
Xaa Glu Glu
```

(2) INFORMATION FOR SEQ ID NO:130:

(i) SEQUENCE CHARACTERISTICS:
        (A) LENGTH: 19 amino acids
        (B) TYPE: amino acid
        (D) TOPOLOGY: linear (ii) MOLECULE TYPE: protein (xi) SEQUENCE DESCRIPTION: SEQ ID NO:130:

```
Ala Glu Asn Lys Ile Thr Tyr Ser Xaa Leu Met Xaa Ser Glu Xaa Ser
 1               5                  10                  15

Xaa Glu Glu
```

(2) INFORMATION FOR SEQ ID NO:131:

(i) SEQUENCE CHARACTERISTICS:
        (A) LENGTH: 1042 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: join(2..454, 458..1039)

(ix) FEATURE:
        (A) NAME/KEY: terminator
        (B) LOCATION: 455..457
        (D) OTHER INFORMATION: /standard_name= "internal stop
            codon"

(xi) SEQUENCE DESCRIPTION: SEQ ID NO:131:

```
G AAT TCC GGT CCC AGA AAC CTG TGG CTG CTT CAA CCA TTG ACA GTT          46
  Asn Ser Gly Pro Arg Asn Leu Trp Leu Leu Gln Pro Leu Thr Val
   1               5                  10                  15

TTG CTG CTG CTG GCT TCT GCA GAC AGT CAA GCT GCA GCT CCC CCA AAG        94
Leu Leu Leu Leu Ala Ser Ala Asp Ser Gln Ala Ala Ala Pro Pro Lys
                 20                  25                  30

GCT GTG CTG AAA CTT GAG CCC CCG TGG ATC AAC GTG CTC CAG GAG GAC       142
Ala Val Leu Lys Leu Glu Pro Pro Trp Ile Asn Val Leu Gln Glu Asp
             35                  40                  45
```

```
TCT GTG ACT CTG ACA TGC CAG GGG GCT CGC AGC CCT GAG AGC GAC TCC         190
Ser Val Thr Leu Thr Cys Gln Gly Ala Arg Ser Pro Glu Ser Asp Ser
        50                  55                  60

ATT CAG TGG TTC CAC AAT GGG AAT CTC ATT CCC ACC CAC ACG CAG CCC         238
Ile Gln Trp Phe His Asn Gly Asn Leu Ile Pro Thr His Thr Gln Pro
65                  70                  75

AGC TAC AGG TTC AAG GCC AAC AAC AAT GAC AGC GGG GAG TAC ACG TGC         286
Ser Tyr Arg Phe Lys Ala Asn Asn Asn Asp Ser Gly Glu Tyr Thr Cys
80                  85                  90                  95

CAG ACT GGC CAG ACC AGC CTC AGC GAC CCT GTG CAT CTG ACT GTG CTT         334
Gln Thr Gly Gln Thr Ser Leu Ser Asp Pro Val His Leu Thr Val Leu
                100                 105                 110

TCC GGT CAG TGG AGG AAG GCC CCA GGG TGG ACC TGG GAG GGG CCA GGA         382
Ser Gly Gln Trp Arg Lys Ala Pro Gly Trp Thr Trp Glu Gly Pro Gly
            115                 120                 125

CGG ATG AAA TCT GTT TAC AGA CAG AGG TTT GCA GGA AAG AGT GGG CGT         430
Arg Met Lys Ser Val Tyr Arg Gln Arg Phe Ala Gly Lys Ser Gly Arg
        130                 135                 140

GGA CTG CTT ACT GGG AAG CAC TGT TAA TGG CTG GTG CTC CAG ACC CCT         478
Gly Leu Leu Thr Gly Lys His Cys     Trp Leu Val Leu Gln Thr Pro
    145                 150                 155

CAC CTG GAG TTC CAG GAG GGA GAA ACC ATC ATG CTG AGG TGC CAC AGC         526
His Leu Glu Phe Gln Glu Gly Glu Thr Ile Met Leu Arg Cys His Ser
160                 165                 170

TGG AAG GAC AAG CCT CTG GTC AAG GTC ACA TTC TTC CAG AAT GGA AAA         574
Trp Lys Asp Lys Pro Leu Val Lys Val Thr Phe Phe Gln Asn Gly Lys
175                 180                 185                 190

TCC CAG AAA TTC TCC CGT TTG GAT CCC ACC TTC TCC ATC CCA CAA GCA         622
Ser Gln Lys Phe Ser Arg Leu Asp Pro Thr Phe Ser Ile Pro Gln Ala
                195                 200                 205

AAC CAC AGT CAC AGT GGT GAT TAC CAC TGC ACA GGA AAC ATA GGC TAC         670
Asn His Ser His Ser Gly Asp Tyr His Cys Thr Gly Asn Ile Gly Tyr
            210                 215                 220

ACG CTG TTC TCA TCC AAG CCT GTG ACC ATC ACT GTC CAA GTG CCC AGC         718
Thr Leu Phe Ser Ser Lys Pro Val Thr Ile Thr Val Gln Val Pro Ser
        225                 230                 235

ATG GGC AGC TCT TCA CCA ATG GGG ATC ATT GTG GCT GTG GTC ATT GCG         766
Met Gly Ser Ser Ser Pro Met Gly Ile Ile Val Ala Val Val Ile Ala
    240                 245                 250

ACT GCT GTA GCA GCC ATT GTT GCT GCT GTA GTG GCC TTG ATC TAC TGC         814
Thr Ala Val Ala Ala Ile Val Ala Ala Val Val Ala Leu Ile Tyr Cys
255                 260                 265                 270

AGG AAA AAG CGG ATT TCA GCC AAT TCC ACT GAT CCT GTG AAG GCT GCC         862
Arg Lys Lys Arg Ile Ser Ala Asn Ser Thr Asp Pro Val Lys Ala Ala
                275                 280                 285

CAA TTT GAG CCA CCT GGA CGT CAA ATG ATT GCC ATC AGA AAG AGA CAA         910
Gln Phe Glu Pro Pro Gly Arg Gln Met Ile Ala Ile Arg Lys Arg Gln
            290                 295                 300

CTT GAA GAA ACC AAC AAT GAC TAT GAA ACA GCT GAC GGC GGC TAC ATG         958
Leu Glu Glu Thr Asn Asn Asp Tyr Glu Thr Ala Asp Gly Gly Tyr Met
        305                 310                 315

ACT CTG AAC CCC AGG GCA CCT ACT GAC GAT AAA AAC ATC TAC CTG ACT         1006
Thr Leu Asn Pro Arg Ala Pro Thr Asp Asp Lys Asn Ile Tyr Leu Thr
320                 325                 330

CTT CCT CCC AAC GAC CAT GTC AAC AGT AAT AAC TAA                        1042
Leu Pro Pro Asn Asp His Val Asn Ser Asn Asn
335                 340                 345
```

(2) INFORMATION FOR SEQ ID NO:132:

(i) SEQUENCE CHARACTERISTICS:

(A) LENGTH: 345 amino acids
(B) TYPE: amino acid
(D) TOPOLOGY: linear (ii) MOLECULE TYPE: protein (xi) SEQUENCE DESCRIPTION: SEQ ID NO:132:

```
Asn Ser Gly Pro Arg Asn Leu Trp Leu Leu Gln Pro Leu Thr Val Leu
  1               5                  10                  15

Leu Leu Leu Ala Ser Ala Asp Ser Gln Ala Ala Ala Pro Pro Lys Ala
                 20                  25                  30

Val Leu Lys Leu Glu Pro Pro Trp Ile Asn Val Leu Gln Glu Asp Ser
             35                  40                  45

Val Thr Leu Thr Cys Gln Gly Ala Arg Ser Pro Glu Ser Asp Ser Ile
         50                  55                  60

Gln Trp Phe His Asn Gly Asn Leu Ile Pro Thr His Thr Gln Pro Ser
 65                  70                  75                  80

Tyr Arg Phe Lys Ala Asn Asn Asn Asp Ser Gly Glu Tyr Thr Cys Gln
                 85                  90                  95

Thr Gly Gln Thr Ser Leu Ser Asp Pro Val His Leu Thr Val Leu Ser
             100                 105                 110

Gly Gln Trp Arg Lys Ala Pro Gly Trp Thr Trp Glu Gly Pro Gly Arg
         115                 120                 125

Met Lys Ser Val Tyr Arg Gln Arg Phe Ala Gly Lys Ser Gly Arg Gly
130                 135                 140

Leu Leu Thr Gly Lys His Cys Trp Leu Val Leu Gln Thr Pro His Leu
145                 150                 155                 160

Glu Phe Gln Glu Gly Glu Thr Ile Met Leu Arg Cys His Ser Trp Lys
                 165                 170                 175

Asp Lys Pro Leu Val Lys Val Thr Phe Phe Gln Asn Gly Lys Ser Gln
             180                 185                 190

Lys Phe Ser Arg Leu Asp Pro Thr Phe Ser Ile Pro Gln Ala Asn His
         195                 200                 205

Ser His Ser Gly Asp Tyr His Cys Thr Gly Asn Ile Gly Tyr Thr Leu
210                 215                 220

Phe Ser Ser Lys Pro Val Thr Ile Thr Val Gln Val Pro Ser Met Gly
225                 230                 235                 240

Ser Ser Ser Pro Met Gly Ile Ile Val Ala Val Val Ile Ala Thr Ala
                 245                 250                 255

Val Ala Ala Ile Val Ala Ala Val Val Ala Leu Ile Tyr Cys Arg Lys
             260                 265                 270

Lys Arg Ile Ser Ala Asn Ser Thr Asp Pro Val Lys Ala Ala Gln Phe
         275                 280                 285

Glu Pro Pro Gly Arg Gln Met Ile Ala Ile Arg Lys Arg Gln Leu Glu
290                 295                 300

Glu Thr Asn Asn Asp Tyr Glu Thr Ala Asp Gly Gly Tyr Met Thr Leu
305                 310                 315                 320

Asn Pro Arg Ala Pro Thr Asp Asp Lys Asn Ile Tyr Leu Thr Leu Pro
                 325                 330                 335

Pro Asn Asp His Val Asn Ser Asn Asn
             340                 345
```

(2) INFORMATION FOR SEQ ID NO:133:

(i) SEQUENCE CHARACTERISTICS:
(A) LENGTH: 261 amino acids
(B) TYPE: amino acid (C) STRANDEDNESS:
        (D) TOPOLOGY: linear (ii) MOLECULE TYPE: protein (xi) SEQUENCE DESCRIPTION: SEQ ID NO:133:

Met Phe Gln Asn Ala His Ser Gly Ser Gln Trp Leu Leu Pro Pro Leu
    1               5                   10                  15

Thr Ile Leu Leu Leu Phe Ala Phe Ala Asp Arg Gln Ser Ala Ala Leu
                    20                  25                  30

Pro Lys Ala Val Val Lys Leu Asp Pro Pro Trp Ile Gln Val Leu Lys
                35                  40                  45

Glu Asp Met Val Thr Leu Met Cys Glu Gly Thr His Asn Pro Gly Asn
    50                  55                  60

Ser Ser Thr Gln Trp Phe His Asn Gly Arg Ser Ile Arg Ser Gln Val
    65                  70                  75                  80

Gln Ala Ser Tyr Thr Phe Lys Ala Thr Val Asn Asp Ser Gly Glu Tyr
                    85                  90                  95

Arg Cys Gln Met Glu Gln Thr Arg Leu Ser Asp Pro Val Asp Leu Gly
                100                 105                 110

Val Ile Ser Asp Trp Leu Leu Leu Gln Thr Pro Gln Arg Val Phe Leu
                115                 120                 125

Glu Gly Glu Thr Ile Thr Leu Arg Cys His Ser Trp Arg Asn Lys Leu
    130                 135                 140

Leu Asn Arg Ile Ser Phe Phe His Asn Glu Lys Ser Val Arg Tyr His
    145                 150                 155                 160

His Tyr Lys Ser Asn Phe Ser Ile Pro Lys Ala Asn His Ser His Ser
                    165                 170                 175

Gly Asp Tyr Tyr Cys Lys Gly Ser Leu Gly Ser Thr Gln His Gln Ser
                180                 185                 190

Lys Glu Val Thr Ile Thr Val Gln Asp Pro Ala Thr Thr Ser Ser Ile
                195                 200                 205

Ser Leu Val Trp Tyr His Thr Ala Phe Ser Leu Val Met Cys Leu Leu
    210                 215                 220

Phe Ala Val Asp Thr Gly Leu Tyr Phe Tyr Val Arg Arg Asn Leu Gln
    225                 230                 235                 240

Thr Pro Arg Glu Tyr Trp Arg Lys Ser Leu Ser Ile Arg Lys His Gln
                    245                 250                 255

Ala Pro Gln Asp Lys
                260

(2) INFORMATION FOR SEQ ID NO:134:

(i) SEQUENCE CHARACTERISTICS:
        (A) LENGTH: 330 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:134:

Met Glu Ser Asn Trp Thr Val His Val Phe Ser Arg Thr Leu Cys His
    1               5                   10                  15

Met Leu Leu Trp Thr Ala Val Leu Asn Leu Ala Ala Gly Thr His Asp
                    20                  25                  30

Leu Pro Lys Ala Val Val Lys Leu Glu Pro Pro Trp Ile Gln Val Leu
                35                  40                  45

```
            Lys Glu Asp Thr Val Thr Leu Thr Cys Glu Gly Thr His Asn Pro Gly
             50                  55                  60
            Asn Ser Ser Thr Gln Trp Phe His Asn Gly Arg Ser Ile Arg Ser Gln
             65                  70                  75                  80
            Val Gln Ala Ser Tyr Thr Phe Lys Ala Thr Val Asn Asp Ser Gly Glu
                                 85                  90                  95
            Tyr Arg Cys Gln Met Glu Gln Thr Arg Leu Ser Asp Pro Val Asp Leu
                            100                 105                 110
            Gly Val Ile Ser Asp Trp Leu Leu Gln Pro Thr Gln Leu Val Phe
                        115                 120                 125
            Leu Glu Gly Glu Thr Ile Thr Leu Arg Cys His Ser Trp Arg Asn Lys
            130                 135                 140
            Leu Leu Asn Arg Ile Ser Phe Phe His Asn Glu Lys Ser Val Arg Tyr
            145                 150                 155                 160
            His His Tyr Ser Ser Asn Phe Ser Ile Pro Lys Ala Asn His Ser His
                            165                 170                 175
            Ser Gly Asp Tyr Tyr Cys Lys Gly Ser Leu Gly Arg Thr Leu His Gln
                        180                 185                 190
            Ser Lys Pro Val Thr Ile Thr Val Gln Gly Pro Lys Ser Ser Arg Ser
                    195                 200                 205
            Leu Pro Val Leu Thr Ile Val Ala Ala Val Thr Gly Ile Ala Val Ala
            210                 215                 220
            Ala Ile Val Ile Ile Leu Val Ser Leu Val Tyr Leu Lys Lys Lys Gln
            225                 230                 235                 240
            Val Pro Ala Leu Pro Gly Asn Pro Asp His Arg Glu Met Gly Glu Thr
                            245                 250                 255
            Leu Pro Glu Glu Val Gly Glu Tyr Arg Gln Pro Ser Gly Gly Ser Val
                        260                 265                 270
            Pro Val Ser Pro Gly Pro Pro Ser Gly Leu Glu Pro Thr Ser Ser Ser
                    275                 280                 285
            Pro Tyr Asn Pro Pro Asp Leu Glu Glu Ala Pro Lys Thr Glu Ala Glu
                290                 295                 300
            Asn Thr Ile Thr Tyr Ser Leu Leu Lys His Pro Glu Ala Leu Asp Glu
            305                 310                 315                 320
            Glu Thr Glu His Asp Tyr Gln Asn His Ile
                            325                 330

(2) INFORMATION FOR SEQ ID NO:135:

(i) SEQUENCE CHARACTERISTICS:
        (A) LENGTH: 1162 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 57..905

(xi) SEQUENCE DESCRIPTION: SEQ ID NO:135:

CTTGCAGCTG ACTCGCTCCA GAGCTGATGG GAATCCTGCC GTTCCTACTG ATCCCC                56

ATG GAG AGC AAC TGG ACT GTC CAT GTG TTC TCA CGG ACT TTG TGC CAT           104
Met Glu Ser Asn Trp Thr Val His Val Phe Ser Arg Thr Leu Cys His
  1               5                  10                  15

ATG CTA CTG TGG ACA GCC GTG CTA AAT CTT GCT GCT GGG ACT CAT GAT           152
Met Leu Leu Trp Thr Ala Val Leu Asn Leu Ala Ala Gly Thr His Asp
             20                  25                  30
```

```
CTT CCA AAG GCT GTG GTC AAA CTC GAG CCC CCG TGG ATC CAG GTG CTC      200
Leu Pro Lys Ala Val Val Lys Leu Glu Pro Pro Trp Ile Gln Val Leu
        35                  40                  45

AAG GAA GAC ACG GTG ACA CTG ACA TGC GAA GGG ACC CAC AAC CCT GGG      248
Lys Glu Asp Thr Val Thr Leu Thr Cys Glu Gly Thr His Asn Pro Gly
 50                  55                  60

AAC TCT TCT ACC CAG TGG TTC CAC AAT GGG AGG TCC ATC CGG AGC CAG      296
Asn Ser Ser Thr Gln Trp Phe His Asn Gly Arg Ser Ile Arg Ser Gln
 65                  70                  75                  80

GTC CAA GCC AGC TAC ACG TTT AAG GCC ACA GTC AAT GAC AGT GGA GAA      344
Val Gln Ala Ser Tyr Thr Phe Lys Ala Thr Val Asn Asp Ser Gly Glu
                 85                  90                  95

TAT CGG TGT CAA ATG GAG CAG ACC CGC CTC AGC GAC CCT GTA GAT CTG      392
Tyr Arg Cys Gln Met Glu Gln Thr Arg Leu Ser Asp Pro Val Asp Leu
                100                 105                 110

GGA GTG ATT TCT GAC TGG CTG CTG CTC CAG ACC CCT CAG CTG GTG TTT      440
Gly Val Ile Ser Asp Trp Leu Leu Leu Gln Thr Pro Gln Leu Val Phe
            115                 120                 125

CTG GAA GGG GAA ACC ATC ACG CTA AGG TGC CAT AGC TGG AGG AAC AAA      488
Leu Glu Gly Glu Thr Ile Thr Leu Arg Cys His Ser Trp Arg Asn Lys
130                 135                 140

CTA CTG AAC AGG ATC TCG TTC TTC CAT AAT GAA AAA TCC GTG AGG TAT      536
Leu Leu Asn Arg Ile Ser Phe Phe His Asn Glu Lys Ser Val Arg Tyr
145                 150                 155                 160

CAT CAC TAC AGT AGT AAT TTC TCT ATC CCA AAA GCC AAC CAC AGT CAC      584
His His Tyr Ser Ser Asn Phe Ser Ile Pro Lys Ala Asn His Ser His
                165                 170                 175

AGT GGG GAC TAC TAC TGC AAA GGA AGT CTA GGA AGG ACA CTG CAC CAG      632
Ser Gly Asp Tyr Tyr Cys Lys Gly Ser Leu Gly Arg Thr Leu His Gln
                180                 185                 190

TCC AAG CCT GTC ACC ATC ACT GTC CAA GGG CCC AAG TCC AGC AGG TCT      680
Ser Lys Pro Val Thr Ile Thr Val Gln Gly Pro Lys Ser Ser Arg Ser
            195                 200                 205

TTA CCA GTA TTG ACA ATT GTG GCT GCT GTC ACT GGG ATT GCT GTC GCA      728
Leu Pro Val Leu Thr Ile Val Ala Ala Val Thr Gly Ile Ala Val Ala
        210                 215                 220

GCC ATT GTT ATT ATC CTA GTA TCC TTG GTC TAT CTC AAG AAA AAG CAG      776
Ala Ile Val Ile Ile Leu Val Ser Leu Val Tyr Leu Lys Lys Lys Gln
225                 230                 235                 240

GTT CCA GAC AAT CCT CCT GAT CTG GAA GAA GCT GCC AAA ACT GAG GCT      824
Val Pro Asp Asn Pro Pro Asp Leu Glu Glu Ala Ala Lys Thr Glu Ala
                245                 250                 255

GAG AAT ACG ATC ACC TAC TCA CTT CTC AAG CAT CCC GAA GCC CTG GAT      872
Glu Asn Thr Ile Thr Tyr Ser Leu Leu Lys His Pro Glu Ala Leu Asp
                260                 265                 270

GAA GAA ACA GAG CAT GAT TAC CAG AAC CAC ATT TAGTCTCCCT TGGCATTGGG    925
Glu Glu Thr Glu His Asp Tyr Gln Asn His Ile
            275                 280

AAAAGCAAGC CAGAAAGGCC AGGATCTAGT GTCTCCTGGT CCAAGGGATG CTGTAGATAT    985

TAAAGAAAAC ATCCAGAGTC ACTTCTGTGA GTCCTGAAAC CAACAGACAC TACGAGATTG   1045

GTTCCCAATG GTTGACTGTA CTAATGACTC CCATAACTTA CAGCTTCCCA ACTCAAGACT   1105

CTTCTGCTAT CGATCCACAC TGCCACTAAA ATTAATCAAC TTACTGCCGT TAAGAGA     1162
```

(2) INFORMATION FOR SEQ ID NO:136:

(i) SEQUENCE CHARACTERISTICS:
        (A) LENGTH: 283 amino acids
        (B) TYPE: amino acid
        (D) TOPOLOGY: linear (ii) MOLECULE TYPE: protein (xi) SEQUENCE DESCRIPTION: SEQ ID NO:136:

```
Met Glu Ser Asn Trp Thr Val His Val Phe Ser Arg Thr Leu Cys His
1               5                   10                  15

Met Leu Leu Trp Thr Ala Val Leu Asn Leu Ala Ala Gly Thr His Asp
            20                  25                  30

Leu Pro Lys Ala Val Val Lys Leu Glu Pro Pro Trp Ile Gln Val Leu
        35                  40                  45

Lys Glu Asp Thr Val Thr Leu Thr Cys Glu Gly Thr His Asn Pro Gly
    50                  55                  60

Asn Ser Ser Thr Gln Trp Phe His Asn Gly Arg Ser Ile Arg Ser Gln
65                  70                  75                  80

Val Gln Ala Ser Tyr Thr Phe Lys Ala Thr Val Asn Asp Ser Gly Glu
                85                  90                  95

Tyr Arg Cys Gln Met Glu Gln Thr Arg Leu Ser Asp Pro Val Asp Leu
                100                 105                 110

Gly Val Ile Ser Asp Trp Leu Leu Leu Gln Thr Pro Gln Leu Val Phe
            115                 120                 125

Leu Glu Gly Glu Thr Ile Thr Leu Arg Cys His Ser Trp Arg Asn Lys
130                 135                 140

Leu Leu Asn Arg Ile Ser Phe Phe His Asn Glu Lys Ser Val Arg Tyr
145                 150                 155                 160

His His Tyr Ser Ser Asn Phe Ser Ile Pro Lys Ala Asn His Ser His
                165                 170                 175

Ser Gly Asp Tyr Tyr Cys Lys Gly Ser Leu Gly Arg Thr Leu His Gln
                180                 185                 190

Ser Lys Pro Val Thr Ile Thr Val Gln Gly Pro Lys Ser Ser Arg Ser
        195                 200                 205

Leu Pro Val Leu Thr Ile Val Ala Ala Val Thr Gly Ile Ala Val Ala
    210                 215                 220

Ala Ile Val Ile Ile Leu Val Ser Leu Val Tyr Leu Lys Lys Lys Gln
225                 230                 235                 240

Val Pro Asp Asn Pro Pro Asp Leu Glu Glu Ala Ala Lys Thr Glu Ala
                245                 250                 255

Glu Asn Thr Ile Thr Tyr Ser Leu Leu Lys His Pro Glu Ala Leu Asp
                260                 265                 270

Glu Glu Thr Glu His Asp Tyr Gln Asn His Ile
                275                 280
```